(12) United States Patent
Concha et al.

(10) Patent No.: US 11,079,396 B2
(45) Date of Patent: Aug. 3, 2021

(54) ALPHA-SYNUCLEIN DETECTION USING BEADS

(71) Applicant: Amprion, Inc., San Francisco, CA (US)

(72) Inventors: Luis Concha, San Diego, OH (US); Carly Farris, San Diego, CA (US); Bret Holguin, San Diego, CA (US); Russell Lebovitz, Oakland, CA (US); Benedikt Vollrath, San Diego, CA (US); Frank Espin, Oceanside, CA (US)

(73) Assignee: Amprion, Inc., San Francisco, CA (US)

( * ) Notice: Subject to any disclaimer, the term of this patent is extended or adjusted under 35 U.S.C. 154(b) by 0 days.

(21) Appl. No.: 17/011,374

(22) Filed: Sep. 3, 2020

(65) Prior Publication Data

US 2021/0063416 A1 Mar. 4, 2021

Related U.S. Application Data

(60) Provisional application No. 62/895,535, filed on Sep. 4, 2019, provisional application No. 63/040,144, filed on Jun. 17, 2020, provisional application No. 63/042,679, filed on Jun. 23, 2020, provisional application No. 63/045,593, filed on Jun. 29, 2020, provisional application No. 63/073,420, filed on Sep. 1, 2020, provisional application No. 63/073,424, filed on Sep. 1, 2020.

(51) Int. Cl.
*G01N 33/68* (2006.01)

(52) U.S. Cl.
CPC . *G01N 33/6896* (2013.01); *G01N 2800/2814* (2013.01); *G01N 2800/2835* (2013.01)

(58) Field of Classification Search
CPC ....... G01N 33/6896; G01N 2800/2814; G01N 2800/2835
See application file for complete search history.

(56) References Cited

U.S. PATENT DOCUMENTS

| 9,910,049 B2 * | 3/2018 | Jara | G01N 33/6896 |
| 2008/0118938 A1 * | 5/2008 | Estrada | G01N 33/6896 435/7.92 |
| 2012/0094307 A1 | 4/2012 | Tajima | |
| 2016/0077111 A1 | 3/2016 | Jara et al. | |
| 2019/0302128 A1 | 10/2019 | Green et al. | |
| 2020/0232996 A1 | 7/2020 | Caughey et al. | |

OTHER PUBLICATIONS

International Search Report and Written Opinion dated Dec. 14, 2020, for Application No. PCT/US2020/049130 filed Sep. 2, 2020 (11 pages).
Abdolvahabi et al., "How Do Gyrating Beads Accelerate Amyloid Fibrillization?" Biophys J, Jan. 24, 2017 (Jan. 24, 2017), vol. 112, pp. 250-264, entire document.
Giehm et al., "Strategies to increase the reproducibility of protein fibrillization in plate reader assays", Analytical Biochemistry 400 (2010) 270-281.

\* cited by examiner

*Primary Examiner* — Olga N Chernyshev
(74) *Attorney, Agent, or Firm* — Kern Kendrick, LLC; Benjamen E. Kern

(57) ABSTRACT

A method is provided for determining the presence of soluble, misfolded α-synuclein protein in a biological sample. The method comprises contacting the biological sample with a pre-incubation mixture, the pre-incubation mixture comprising: a monomeric α-synuclein protein; a buffer composition; a salt; and an indicator, to form an incubation mixture. An incubation cycle is conducted on the incubation mixture in the presence of either a silicon nitride bead or a borosilicate glass bead having a diameter of from about 1 mm to about 5 mm. The method further comprises determining if a detectable amount of misfolded α-synuclein aggregate is present in the biological sample.

20 Claims, 48 Drawing Sheets

Specification includes a Sequence Listing.

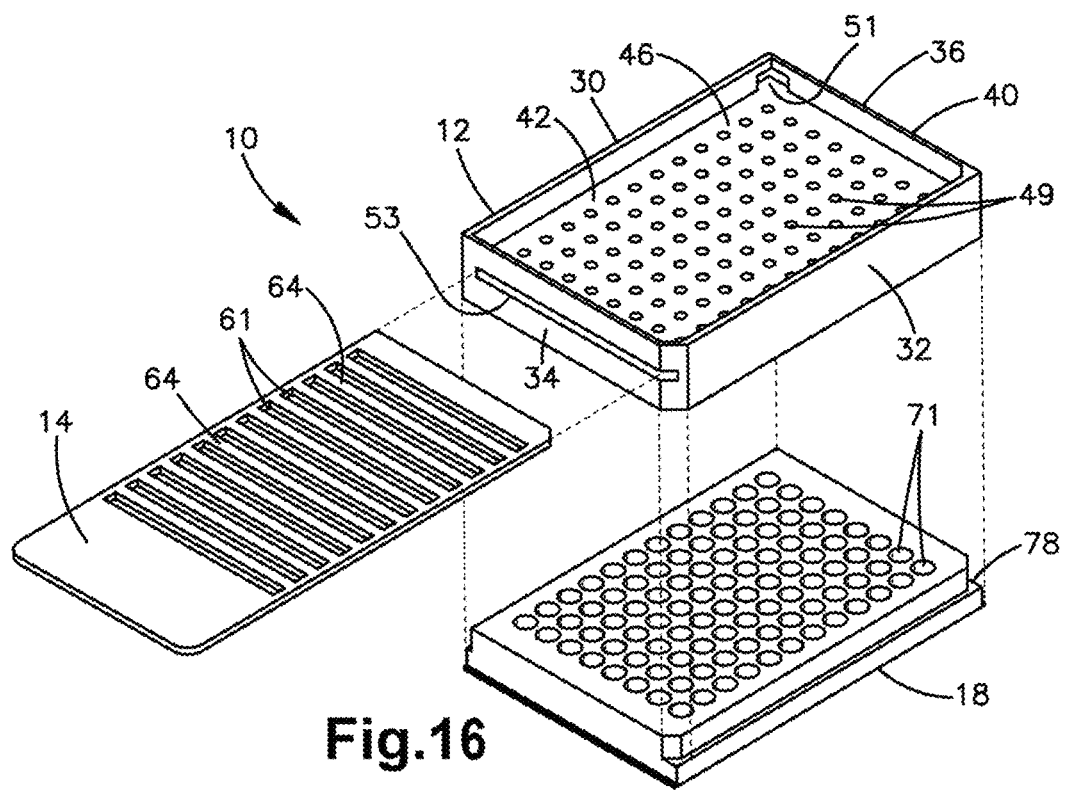
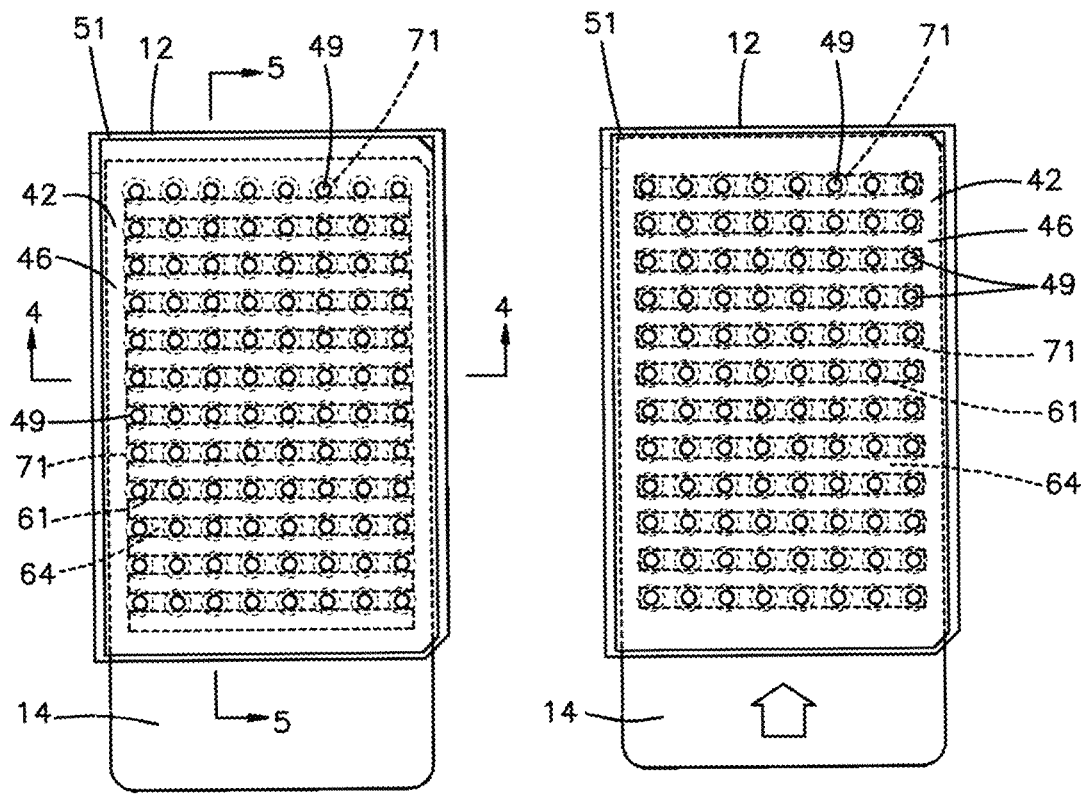

SEQUENCE LISTING

<160> NUMBER OF SEQ ID NOS: 19

<210> SEQ ID NO 1
<211> LENGTH: 140
<212> TYPE: PRT
<213> ORGANISM: Artificial Sequence
<220> FEATURE:
<223> OTHER INFORMATION: Synthetic

<400> SEQUENCE: 1

Met Asp Val Phe Met Lys Gly Leu Ser Lys Ala Lys Glu Gly Val Val
1               5                   10                  15

Ala Ala Ala Glu Lys Thr Lys Gln Gly Val Ala Glu Ala Gly Lys
            20                  25                  30

```
Thr Lys Glu Gly Val Leu Tyr Val Gly Ser Lys Thr Lys Glu Gly Val
         35                  40                  45

Val His Gly Val Ala Thr Val Ala Glu Lys Thr Lys Glu Gln Val Thr
     50                  55                  60

Asn Val Gly Gly Ala Val Val Thr Gly Val Thr Ala Val Ala Gln Lys
 65                  70                  75                  80

Thr Val Glu Gly Ala Gly Ser Ile Ala Ala Thr Gly Phe Val Lys
             85                  90                  95

Lys Asp Gln Leu Gly Lys Asn Glu Glu Gly Ala Pro Gln Glu Gly Ile
             100                 105                 110

Leu Glu Asp Met Pro Val Asp Pro Asp Asn Glu Ala Tyr Glu Met Pro
             115                 120                 125

Ser Glu Glu Gly Tyr Gln Asp Tyr Glu Pro Glu Ala
             130                 135                 140

<210> SEQ ID NO 2
<211> LENGTH: 146
<212> TYPE: PRT
<213> ORGANISM: Artificial Sequence
<220> FEATURE:
<223> OTHER INFORMATION: Synthetic

<400> SEQUENCE: 2

Met Asp Val Phe Met Lys Gly Leu Ser Lys Ala Lys Glu Gly Val Val
 1               5                  10                  15

Ala Ala Ala Glu Lys Thr Lys Gln Gly Val Ala Glu Ala Ala Gly Lys
             20                  25                  30

Thr Lys Glu Gly Val Leu Tyr Val Gly Ser Lys Thr Lys Glu Gly Val
         35                  40                  45

Val His Gly Val Ala Thr Val Ala Glu Lys Thr Lys Glu Gln Val Thr
     50                  55                  60

Asn Val Gly Gly Ala Val Val Thr Gly Val Thr Ala Val Ala Gln Lys
 65                  70                  75                  80

Thr Val Glu Gly Ala Gly Ser Ile Ala Ala Thr Gly Phe Val Lys
             85                  90                  95

Lys Asp Gln Leu Gly Lys Asn Glu Glu Gly Ala Pro Gln Glu Gly Ile
             100                 105                 110

Leu Glu Asp Met Pro Val Asp Pro Asp Asn Glu Ala Tyr Glu Met Pro
             115                 120                 125

Ser Glu Glu Gly Tyr Gln Asp Tyr Glu Pro Glu Ala His His His His
             130                 135                 140
His His
145

<210> SEQ ID NO 3
<211> LENGTH: 146
<212> TYPE: PRT
<213> ORGANISM: Artificial Sequence
<220> FEATURE:
<223> OTHER INFORMATION: Synthetic

<400> SEQUENCE: 3

His His His His His His Met Asp Val Phe Met Lys Gly Leu Ser Lys
 1               5                  10                  15

Ala Lys Glu Gly Val Val Ala Ala Ala Glu Lys Thr Lys Gln Gly Val
             20                  25                  30

Ala Glu Ala Ala Gly Lys Thr Lys Glu Gly Val Leu Tyr Val Gly Ser
```

```
                35                  40                  45
Lys Thr Lys Glu Gly Val Val His Gly Val Ala Thr Val Ala Glu Lys
        50                  55                  60

Thr Lys Glu Gln Val Thr Asn Val Gly Gly Ala Val Val Thr Gly Val
 65                 70                  75                  80

Thr Ala Val Ala Gln Lys Thr Val Glu Gly Ala Gly Ser Ile Ala Ala
                85                  90                  95

Ala Thr Gly Phe Val Lys Lys Asp Gln Leu Gly Lys Asn Glu Glu Gly
            100                 105                 110

Ala Pro Gln Glu Gly Ile Leu Glu Asp Met Pro Val Asp Pro Asp Asn
        115                 120                 125

Glu Ala Tyr Glu Met Pro Ser Glu Gly Tyr Gln Asp Tyr Glu Pro
    130                 135                 140

Glu Ala
145

<210> SEQ ID NO 4
<211> LENGTH: 147
<212> TYPE: PRT
<213> ORGANISM: Artificial Sequence
<220> FEATURE:
<223> OTHER INFORMATION: Synthetic

<400> SEQUENCE: 4

Met Asp Val Phe Met Lys Gly Leu Ser Lys Ala Lys Glu Gly Val Val
 1               5                  10                  15

Ala Ala Ala Glu Lys Thr Lys Gln Gly Val Ala Glu Ala Ala Gly Lys
                20                  25                  30

Thr Lys Glu Gly Val Leu Tyr Val Gly Ser Lys Thr Lys Glu Gly Val
            35                  40                  45

Val His Gly Val Ala Thr Val Ala Glu Lys Thr Lys Glu Gln Val Thr
        50                  55                  60

Asn Val Gly Gly Ala Val Val Thr Gly Val Thr Ala Val Ala Gln Lys
 65                 70                  75                  80

Thr Val Glu Gly Ala Gly Ser Ile Ala Ala Ala Thr Gly Phe Val Lys
                85                  90                  95

Lys Asp Gln Leu Gly Lys Asn Glu Glu Gly Ala Pro Gln Glu Gly Ile
            100                 105                 110

Leu Glu Asp Met Pro Val Asp Pro Asp Asn Glu Ala Tyr Glu Met Pro
        115                 120                 125

Ser Glu Glu Gly Tyr Gln Asp Tyr Glu Pro Glu Ala Asp Tyr Lys Asp
    130                 135                 140

Asp Asp Asp
145

<210> SEQ ID NO 5
<211> LENGTH: 147
<212> TYPE: PRT
<213> ORGANISM: Artificial Sequence
<220> FEATURE:
<223> OTHER INFORMATION: Synthetic

<400> SEQUENCE: 5

Asp Tyr Lys Asp Asp Asp Asp Met Asp Val Phe Met Lys Gly Leu Ser
 1               5                  10                  15

Lys Ala Lys Glu Gly Val Val Ala Ala Ala Glu Lys Thr Lys Gln Gly
                20                  25                  30
```

```
Val Ala Glu Ala Ala Gly Lys Thr Lys Glu Gly Val Leu Tyr Val Gly
         35                  40                  45

Ser Lys Thr Lys Glu Gly Val His Gly Val Ala Thr Val Ala Glu
 50                  55                  60

Lys Thr Lys Glu Gln Val Thr Asn Val Gly Gly Ala Val Val Thr Gly
 65                  70                  75                  80

Val Thr Ala Val Ala Gln Lys Thr Val Glu Gly Ala Gly Ser Ile Ala
                 85                  90                  95

Ala Ala Thr Gly Phe Val Lys Lys Asp Gln Leu Gly Lys Asn Glu Glu
            100                 105                 110

Gly Ala Pro Gln Glu Gly Ile Leu Glu Asp Met Pro Val Asp Pro Asp
            115                 120                 125

Asn Glu Ala Tyr Glu Met Pro Ser Glu Glu Gly Tyr Gln Asp Tyr Glu
    130                 135                 140

Pro Glu Ala
145
```

<210> SEQ ID NO 6
<211> LENGTH: 148
<212> TYPE: PRT
<213> ORGANISM: Artificial Sequence
<220> FEATURE:
<223> OTHER INFORMATION: Synthetic

<400> SEQUENCE: 6

```
Met Asp Val Phe Met Lys Gly Leu Ser Lys Ala Lys Glu Gly Val Val
 1               5                  10                  15

Ala Ala Ala Glu Lys Thr Lys Gln Gly Val Ala Glu Ala Gly Lys
                 20                  25                  30

Thr Lys Glu Gly Val Leu Tyr Val Gly Ser Lys Thr Lys Glu Gly Val
             35                  40                  45

Val His Gly Val Ala Thr Val Ala Glu Lys Thr Lys Glu Gln Val Thr
 50                  55                  60

Asn Val Gly Gly Ala Val Val Thr Gly Val Thr Ala Val Ala Gln Lys
 65                  70                  75                  80

Thr Val Glu Gly Ala Gly Ser Ile Ala Ala Ala Thr Gly Phe Val Lys
                 85                  90                  95

Lys Asp Gln Leu Gly Lys Asn Glu Glu Gly Ala Pro Gln Glu Gly Ile
            100                 105                 110

Leu Glu Asp Met Pro Val Asp Pro Asp Asn Glu Ala Tyr Glu Met Pro
            115                 120                 125

Ser Glu Glu Gly Tyr Gln Asp Tyr Glu Pro Glu Ala Asp Tyr Lys Asp
    130                 135                 140

Asp Asp Asp Lys
145
```

<210> SEQ ID NO 7
<211> LENGTH: 148
<212> TYPE: PRT
<213> ORGANISM: Artificial Sequence
<220> FEATURE:
<223> OTHER INFORMATION: Synthetic

<400> SEQUENCE: 7

```
Asp Tyr Lys Asp Asp Asp Lys Met Asp Val Phe Met Lys Gly Leu
 1               5                  10                  15

Ser Lys Ala Lys Glu Gly Val Val Ala Ala Ala Glu Lys Thr Lys Gln
                 20                  25                  30
```

Gly Val Ala Glu Ala Gly Lys Thr Lys Glu Gly Val Leu Tyr Val
            35                  40                  45

Gly Ser Lys Thr Lys Glu Gly Val Val His Gly Val Ala Thr Val Ala
    50                  55                  60

Glu Lys Thr Lys Glu Gln Val Thr Asn Val Gly Gly Ala Val Val Thr
65                  70                  75                  80

Gly Val Thr Ala Val Ala Gln Lys Thr Val Glu Gly Ala Gly Ser Ile
                85                  90                  95

Ala Ala Ala Thr Gly Phe Val Lys Lys Asp Gln Leu Gly Lys Asn Glu
            100                 105                 110

Glu Gly Ala Pro Gln Glu Gly Ile Leu Glu Asp Met Pro Val Asp Pro
        115                 120                 125

Asp Asn Glu Ala Tyr Glu Met Pro Ser Glu Gly Tyr Gln Asp Tyr
    130                 135                 140

Glu Pro Glu Ala
145

<210> SEQ ID NO 8
<211> LENGTH: 147
<212> TYPE: PRT
<213> ORGANISM: Artificial Sequence
<220> FEATURE:
<223> OTHER INFORMATION: Synthetic

<400> SEQUENCE: 8

Met Asp Val Phe Met Lys Gly Leu Ser Lys Ala Lys Glu Gly Val Val
1               5                   10                  15

Ala Ala Ala Glu Lys Thr Lys Gln Gly Val Ala Glu Ala Ala Gly Lys
            20                  25                  30

Thr Lys Glu Gly Val Leu Tyr Val Gly Ser Lys Thr Lys Glu Gly Val
        35                  40                  45

Val His Gly Val Ala Thr Val Ala Glu Lys Thr Lys Glu Gln Val Thr
    50                  55                  60

Asn Val Gly Gly Ala Val Val Thr Gly Val Thr Ala Val Ala Gln Lys
65                  70                  75                  80

Thr Val Glu Gly Ala Gly Ser Ile Ala Ala Ala Thr Gly Phe Val Lys
                85                  90                  95

Lys Asp Gln Leu Gly Lys Asn Glu Glu Gly Ala Pro Gln Glu Gly Ile
            100                 105                 110

Leu Glu Asp Met Pro Val Asp Pro Asp Asn Glu Ala Tyr Glu Met Pro
        115                 120                 125

Ser Glu Glu Gly Tyr Gln Asp Tyr Glu Pro Glu Ala Asp Tyr Lys Asp
    130                 135                 140

Asp Asp Lys
145

<210> SEQ ID NO 9
<211> LENGTH: 147
<212> TYPE: PRT
<213> ORGANISM: Artificial Sequence
<220> FEATURE:
<223> OTHER INFORMATION: Synthetic

<400> SEQUENCE: 9

Asp Tyr Lys Asp Asp Asp Lys Met Asp Val Phe Met Lys Gly Leu Ser
1               5                   10                  15

Lys Ala Lys Glu Gly Val Val Ala Ala Ala Glu Lys Thr Lys Gln Gly

```
            20                  25                  30
Val Ala Glu Ala Ala Gly Lys Thr Lys Glu Gly Val Leu Tyr Val Gly
                35                  40                  45

Ser Lys Thr Lys Glu Gly Val His Gly Val Ala Thr Val Ala Glu
        50                  55                  60

Lys Thr Lys Glu Gln Val Thr Asn Val Gly Gly Ala Val Val Thr Gly
65                  70                  75                  80

Val Thr Ala Val Ala Gln Lys Thr Val Glu Gly Ala Gly Ser Ile Ala
                85                  90                  95

Ala Ala Thr Gly Phe Val Lys Lys Asp Gln Leu Gly Lys Asn Glu Glu
                100                 105                 110

Gly Ala Pro Gln Glu Gly Ile Leu Glu Asp Met Pro Val Asp Pro Asp
            115                 120                 125

Asn Glu Ala Tyr Glu Met Pro Ser Glu Glu Gly Tyr Gln Asp Tyr Glu
        130                 135                 140

Pro Glu Ala
145

<210> SEQ ID NO 10
<211> LENGTH: 149
<212> TYPE: PRT
<213> ORGANISM: Artificial Sequence
<220> FEATURE:
<223> OTHER INFORMATION: Synthetic

<400> SEQUENCE: 10

Met Asp Val Phe Met Lys Gly Leu Ser Lys Ala Lys Glu Gly Val Val
1               5                   10                  15

Ala Ala Ala Glu Lys Thr Lys Gln Gly Val Ala Glu Ala Ala Gly Lys
                20                  25                  30

Thr Lys Glu Gly Val Leu Tyr Val Gly Ser Lys Thr Lys Glu Gly Val
                35                  40                  45

Val His Gly Val Ala Thr Val Ala Glu Lys Thr Lys Glu Gln Val Thr
        50                  55                  60

Asn Val Gly Gly Ala Val Val Thr Gly Val Thr Ala Val Ala Gln Lys
65                  70                  75                  80

Thr Val Glu Gly Ala Gly Ser Ile Ala Ala Ala Thr Gly Phe Val Lys
                85                  90                  95

Lys Asp Gln Leu Gly Lys Asn Glu Glu Gly Ala Pro Gln Glu Gly Ile
                100                 105                 110

Leu Glu Asp Met Pro Val Asp Pro Asp Asn Glu Ala Tyr Glu Met Pro
            115                 120                 125

Ser Glu Glu Gly Tyr Gln Asp Tyr Glu Pro Glu Ala Tyr Pro Tyr Asp
        130                 135                 140

Val Pro Asp Tyr Ala
145

<210> SEQ ID NO 11
<211> LENGTH: 149
<212> TYPE: PRT
<213> ORGANISM: Artificial Sequence
<220> FEATURE:
<223> OTHER INFORMATION: Synthetic

<400> SEQUENCE: 11

Tyr Pro Tyr Asp Val Pro Asp Tyr Ala Met Asp Val Phe Met Lys Gly
1               5                   10                  15
```

Leu Ser Lys Ala Lys Glu Gly Val Val Ala Ala Ala Glu Lys Thr Lys
                20                  25                  30

Gln Gly Val Ala Glu Ala Ala Gly Lys Thr Lys Glu Gly Val Leu Tyr
            35                  40                  45

Val Gly Ser Lys Thr Lys Glu Gly Val Val His Gly Val Ala Thr Val
50                  55                  60

Ala Glu Lys Thr Lys Glu Gln Val Thr Asn Val Gly Gly Ala Val Val
65                  70                  75                  80

Thr Gly Val Thr Ala Val Ala Gln Lys Thr Val Glu Gly Ala Gly Ser
                85                  90                  95

Ile Ala Ala Ala Thr Gly Phe Val Lys Lys Asp Gln Leu Gly Lys Asn
            100                 105                 110

Glu Glu Gly Ala Pro Gln Glu Gly Ile Leu Glu Asp Met Pro Val Asp
        115                 120                 125

Pro Asp Asn Glu Ala Tyr Glu Met Pro Ser Glu Glu Gly Tyr Gln Asp
    130                 135                 140

Tyr Glu Pro Glu Ala
145

<210> SEQ ID NO 12
<211> LENGTH: 149
<212> TYPE: PRT
<213> ORGANISM: Artificial Sequence
<220> FEATURE:
<223> OTHER INFORMATION: Synthetic

<400> SEQUENCE: 12

Met Asp Val Phe Met Lys Gly Leu Ser Lys Ala Lys Glu Gly Val Val
1               5                   10                  15

Ala Ala Ala Glu Lys Thr Lys Gln Gly Val Ala Glu Ala Ala Gly Lys
                20                  25                  30

Thr Lys Glu Gly Val Leu Tyr Val Gly Ser Lys Thr Lys Glu Gly Val
            35                  40                  45

Val His Gly Val Ala Thr Val Ala Glu Lys Thr Lys Glu Gln Val Thr
50                  55                  60

Asn Val Gly Gly Ala Val Val Thr Gly Val Thr Ala Val Ala Gln Lys
65                  70                  75                  80

Thr Val Glu Gly Ala Gly Ser Ile Ala Ala Ala Thr Gly Phe Val Lys
                85                  90                  95

Lys Asp Gln Leu Gly Lys Asn Glu Glu Gly Ala Pro Gln Glu Gly Ile
            100                 105                 110

Leu Glu Asp Met Pro Val Asp Pro Asp Asn Glu Ala Tyr Glu Met Pro
        115                 120                 125

Ser Glu Glu Gly Tyr Gln Asp Tyr Glu Pro Glu Ala Tyr Ala Tyr Asp
    130                 135                 140

Val Pro Asp Tyr Ala
145

<210> SEQ ID NO 13
<211> LENGTH: 149
<212> TYPE: PRT
<213> ORGANISM: Artificial Sequence
<220> FEATURE:
<223> OTHER INFORMATION: Synthetic

<400> SEQUENCE: 13

Tyr Ala Tyr Asp Val Pro Asp Tyr Ala Met Asp Val Phe Met Lys Gly
1               5                   10                  15

```
Leu Ser Lys Ala Lys Glu Gly Val Val Ala Ala Glu Lys Thr Lys
            20                  25                  30

Gln Gly Val Ala Glu Ala Ala Gly Lys Thr Lys Glu Gly Val Leu Tyr
        35                  40                  45

Val Gly Ser Lys Thr Lys Glu Gly Val Val His Gly Val Ala Thr Val
    50                  55                  60

Ala Glu Lys Thr Lys Glu Gln Val Thr Asn Val Gly Gly Ala Val Val
65                  70                  75                  80

Thr Gly Val Thr Ala Val Ala Gln Lys Thr Val Glu Gly Ala Gly Ser
                85                  90                  95

Ile Ala Ala Ala Thr Gly Phe Val Lys Lys Asp Gln Leu Gly Lys Asn
            100                 105                 110

Glu Glu Gly Ala Pro Gln Glu Gly Ile Leu Glu Asp Met Pro Val Asp
        115                 120                 125

Pro Asp Asn Glu Ala Tyr Glu Met Pro Ser Glu Glu Gly Tyr Gln Asp
    130                 135                 140

Tyr Glu Pro Glu Ala
145

<210> SEQ ID NO 14
<211> LENGTH: 149
<212> TYPE: PRT
<213> ORGANISM: Artificial Sequence
<220> FEATURE:
<223> OTHER INFORMATION: Synthetic

<400> SEQUENCE: 14

Met Asp Val Phe Met Lys Gly Leu Ser Lys Ala Lys Glu Gly Val Val
1               5                   10                  15

Ala Ala Ala Glu Lys Thr Lys Gln Gly Val Ala Glu Ala Ala Gly Lys
            20                  25                  30

Thr Lys Glu Gly Val Leu Tyr Val Gly Ser Lys Thr Lys Glu Gly Val
        35                  40                  45

Val His Gly Val Ala Thr Val Ala Glu Lys Thr Lys Glu Gln Val Thr
    50                  55                  60

Asn Val Gly Gly Ala Val Val Thr Gly Val Thr Ala Val Ala Gln Lys
65                  70                  75                  80

Thr Val Glu Gly Ala Gly Ser Ile Ala Ala Ala Thr Gly Phe Val Lys
                85                  90                  95

Lys Asp Gln Leu Gly Lys Asn Glu Glu Gly Ala Pro Gln Glu Gly Ile
            100                 105                 110

Leu Glu Asp Met Pro Val Asp Pro Asp Asn Glu Ala Tyr Glu Met Pro
        115                 120                 125

Ser Glu Glu Gly Tyr Gln Asp Tyr Glu Pro Glu Ala Tyr Asp Val Pro
    130                 135                 140

Asp Tyr Ala Ser Leu
145

<210> SEQ ID NO 15
<211> LENGTH: 149
<212> TYPE: PRT
<213> ORGANISM: Artificial Sequence
<220> FEATURE:
<223> OTHER INFORMATION: Synthetic

<400> SEQUENCE: 15

Tyr Asp Val Pro Asp Tyr Ala Ser Leu Met Asp Val Phe Met Lys Gly
```

Leu Ser Lys Ala Lys Glu Gly Val Val Ala Ala Glu Lys Thr Lys
            20                  25                  30

Gln Gly Val Ala Glu Ala Ala Gly Lys Thr Lys Glu Gly Val Leu Tyr
            35                  40                  45

Val Gly Ser Lys Thr Lys Glu Gly Val Val His Gly Val Ala Thr Val
50                  55                  60

Ala Glu Lys Thr Lys Glu Gln Val Thr Asn Val Gly Gly Ala Val Val
65                  70                  75                  80

Thr Gly Val Thr Ala Val Ala Gln Lys Thr Val Glu Gly Ala Gly Ser
            85                  90                  95

Ile Ala Ala Ala Thr Gly Phe Val Lys Lys Asp Gln Leu Gly Lys Asn
            100                 105                 110

Glu Glu Gly Ala Pro Gln Glu Gly Ile Leu Glu Asp Met Pro Val Asp
            115                 120                 125

Pro Asp Asn Glu Ala Tyr Glu Met Pro Ser Glu Gly Tyr Gln Asp
            130                 135                 140

Tyr Glu Pro Glu Ala
145

<210> SEQ ID NO 16
<211> LENGTH: 150
<212> TYPE: PRT
<213> ORGANISM: Artificial Sequence
<220> FEATURE:
<223> OTHER INFORMATION: Synthetic

<400> SEQUENCE: 16

Met Asp Val Phe Met Lys Gly Leu Ser Lys Ala Lys Glu Gly Val Val
1               5                   10                  15

Ala Ala Ala Glu Lys Thr Lys Gln Gly Val Ala Glu Ala Ala Gly Lys
            20                  25                  30

Thr Lys Glu Gly Val Leu Tyr Val Gly Ser Lys Thr Lys Glu Gly Val
            35                  40                  45

Val His Gly Val Ala Thr Val Ala Glu Lys Thr Lys Glu Gln Val Thr
50                  55                  60

Asn Val Gly Gly Ala Val Val Thr Gly Val Thr Ala Val Ala Gln Lys
65                  70                  75                  80

Thr Val Glu Gly Ala Gly Ser Ile Ala Ala Ala Thr Gly Phe Val Lys
            85                  90                  95

Lys Asp Gln Leu Gly Lys Asn Glu Glu Gly Ala Pro Gln Glu Gly Ile
            100                 105                 110

Leu Glu Asp Met Pro Val Asp Pro Asp Asn Glu Ala Tyr Glu Met Pro
            115                 120                 125

Ser Glu Glu Gly Tyr Gln Asp Tyr Glu Pro Glu Ala Glu Gln Lys Leu
            130                 135                 140

Ile Ser Glu Glu Asp Leu
145                 150

<210> SEQ ID NO 17
<211> LENGTH: 150
<212> TYPE: PRT
<213> ORGANISM: Artificial Sequence
<220> FEATURE:
<223> OTHER INFORMATION: Synthetic

<400> SEQUENCE: 17

Glu Gln Lys Leu Ile Ser Glu Glu Asp Leu Met Asp Val Phe Met Lys
1               5                   10                  15

Gly Leu Ser Lys Ala Lys Glu Gly Val Val Ala Ala Glu Lys Thr
            20                  25                  30

Lys Gln Gly Val Ala Glu Ala Gly Lys Thr Lys Glu Gly Val Leu
        35                  40                  45

Tyr Val Gly Ser Lys Thr Lys Glu Gly Val Val His Gly Val Ala Thr
    50                  55                  60

Val Ala Glu Lys Thr Lys Glu Gln Val Thr Asn Val Gly Gly Ala Val
65                  70                  75                  80

Val Thr Gly Val Thr Ala Val Ala Gln Lys Thr Val Glu Gly Ala Gly
                85                  90                  95

Ser Ile Ala Ala Ala Thr Gly Phe Val Lys Lys Asp Gln Leu Gly Lys
                100                 105                 110

Asn Glu Glu Gly Ala Pro Gln Glu Gly Ile Leu Glu Asp Met Pro Val
                115                 120                 125

Asp Pro Asp Asn Glu Ala Tyr Glu Met Pro Ser Glu Glu Gly Tyr Gln
        130                 135                 140

Asp Tyr Glu Pro Glu Ala
145                 150

<210> SEQ ID NO 18
<211> LENGTH: 154
<212> TYPE: PRT
<213> ORGANISM: Artificial Sequence
<220> FEATURE:
<223> OTHER INFORMATION: Synthetic

<400> SEQUENCE: 18

Met Asp Val Phe Met Lys Gly Leu Ser Lys Ala Lys Glu Gly Val Val
1               5                   10                  15

Ala Ala Ala Glu Lys Thr Lys Gln Gly Val Ala Glu Ala Ala Gly Lys
                20                  25                  30

Thr Lys Glu Gly Val Leu Tyr Val Gly Ser Lys Thr Lys Glu Gly Val
            35                  40                  45

Val His Gly Val Ala Thr Val Ala Glu Lys Thr Lys Glu Gln Val Thr
50                  55                  60

Asn Val Gly Gly Ala Val Val Thr Gly Val Thr Ala Val Ala Gln Lys
65                  70                  75                  80

Thr Val Glu Gly Ala Gly Ser Ile Ala Ala Ala Thr Gly Phe Val Lys
                85                  90                  95

Lys Asp Gln Leu Gly Lys Asn Glu Glu Gly Ala Pro Gln Glu Gly Ile
            100                 105                 110

Leu Glu Asp Met Pro Val Asp Pro Asp Asn Glu Ala Tyr Glu Met Pro
        115                 120                 125

Ser Glu Glu Gly Tyr Gln Asp Tyr Glu Pro Glu Ala Gly Lys Pro Ile
130                 135                 140

Pro Asn Pro Leu Leu Gly Leu Asp Ser Thr
145                 150

<210> SEQ ID NO 19
<211> LENGTH: 154
<212> TYPE: PRT
<213> ORGANISM: Artificial Sequence
<220> FEATURE:
<223> OTHER INFORMATION: Synthetic

<400> SEQUENCE: 19

```
Gly Lys Pro Ile Pro Asn Pro Leu Leu Gly Leu Asp Ser Thr Met Asp
1               5                   10                  15

Val Phe Met Lys Gly Leu Ser Lys Ala Lys Glu Gly Val Val Ala Ala
                20                  25                  30

Ala Glu Lys Thr Lys Gln Gly Val Ala Glu Ala Gly Lys Thr Lys
            35                  40                  45

Glu Gly Val Leu Tyr Val Gly Ser Lys Thr Lys Glu Gly Val Val His
            50                  55                  60

Gly Val Ala Thr Val Ala Glu Lys Thr Lys Glu Gln Val Thr Asn Val
65                  70                  75                  80

Gly Gly Ala Val Val Thr Gly Val Thr Ala Val Ala Gln Lys Thr Val
                85                  90                  95

Glu Gly Ala Gly Ser Ile Ala Ala Ala Thr Gly Phe Val Lys Lys Asp
                100                 105                 110

Gln Leu Gly Lys Asn Glu Glu Gly Ala Pro Gln Glu Gly Ile Leu Glu
            115                 120                 125

Asp Met Pro Val Asp Pro Asp Asn Glu Ala Tyr Glu Met Pro Ser Glu
        130                 135                 140

Glu Gly Tyr Gln Asp Tyr Glu Pro Glu Ala
145                 150
```

ALPHA-SYNUCLEIN DETECTION USING BEADS

CROSS-REFERENCE TO RELATED APPLICATIONS

This application claims priority from U.S. Provisional Patent Application No. 62/895,535, filed on Sep. 4, 2019; U.S. Provisional Patent Application No. 63/040,144, filed on Jun. 17, 2020; U.S. Provisional Patent Application No. 63/042,679, filed on Jun. 23, 2020; U.S. Provisional Patent Application No. 63/045,593, filed on Jun. 29, 2020; U.S. Provisional Patent Application No. 63/073,420, filed on Sep. 1, 2020; and U.S. Provisional Patent Application No. 63/073,424, filed on Sep. 1, 2020, each of which is incorporated by reference herein in its entirety.

SEQUENCE LISTING

A Sequence Listing has been submitted electronically in ASCII format and is hereby incorporated by reference in its entirety. The ASCII copy, created on Sep. 2, 2020, is named Amprion-AS-FA-US-1_ST25.txt and is 26,468 bytes in size.

BACKGROUND

The accumulation and deposition of α-synuclein (α-syn or α-S) aggregates in brain tissue is the main event in the pathogenesis of different neurodegenerative disorders referred to as synucleinopathies. Synucleinopathies include Parkinson's disease (PD), Lewy Body Dementia (LBD), Multiple System Atrophy (MSA), and Pure Autonomic Failure (PAF). Current diagnosis of these disorders mainly relies on the recognition of clinical symptoms, which unfortunately typically provide a diagnosis only when the neurodegeneration is already in an advanced phase.

Various Protein Misfolding Cyclic Amplification (PMCA) assays provide an ultra-sensitive method for detecting misfolded aggregates through artificial acceleration and amplification of the misfolding and aggregation process in vitro. The basic concept of PMCA has been disclosed previously (Soto et al, WO 2002/04954; Estrada, et al. U.S. Pat. Pub. No. 20080118938). The PMCA assay has been used successfully to detect misfolded α-syn protein with very high sensitivity and specificity. See U.S. Pat. Pub. No. 2016/0077111, which is incorporated by reference herein in its entirety.

The PMCA assay represents an important advance over previous diagnostic methods. However, there remains a need for assay conditions that accelerate the amplification, yet avoid undesirable self-aggregation of protein monomers, as well as apparatuses to facilitate the use of such an assay.

SUMMARY

In one aspect, a method is provided for determining the presence of soluble, misfolded α-syn in a biological sample. The method includes contacting the biological sample with a monomeric α-syn protein and one or more beads having a mean diameter of from about 1.0 mm to about 5.0 mm to form an incubation mixture; incubating the incubation mixture to form a misfolded α-syn aggregate from the monomeric α-syn protein and the soluble, misfolded α-syn of the biological sample; de-aggregating at least a portion of the misfolded α-syn aggregate; repeating the steps of incubating and de-aggregating a number of times sufficient to amplify the soluble, misfolded α-syn of the sample to provide a detectable amount of misfolded α-syn aggregate; and determining if a detectable amount of misfolded α-syn aggregate is present in the biological sample; wherein detection of misfolded α-syn aggregate indicates the presence of soluble, misfolded α-syn in the biological sample.

In some aspects, the step of determining if a detectable amount of misfolded α-syn aggregate is present in the biological sample comprises contacting the incubation mixture with a protein aggregation indicator. An example of a suitable protein aggregation indicator is Thioflavin T (ThT). In further aspects, the method includes the step of obtaining the biological sample from a subject. In yet further aspects, the biological sample is a cerebrospinal fluid (CSF) sample. In additional aspects, the method includes determining the amount of the soluble, misfolded α-syn protein in the biological sample.

The incubation mixture includes one or more beads to accelerate the formation of misfolded α-syn aggregate. In some aspects, the beads comprise silicon nitride ($Si_3Ni_4$). In some aspects, the beads comprise borosilicate glass. In some aspects, the beads have a mean diameter ranging from about 1 mm to about 3.5 mm. In some aspects, the beads have a mean diameter ranging from greater than 2.3 mm to about 3.5 mm. In some aspects, the beads have a mean diameter of about 2.38 mm (3/32"), such as when the beads comprise $Si_3Ni_4$. In some aspects, the beads have a mean diameter of about 2.45 mm, such as when the beads comprise borosilicate glass. In some aspects, beads with a mean diameter of 2.3 mm or less are specifically excluded. In some aspects, glass beads with a mean diameter of 2.3 mm or less are specifically excluded. In some aspects, the incubation mixture is contained in a multi-well plate including a plurality of wells. In further aspects, each well of the multi-well plate includes a single bead. In further aspects, the surface of some or all of the beads are blocked with a protein, such as when the beads comprise $Si_3Ni_4$.

The use of beads allows the incubation conditions to be optimized to decrease the amount of self-aggregation of the monomeric α-syn protein, while accelerating the process. In some aspects, the monomeric α-syn protein of the incubation mixture has a concentration range of from about 10 μM to about 30 μM. In additional aspects, the incubation mixture includes one or more of Tris-HCL, IVIES, PIPES, MOPS, BES, TES, and HEPES and has a pH between about 6 and about 8, including between about 6.2 and about 6.5. In further aspects, the incubating of the incubation mixture is conducted at a temperature between about 35° C. and about 42° C. In yet further aspects, incubating the incubation mixture and de-aggregating at least a portion of the misfolded α-syn aggregate comprise an incubation cycle lasting from 0.3 to 1 hour. In additional aspects, de-aggregation is carried out by shaking (including by cyclic agitation), stirring, or sonication. In some aspects, the method also includes the step of concentrating the soluble, misfolded α-syn in the sample before incubating the sample using antibodies that specifically bind to soluble, misfolded α-syn.

Another aspect provides a method for diagnosing a disease associated with α-syn aggregation in a subject. The method includes contacting a biological sample with a monomeric α-syn protein and one or more beads having a mean diameter from about 1 mm to about 5 mm, from greater than 2.3 mm to about 5 mm, from greater than 3 mm to about 5 mm, about 2.38 mm, or about 2.45 mm to form an incubation mixture; incubating the incubation mixture to form a misfolded α-syn aggregate from the monomeric α-syn protein and the soluble, misfolded α-syn of the biological sample; de-aggregating at least a portion of the misfolded α-syn aggregate; repeating the steps of incubating and de-aggregating a number of times sufficient to amplify the soluble, misfolded α-syn of the biological sample to provide a detectable amount of misfolded α-syn aggregate; and determining if a detectable amount of misfolded α-syn aggregate is present in the biological sample, wherein detection of misfolded α-syn aggregate indicates that the biological subject has a disease associated with α-syn aggregation.

In some aspects, the disease associated with α-syn aggregation is PD. In other aspects, the disease associated with α-syn aggregation is LBD, MSA, or PAF. In further aspects, the method also includes treating a subject diagnosed as having a disease associated with α-syn aggregation with α-syn modulating therapy.

In another aspect, a kit for determining the presence of soluble, misfolded α-syn in a biological sample is provided. The kit includes a known amount of a monomeric α-syn protein; a known amount of a protein aggregation indicator; a container for incubating an incubation mixture; a buffer composition; one or more beads having a diameter from about 1 mm to about 5 mm, from greater than 2.3 mm to about 5 mm, from greater than 3 mm to about 5 mm, about 2.38 mm, or about 2.45 mm; instructions directing a user to carry out the method of detecting the presence of soluble misfolded α-syn in a biological sample described herein; and a package for holding the components of the kit. In some aspects, the container included in the kit comprises a multi-well plate including a plurality of wells.

The instructions direct the user to contact the biological sample with a known amount of the monomeric α-syn protein and the one or more beads in the container to form an incubation mixture; incubate the incubation mixture to form a misfolded α-syn aggregate from the monomeric α-syn protein and the soluble, misfolded α-syn of the biological sample; de-aggregate at least a portion of the misfolded α-syn aggregate; repeat the steps of incubating and de-aggregating a number of times sufficient to amplify the soluble, misfolded α-syn of the biological sample to provide a detectable amount of misfolded α-syn aggregate; and contact the incubation mixture with a known amount of a protein aggregation indicator to determine if a detectable amount of misfolded α-syn aggregate is present in the biological sample, wherein detection of misfolded α-syn aggregate indicates the presence of soluble, misfolded α-syn in the biological sample.

In another aspect, an apparatus is provided for biochemical assays such as, for example, enzyme-linked immunosorbent assays (ELISA) and PMCA. The apparatus is configured for use with beads and includes a tray. A horizontal upper surface of the tray has openings that are sized to receive the beads. The openings reach vertically through the tray. The upper surface is unobstructed to rolling movement of the beads across the upper surface between the openings and off the upper surface into the openings.

The apparatus further includes a gate. Openings reach vertically through the gate. Blocking portions of the gate are located between the openings. The gate is supported for movement horizontally between a first position and a second position. In the first position, the blocking portions of the gate are aligned vertically beneath the openings in the tray. In the second position, the openings in the gate are aligned vertically beneath the openings in the tray. This enables the beads to be dropped from the tray through the openings in the gate and further into bead receptacles, such as wells in an ELISA plate, by moving the gate from the first position to the second position.

Each opening in the tray may be sized to contain only a single one of the beads when the gate is in the first position. Additionally, the tray may have a vertical wall surrounding the upper surface. The vertical wall may have an outlet passage that is sized to permit beads to roll off the upper surface through the vertical wall. This enables excess beads to be removed from the tray when the desired number of beads have been rolled into the openings in the tray. Removing the excess beads allows the user to confirm by visual inspection that each one of the openings contains one bead.

The tray may be formed of transparent material such that the gate is visible through the tray. A color contrast between the beads and the gate can then help the user to visually confirm that a single bead is provided for each well. For example, a white gate that is visible though a transparent panel helps to display darkly hued beads (such as, for example, $Si_3N_4$ beads) more clearly.

BRIEF DESCRIPTION OF THE FIGURES

The claimed invention may be more readily understood by reference to the following figures, wherein:

FIG. 14A shows example results of using 2.38 mm $Si_3N_4$ beads blocked with BSA; the PD sample was positive around 75 h, while all three controls were negative. FIG. 14B shows example results of using unblocked 2 mm borosilicate glass beads; the PD sample was positive around 170 h, while all three controls were negative.

FIG. 16 is an exploded perspective view of a bead distribution apparatus.

FIG. 17 is top view of the apparatus of FIG. 16, showing parts in a position of use.

FIG. 18 is a view similar to FIG. 17, showing parts in a different position of use.

DETAILED DESCRIPTION

Methods and kits are provided for determining the presence of soluble, misfolded α-syn in a biological sample. The methods and kits comprise contacting the biological sample with a monomeric α-syn protein and one or more beads having a mean diameter from about 1 mm to about 5 mm, from greater than 2.3 mm to about 5 mm, from greater than 3 mm to about 5 mm, about 2.38 mm, or about 2.45 mm to form an incubation mixture; incubating the incubation mixture to form a misfolded α-syn aggregate from the monomeric α-syn protein and the soluble, misfolded α-syn of the biological sample; de-aggregating at least a portion of the misfolded α-syn aggregate; and repeating the steps of incubating and de-aggregating a number of times sufficient to amplify the soluble, misfolded α-syn of the biological sample to provide a detectable amount of misfolded α-syn aggregate. One can then determine if a detectable amount of misfolded α-syn aggregate is present in the biological sample, which indicates the presence of soluble, misfolded α-syn in the biological sample.

Figure 1:
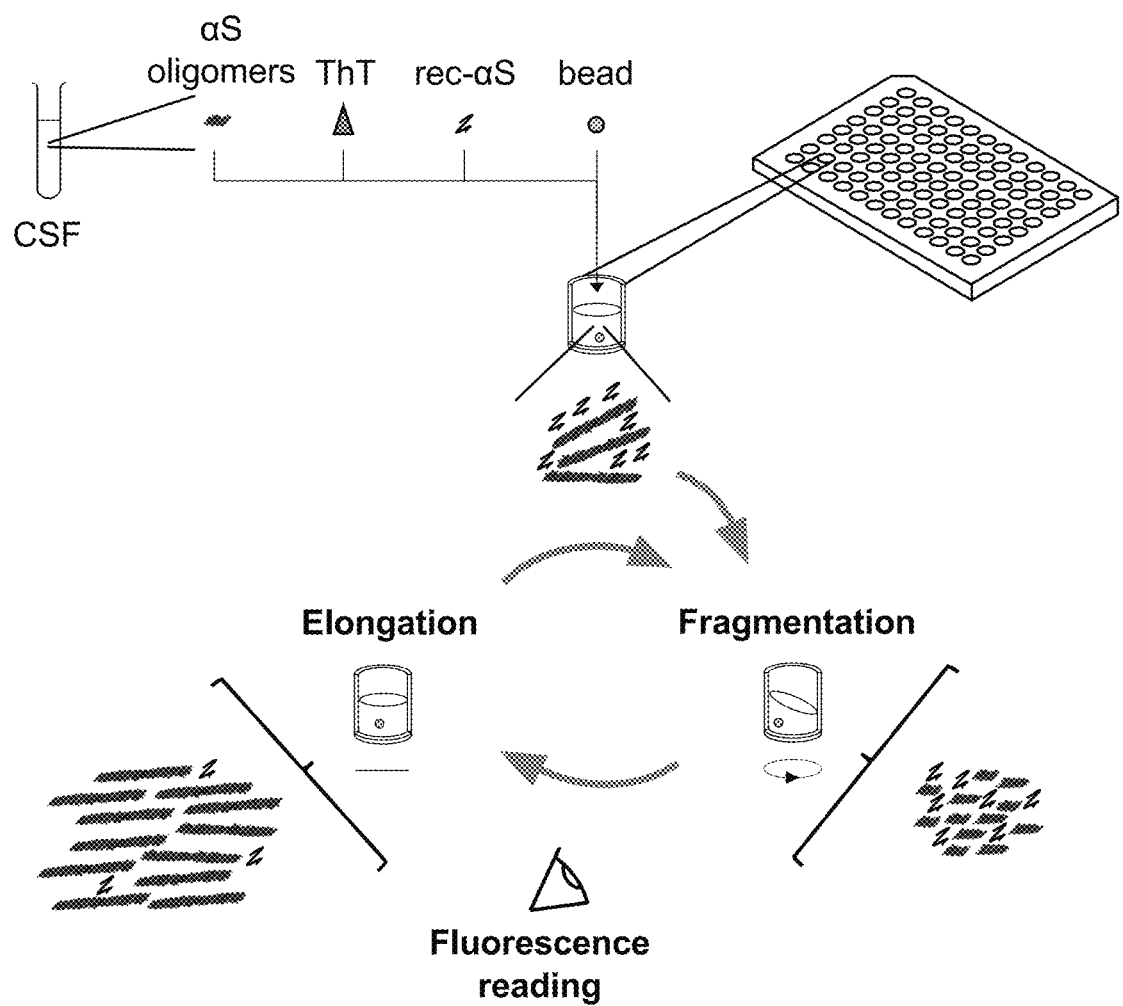
FIG. 1 is a schematic representation of the α-S PMCA technique disclosed and claimed herein for the detection of soluble, misfolded α-S protein.

In one illustrative example, depicted in the schematic explanation of FIG. 1, a method for determining the presence of soluble, misfolded α-syn protein in a biological sample is provided. The order of steps set forth below, in FIG. 1, and in the claims is provided for clarity only and should not be considered limiting. With that caveat, the method comprises: (A) contacting the biological sample with a pre-incubation mixture, the pre-incubation mixture comprising: (1) a monomeric α-syn protein; (2) a buffer composition; (3) a salt; and (4) an indicator, to form an incubation mixture; (B) conducting an incubation cycle on the incubation mixture, the incubation cycle being conducted: (1) two or more times on the incubation mixture effective to form an amplified portion of misfolded α-syn protein from the monomeric α-syn protein, each incubation cycle comprising: (i) incubating the incubation mixture effective to cause misfolding and/or aggregation of at least a portion of the monomeric α-syn protein in the presence of the soluble, misfolded α-syn protein; and (ii) physically disrupting the incubation mixture; (2) in the presence of either a $Si_3N_4$ bead or a borosilicate glass bead having a diameter of from about 1 mm to about 5 mm, from greater than 2.3 mm to about 5 mm, from greater than 3 mm to about 5 mm, about 2.38 mm, or about 2.45 mm; and (C) determining if a detectable amount of misfolded α-syn aggregate is present in the biological sample, wherein detection of misfolded α-syn aggregate indicates the presence of soluble, misfolded α-syn protein in the biological sample.

In some aspects of the method, the bead consists essentially of $Si_3N_4$ and has a diameter of about 2.38 mm. In some aspects, the method further comprises blocking the surface of the $Si_3N_4$ bead with BSA prior to the conducting. In some aspects, the blocking comprises soaking the $Si_3N_4$ bead in a solution of BSA in at least one of water and/or PIPES buffer. In some aspects, the bead consists essentially of borosilicate glass and has a diameter of about 2.45. In some aspects, the borosilicate glass is unblocked.

In some aspects of the method, the biological sample comprises human CSF. In some aspects, the monomeric α-syn protein comprises at least one of SEQ ID NO. 1, SEQ ID NO. 2, or a conservative variant thereof. In some aspects, the monomeric α-syn protein is present in a concentration of from about 10 µM to about 30 µM. In some aspects, the monomeric α-syn protein is present in a concentration of about 19.6 µM. In some aspects, the buffer composition has a pH between about 6.2 and about 6.5, including about 6.3. In some aspects, the buffer composition comprises PIPES. In some aspects, the buffer composition comprises about 100 mM PIPES, about 500 mM PIPES, about 600 mM PIPES, or about 700 mM PIPES. In some aspects, the salt comprises NaCl. In some aspects, the salt comprises NaCl in a concentration between about 500 mM and about 700 mM, including about 600 mM. In some aspects, the indicator comprises ThT. In some aspects, the detection comprises measuring ThT fluorescence at about 490 nm after excitation at about 440 nm. In some aspects, the indicator comprises ThT in a concentration of from about 5 µM to about 10 µM.

In some aspects, the physically disrupting comprises shaking, including orbital shaking.

Definitions

The term "diagnosis" can encompass determining the likelihood that a subject will develop a disease or the existence or nature of disease in a subject. The term diagnosis also encompasses determining the severity and probable outcome of disease or episode of disease or prospect of recovery, which is generally referred to as prognosis. "Diagnosis" can also encompass diagnosis in the context of rational therapy, in which the diagnosis guides therapy, including initial selection of therapy, modification of therapy (e.g., adjustment of dose or dosage regimen), and the like.

The term "prognosis" refers to a prediction of the probable course and outcome of a disease or the likelihood of recovery from a disease. Prognosis is distinguished from diagnosis in that it is generally already known that the subject has the disease, although prognosis and diagnosis can be carried out simultaneously. In the case of a prognosis for PD, the prognosis categorizes the relative severity of the PD, which can be used to guide selection of appropriate therapy.

The terms "treatment," "treating," and the like, refer to obtaining a desired pharmacologic or physiologic effect. The effect may be therapeutic in terms of a partial or complete cure for a disease or an adverse effect attributable to the disease. "Treatment" covers any treatment of a disease in a mammal, particularly in a human, and can include inhibiting the disease or condition, i.e., arresting its development; and relieving the disease, i.e., causing regression of the disease.

Prevention or prophylaxis refers to preventing the disease or a symptom of a disease from occurring in a subject who may be predisposed to the disease, but has not yet been diagnosed as having it (e.g., including diseases that may be associated with or caused by a primary disease). Prevention may include completely or partially preventing a disease or symptom.

The terms "therapeutically effective" and "pharmacologically effective" are intended to qualify the amount of an agent that will achieve the goal of improvement in disease severity and the frequency of incidence over treatment of each agent by itself, while avoiding adverse side effects typically associated with alternative therapies. The effectiveness of treatment may be measured by evaluating a reduction in the level of soluble, misfolded α-syn or a decrease in other symptoms associated with a particular synucleinopathy.

Where a range of values is provided, it is understood that each intervening value, to the tenth of the unit of the lower limit unless the context clearly dictates otherwise, between the upper and lower limit of that range, and any other stated or intervening value in that stated range, is encompassed. The upper and lower limits of these smaller ranges may independently be included in the smaller ranges and are also encompassed, subject to any specifically excluded limit in the stated range. Where the stated range includes one or both of the limits, ranges excluding either or both of those included limits are also included.

Unless defined otherwise, all technical and scientific terms have the same meaning as commonly understood by one of ordinary skill in the art to which this invention belongs.

The term "about" in conjunction with a number is intended to include ±10% of the number. This is true whether "about" is modifying a stand-alone number or modifying a number at either or both ends of a range of numbers. In other words, "about 10" means from 9 to 11. Likewise, "about 10 to about 20" means 9 to 22. In the absence of the term "about," the exact number is intended. In other words, "10" means 10.

The singular forms "a", "and", and "the" include plural referents unless the context clearly dictates otherwise. Thus, for example, reference to "a sample" includes one sample and includes a plurality of such samples. Likewise, reference to "the monomeric α-syn protein" includes reference to one or more protein molecules, and so forth.

Determining the Presence of Soluble, Misfolded α-Syn Protein in a Biological Sample A method is provided for determining the presence of soluble, misfolded α-syn protein in a biological sample. In some aspects, determining the presence includes detecting whether soluble, misfolded α-syn protein is present in the sample, while in other aspects determining the presence includes determining the amount of soluble, misfolded α-syn protein in the sample. The method includes the steps of contacting the biological sample with a monomeric α-syn protein and one or more beads having a mean diameter from about 1 mm to about 5 mm, from greater than 2.3 mm to about 5 mm, from greater than 3 mm to about 5 mm, about 2.38 mm, or about 2.45 mm to form an incubation mixture; incubating the incubation mixture to form a misfolded α-syn aggregate from the monomeric α-syn protein and the soluble, misfolded α-syn of the biological sample; and de-aggregating at least a portion of the misfolded α-syn aggregate. The steps of incubating and de-aggregating the incubation mixture are repeated a number of times sufficient to amplify the soluble, misfolded α-syn protein of the sample to provide a detectable amount of misfolded α-syn aggregate. The method then involves determining if a detectable amount of misfolded α-syn aggregate is present in the biological sample. Detection of misfolded α-syn aggregate indicates the presence of soluble, misfolded α-syn protein in the biological sample.

As used herein, "α-S," "α-syn," or "α-synuclein," as in a soluble, misfolded α-syn protein, may refer to the full-length, 140 amino acid wild-type α-syn protein, i.e., "αS-140." Other isoforms or fragments may include "αS-126," alpha-syn-126, which lacks residues 41-54, e.g., due to loss of exon 3; and "αS-112" alpha-syn-112, which lacks residue 103-130, e.g., due to loss of exon 5. Various aS isoforms may include and are not limited to αS-140, αS-126, and αS-112. Various α-syn peptides may be associated with neuronal damage associated with a synucleinopathy such as PD.

"Soluble, misfolded α-syn protein" refers to misfolded monomers or aggregates of α-syn protein that remain in solution. Examples of soluble, misfolded α-syn protein may include any number of aggregated misfolded α-syn protein monomers so long as the misfolded α-syn protein remains soluble. For example, soluble, misfolded α-syn protein may include aggregates of between 2 and about 50 units of misfolded α-syn protein monomer. In some examples, aggregates may be referred to as oligomers or polymers. In some examples, aggregation may be referred to as oligomerization or polymerization.

Soluble, misfolded α-syn protein may aggregate or oligomerize to form insoluble aggregates and/or higher oligomers, leading to misfolded α-syn protein aggregates in the form of protofibrils, fibrils, and eventually plaques or inclusion bodies. Nucleation-dependent polymerization may typically be characterized by a slow lag phase wherein aggregated nuclei may form, which may then stimulate the rapid formation of further and/or larger aggregates. The lag phase may be minimized or removed by addition of pre-formed "nuclei" or "seeds." "Seeds" or "nuclei" refer to misfolded α-syn protein or short fragmented fibrils, particularly soluble, misfolded α-syn protein, with the ability to induce further misfolding, oligomerization, and/or aggregation. In some examples, "seeds" or "nuclei" may exclude un-aggregated monomers of α-syn protein. Without wishing to be bound by theory, it is believed that at least under some conditions, monomeric α-syn protein may not be stable, and the minimum stable size of pathogenic, misfolded α-syn protein may be an aggregate of two monomer units of misfolded α-syn protein.

As used herein, "soluble" species, including soluble misfolded α-syn, may form a solution in biological fluids under physiological conditions, whereas "insoluble" species may be present as precipitates, fibrils, deposits, tangles, or other non-dissolved forms in such biological fluids. Examples of insoluble species include fibrils of Aβ, α-S, tau, and the like. A species that dissolves in a non-biological fluid but not a biological fluid under physiological conditions may be considered insoluble. For example, fibrils of α-syn and the like may be dissolved in a solution of, e.g., a surfactant such as sodium dodecyl sulfate (SDS) in water, but may still be insoluble in one or more of the mentioned biological fluids under physiological conditions and are, therefore, considered insoluble herein.

In some aspects, the biological sample may exclude insoluble species of the misfolded protein as a precipitate, fibril, deposit, tangle, plaque, or other form that may be insoluble in one or more of the described biological fluids under physiological conditions. The sample may exclude the misfolded α-syn protein in insoluble form, e.g., the biological sample may exclude the misfolded α-syn protein as a precipitate, fibril, deposit, tangle, plaque, or other insoluble form, e.g., in fibril form.

As used herein, a "misfolded protein" is a protein that no longer contains all or part of the structural conformation of the protein as it exists in its typical, nonpathogenic normal function within a biological system. A misfolded protein may aggregate. A misfolded protein may localize in a protein aggregate. A misfolded protein may be a non-functional protein. A misfolded protein may be a pathogenic conformer of the protein. Monomeric α-syn protein compositions may be provided in native, nonpathogenic confirmations without the catalytic activity for misfolding, oligomerization, and aggregation associated with seeds. Monomeric α-syn protein compositions may be provided in seed-free form.

The phrases "monomeric α-syn protein" and "monomeric α-syn substrate" are used interchangeably and refer to one or more α-syn protein molecules in their native, nonpathogenic configuration. In some aspects, the monomeric α-syn protein comprises, consists essentially of, or consists of wildtype or recombinant human α-syn protein having 140 amino acids, having a molecular mass of 14,460 Da, and being represented by the sequence:

```
SEQ ID NO. 1:
MDVFMKGLSK AKEGVVAAAE KTKQGVAEAA GKTKEGVLYV

GSKTKEGVVH GVATVAEKTK EQVTNVGGAV VTGVTAVAQK

TVEGAGSIAA ATGFVKKDQL GKNEEGAPQE GILEDMPVDP

DNEAYEMPSE EGYQDYEPEA
```

In some aspects, the monomeric α-syn protein comprises, consists essentially of, or consists of a conservative variant of SEQ ID NO. 1. A conservative variant may be a peptide or amino acid sequence that deviates from SEQ ID NO. 1 only in the substitution of one or several amino acids for amino acids having similar biochemical properties and having a minimal or beneficial impact on the activity of the resultant protein in the PMCA assay. A conservative variant must functionally perform substantially like the base component, i.e., SEQ ID NO. 1. For example, a conservative variant of SEQ ID NO. 1 will aggregate with misfolded α-syn and will form aggregates with substantially similar reaction kinetics under similar reaction conditions. The conservative variant may have for example, one, two, three, four, five, six, seven (5%), and up to 14 (10%) substitutions in the amino acid sequence.

In some aspects, the monomeric α-syn protein comprises a recombinant α-syn protein comprising six additional histidine amino acids (i.e., a polyHis purification tag) on the C-terminus of SEQ ID NO. 1, resulting in a molecular mass of 15,283 Da and being represented by the sequence:

SEQ ID NO. 2:
MDVFMKGLSK AKEGVVAAAE KTKQGVAEAA GKTKEGVLYV
GSKTKEGVVH GVATVAEKTK EQVTNVGGAV VTGVTAVAQK
TVEGAGSIAA ATGFVKKDQL GKNEEGAPQE GILEDMPVDP
DNEAYEMPSE EGYQDYEPEA HHHHHH

Thus, SEQ ID NO. 2 is distinguishable from SEQ ID NO. 1 by the six additional histidine amino acids on the C-terminus. SEQ ID NO. 2 is further distinguishable from, e.g., a variant of SEQ ID NO. 1 wherein one or more amino acids are added to the N-terminus. In some aspects, variants of SEQ ID NO. 1 wherein one or more amino acids are added to the N-terminus are excluded. However, some aspects include N-terminus additions. Thus:

SEQ ID NO. 3:
HHHHHH MDVFMKGLSK AKEGVVAAAE KTKQGVAEAA
GKTKEGVLYV GSKTKEGVVH GVATVAEKTK EQVTNVGGAV
VTGVTAVAQK TVEGAGSIAA ATGFVKKDQL GKNEEGAPQE
GILEDMPVDP DNEAYEMPSE EGYQDYEPEA

Additional purification tags are contemplated, including, e.g., FLAG, HA, Myc, and V5, thus generating the following SEQ ID Nos.:

SEQ ID NO. 4:
MDVFMKGLSK AKEGVVAAAE KTKQGVAEAA GKTKEGVLYV
GSKTKEGVVH GVATVAEKTK EQVTNVGGAV VTGVTAVAQK
TVEGAGSIAA ATGFVKKDQL GKNEEGAPQE GILEDMPVDP
DNEAYEMPSE EGYQDYEPEA DYKDDDD

SEQ ID NO. 5:
DYKDDDD MDVFMKGLSK AKEGVVAAAE KTKQGVAEAA
GKTKEGVLYV GSKTKEGVVH GVATVAEKTK EQVTNVGGAV
VTGVTAVAQK TVEGAGSIAA ATGFVKKDQL GKNEEGAPQE
GILEDMPVDP DNEAYEMPSE EGYQDYEPEA

-continued

SEQ ID NO. 6:
MDVFMKGLSK AKEGVVAAAE KTKQGVAEAA GKTKEGVLYV
GSKTKEGVVH GVATVAEKTK EQVTNVGGAV VTGVTAVAQK
TVEGAGSIAA ATGFVKKDQL GKNEEGAPQE GILEDMPVDP
DNEAYEMPSE EGYQDYEPEA DYKDDDDK

SEQ ID NO. 7:
DYKDDDDK MDVFMKGLSK AKEGVVAAAE KTKQGVAEAA
GKTKEGVLYV GSKTKEGVVH GVATVAEKTK EQVTNVGGAV
VTGVTAVAQK TVEGAGSIAA ATGFVKKDQL GKNEEGAPQE
GILEDMPVDP DNEAYEMPSE EGYQDYEPEA

SEQ ID NO. 8:
MDVFMKGLSK AKEGVVAAAE KTKQGVAEAA GKTKEGVLYV
GSKTKEGVVH GVATVAEKTK EQVTNVGGAV VTGVTAVAQK
TVEGAGSIAA ATGFVKKDQL GKNEEGAPQE GILEDMPVDP
DNEAYEMPSE EGYQDYEPEA DYKDDDK

SEQ ID NO. 9:
DYKDDDK MDVFMKGLSK AKEGVVAAAE KTKQGVAEAA
GKTKEGVLYV GSKTKEGVVH GVATVAEKTK EQVTNVGGAV
VTGVTAVAQK TVEGAGSIAA ATGFVKKDQL GKNEEGAPQE
GILEDMPVDP DNEAYEMPSE EGYQDYEPEA

SEQ ID NO. 10:
MDVFMKGLSK AKEGVVAAAE KTKQGVAEAA GKTKEGVLYV
GSKTKEGVVH GVATVAEKTK EQVTNVGGAV VTGVTAVAQK
TVEGAGSIAA ATGFVKKDQL GKNEEGAPQE GILEDMPVDP
DNEAYEMPSE EGYQDYEPEA YPYDVPDYA

SEQ ID NO. 11:
YPYDVPDYA MDVFMKGLSK AKEGVVAAAE KTKQGVAEAA
GKTKEGVLYV GSKTKEGVVH GVATVAEKTK EQVTNVGGAV
VTGVTAVAQK TVEGAGSIAA ATGFVKKDQL GKNEEGAPQE
GILEDMPVDP DNEAYEMPSE EGYQDYEPEA

SEQ ID NO. 12:
MDVFMKGLSK AKEGVVAAAE KTKQGVAEAA GKTKEGVLYV
GSKTKEGVVH GVATVAEKTK EQVTNVGGAV VTGVTAVAQK
TVEGAGSIAA ATGFVKKDQL GKNEEGAPQE GILEDMPVDP
DNEAYEMPSE EGYQDYEPEA YAYDVPDYA

SEQ ID NO. 13:
YAYDVPDYA MDVFMKGLSK AKEGVVAAAE KTKQGVAEAA
GKTKEGVLYV GSKTKEGVVH GVATVAEKTK EQVTNVGGAV
VTGVTAVAQK TVEGAGSIAA ATGFVKKDQL GKNEEGAPQE
GILEDMPVDP DNEAYEMPSE EGYQDYEPEA

SEQ ID NO. 14:
MDVFMKGLSK AKEGVVAAAE KTKQGVAEAA GKTKEGVLYV
GSKTKEGVVH GVATVAEKTK EQVTNVGGAV VTGVTAVAQK
TVEGAGSIAA ATGFVKKDQL GKNEEGAPQE GILEDMPVDP
DNEAYEMPSE EGYQDYEPEA YDVPDYASL

-continued

SEQ ID NO. 15:
YDVPDYASL MDVFMKGLSK AKEGVVAAAE KTKQGVAEAA

GKTKEGVLYV GSKTKEGVVH GVATVAEKTK EQVTNVGGAV

VTGVTAVAQK TVEGAGSIAA ATGFVKKDQL GKNEEGAPQE

GILEDMPVDP DNEAYEMPSE EGYQDYEPEA

SEQ ID NO. 16:
MDVFMKGLSK AKEGVVAAAE KTKQGVAEAA GKTKEGVLYV

GSKTKEGVVH GVATVAEKTK EQVTNVGGAV VTGVTAVAQK

TVEGAGSIAA ATGFVKKDQL GKNEEGAPQE GILEDMPVDP

DNEAYEMPSE EGYQDYEPEA EQKLISEEDL

SEQ ID NO. 17:
EQKLISEEDL MDVFMKGLSK AKEGVVAAAE KTKQGVAEAA

GKTKEGVLYV GSKTKEGVVH GVATVAEKTK EQVTNVGGAV

VTGVTAVAQK TVEGAGSIAA ATGFVKKDQL GKNEEGAPQE

GILEDMPVDP DNEAYEMPSE EGYQDYEPEA

SEQ ID NO. 18:
MDVFMKGLSK AKEGVVAAAE KTKQGVAEAA GKTKEGVLYV

GSKTKEGVVH GVATVAEKTK EQVTNVGGAV VTGVTAVAQK

TVEGAGSIAA ATGFVKKDQL GKNEEGAPQE GILEDMPVDP

DNEAYEMPSE EGYQDYEPEA GKPIPNPLLGLDST

SEQ ID NO. 19:
GKPIPNPLLGLDST MDVFMKGLSK AKEGVVAAAE KTKQGVAEAA

GKTKEGVLYV GSKTKEGVVH GVATVAEKTK EQVTNVGGAV

VTGVTAVAQK TVEGAGSIAA ATGFVKKDQL GKNEEGAPQE

GILEDMPVDP DNEAYEMPSE EGYQDYEPEA

In some aspects, the method may include providing the monomeric α-syn protein in labeled form. A labeled monomeric α-syn protein may be considered a conservative variant. The monomeric α-syn protein in labeled form may include one or more of: a covalently incorporated radioactive amino acid, a covalently incorporated, isotopically labeled amino acid, a covalently incorporated fluorophore, and the like. Thus, detection of the soluble, misfolded α-syn protein may include detecting the monomeric α-syn protein in labeled form as incorporated into the amplified portion of misfolded α-syn protein.

Incubation Conditions

The methods include contacting the biological sample with a monomeric α-syn protein and one or more beads having a mean diameter from 1 mm to 5 mm, from greater than 2.3 mm to 5 mm, from greater than 3 mm to 5 mm, 2.38 mm, or 2.45 mm to form an incubation mixture, and incubating the incubation mixture to form a misfolded α-syn aggregate from the monomeric α-syn protein and the soluble, misfolded α-syn of the biological sample. "Contacting," as used herein, refers to putting the various agents in proximity and under conditions in which they can interact so that the desired effect can occur. For example, contacting the biological sample with monomeric α-syn protein allows the monomeric α-syn protein to interact with any soluble misfolded α-syn protein present in the biological sample thereby stimulating aggregation of the monomeric α-syn protein.

Incubation conditions to form a misfolded α-syn aggregate include a variety of variable factors, such as the type and number of beads, the identity and concentration of the monomeric α-syn protein, the type of container used to conduct the incubation, the temperature, pH, buffer composition, salt concentration or ionic strength, and other characteristics of the liquid medium used for the incubation. Including beads in the incubation mixture allows the incubation to occur under faster conditions that also avoid self-aggregation by the monomeric α-syn protein.

The incubation mixture can include various different concentrations of the monomeric α-syn protein. Including beads can reduce the concentration of monomeric α-syn protein substrate required in order to carry out the PMCA assay. In some aspects, the incubation mixture may include the monomeric α-syn protein in a concentration, or in a concentration range: between about 500 nM and about 500 µM; between about 1 µM and about 200 µM; between about 5 µM to about 100 µM; between about 10 µM and about 50 µM; about 65 µM; between about 10 µM and about 30 µM; greater than 10 µM and less than 30 µM; about 20 µM; about 19.6 µM; or 19.6 µM.

The incubation mixture can include various buffer compositions. The buffer composition is effective to maintain the pH of the incubation mixture in a range from about pH 5 to about pH 9, from about pH 6 to about pH 8, from about pH 6 to about pH 7, from about pH 7 to about pH 8, about pH 7, about pH 7.4, from about pH 6.2 to about pH 6.5, including pH 6.3, 6.4, and 6.5. In some aspects, the incubation mixture comprises one or more of the buffers Tris-HCL, IVIES, PIPES, MOPS, BES, TES, and HEPES. In some aspects, the incubation buffer comprises PIPES in a concentration of about 100 mM, about 500 mM, about 600 mM, and about 700 mM.

In some aspects, the incubation mixture comprises salt in a given concentration. The salt may, for example, enhance signal to noise ratio in fluorescence detection. In one aspect, the salt comprises NaCl. Other suitable salts may include KCl. In one aspect, the salt, e.g., NaCl, may be present in a concentration of about 50 mM to about 1,000 mM, about 50 mM to about 500 mM, about 50 to about 150 mM, about 150 mM to about 500 mM, about 50 mM, about 150 mM, about 300 mM, about 500 mM, about 600 mM, or about 700 mM. In one aspect, the salt, e.g., NaCl, is present in a concentration of about 500 mM.

In one aspect, the incubation mixture excludes surfactants or detergents, such as, for example, SDS.

A variety of temperatures are suitable for carrying out the incubation cycles. The temperature of the incubation mixture, in each incubation cycle, at a temperature in ° C., can independently be about 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or a range between any two of the preceding values, for example, between about 15° C. and about 50° C., or between about 25° C. and about 45° C., or between about 30° C. and about 42° C. In some aspects, the incubation is carried out at about normal physiological temperatures for a warm-blooded animal. In further aspects, incubating the incubation mixture is conducted at a temperature between about 35° C. and about 40° C. or between about 37° C. and about 42° C.

The incubation mixture includes one or more beads. Beads are small, typically spherical objects such as high-density beads having a low friction surface that are commonly used as bearing beads. Including beads in the incubation mixture increases the rate of formation of misfolded α-syn aggregate from the monomeric α-syn protein and the soluble, misfolded α-syn of the biological sample. These beads should be distinguished from antibody coated magnetic or paramagnetic beads or particles (e.g., Dynabeads) used in concentration and/or immune depletion steps, which are known. See, e.g., U.S. Pat. Pub. No. 2016/0077111.

The beads can be formed from a variety of biologically inert materials. In some aspects, the beads are formed of a synthetic or natural polymer, while in other aspects the beads are formed from a mineral, ceramic, glass, or metal. The beads can be homogenous, or they can include a core made from a different material. Examples of synthetic polymers include acrylic polymers, polyamides, polyimides, polyesters, polyethers, polymeric vinyl compounds, polyalkenes, and substituted derivatives thereof, as well as copolymers comprising more than one such polymer. Examples of specific synthetic polymers include polystyrene, polytetrafluoroethylene, and polymethylmethacrylate. Examples of natural polymers include carbohydrate-based polymers such as agarose.

In some aspects, the polymer comprises a non-polymeric material such as a mineral, ceramic, glass, or metal. More specific examples of non-polymeric materials for the bead include zirconium oxide, silica/zirconium, silica, glass, borosilicate glass, quartz, steel, titanium, tungsten carbide, silicon carbide, and $Si_3N_4$. In some aspects, it may be suitable to use a material that has a darker hue, such as $Si_3N_4$, to reduce the background fluorescence present in an assay.

In some aspects, the beads comprise, consist essentially of, or consist of $Si_3N_4$. In some aspects, the beads comprise, consist essentially of, or consist of borosilicate glass. In one aspect, zirconium/silica beads are excluded. In one aspect, glass beads other than borosilicate glass beads are excluded. In one aspect, steel beads are excluded. In one aspect, polystyrene beads are excluded.

The size of the bead may have a significant effect on its ability to increase the rate of protein aggregation. In some embodiments, the beads included in the incubation mixture may have a mean diameter of greater than 0.5 mm. In some aspects, the beads have a mean diameter from greater than 0.5 to about 10 mm. In some aspects, the beads have a mean diameter from greater than 0.5 mm to about 5 mm. In further aspects, the beads have a mean diameter ranging from greater than 0.5 mm to about 3.5 mm. In some aspects, the beads have a mean diameter from about 1.0 to about 10 mm, while in additional aspects the beads have a mean diameter from about 1.0 mm to about 5 mm. In further aspects, the beads have a mean diameter ranging from greater than 1.0 mm to about 3.5 mm. In some aspects, the beads have a mean diameter from 2.38 to about 10 mm, while in additional aspects the beads have a mean diameter from 2.38 mm to about 5 mm. In further aspects, the beads have a mean diameter ranging from greater than or equal to about 2.3 mm to about 3.5 mm, from about 2.38 to about 3.5 mm, or from about 2.45 mm to about 3.5 mm. In further aspects, the beads may have a mean diameter from about 1 mm to about 5 mm, from greater than 2.3 mm to about 5 mm, from greater than 3 mm to about 5 mm, about 2.38 mm, or about 2.45 mm. In some aspects, the beads comprise, consist essentially of, or consist of $Si_3N_4$, have a mean diameter of 2.38 mm, and are blocked with BSA. In some aspects, the beads comprise, consist essentially of, or consist of borosilicate glass, have a mean diameter of 2.45 mm, and are unblocked. In some aspects, beads having a mean diameter of 2.3 mm or less are excluded from the invention. In some aspects, glass beads having a mean diameter of 2.3 mm or less are excluded from the invention. In some aspects, glass beads having a mean diameter of 3 mm or less are excluded from the invention. The size distribution of the beads is defined so that more than 90% of the beads are found between 80-120% of the mean bead diameter, or between 90-110% of the mean bead diameter.

The number of beads included in the incubation mixture can vary depending on the size of the incubation mixture. In some aspects, the incubation mixture includes a plurality of beads. In some aspects, the incubation includes one bead per 200 μL of incubation mixture. In further aspects, the incubation mixture includes from 1 to 10, 1 to 20, 1 to 100, 5 to 50, 20 to 100, or 50 to 500 beads. In some aspects, the incubation mixture includes a single bead.

In some aspects, the surface of the one or more beads is "blocked" with a protein. Blocking the surface of the bead with a protein refers to providing a coating or layer over all or a substantial portion of the surface of the bead. Any suitable biocompatible protein can be used to coat the surface of the bead. A suitable protein for use in blocking the surface of the bead is an albumin, such as BSA. Other suitable blocking proteins may include casein or milk powder. The one or more beads can be blocked by soaking the one or more beads in a solution including the protein. The solution can be a water solution and/or a buffered solution such as PIPES, Tris-HCl, MES, MOPS, BES, TES, and HEPES.

The incubation mixture is held within a suitably sized container, such as a test tube. Suitable sterile incubation containers are known to those skilled in the art. In some aspects, the incubation mixture is contained in a multi-well plate including a plurality of wells. For example, the multi-well plate can include 96 wells. The wells of the multi-well plate can have a volume from 100 to 1000 μL, from 150 to 750 μL, or from 200 to 350 μL. In one aspect, such as when the beads are $Si_3N_4$ beads, the container is a black bottom 96-well plate (Costar 3916). In one aspect, such as when the beads are borosilicate glass beads, the container is a clear bottom 96-well plate (Costar 3603).

Figure 21:
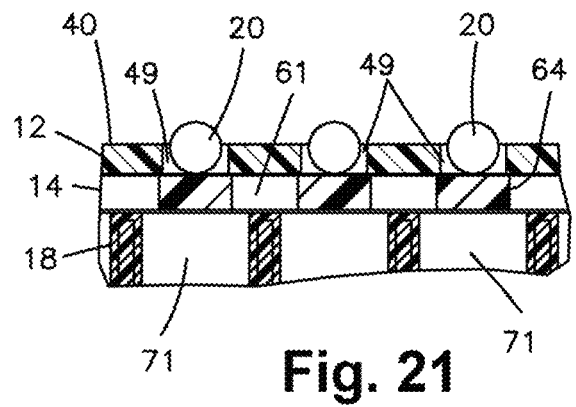
FIGS. 21-23 are partial sectional views similar to FIG. 20, showing parts of the apparatus in successive steps of use.
Figure 22:
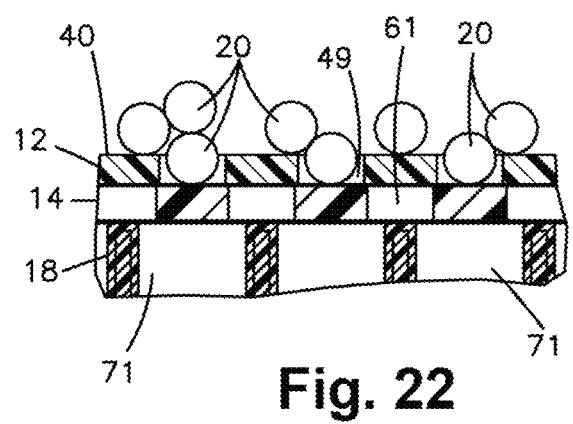
Figure 23:
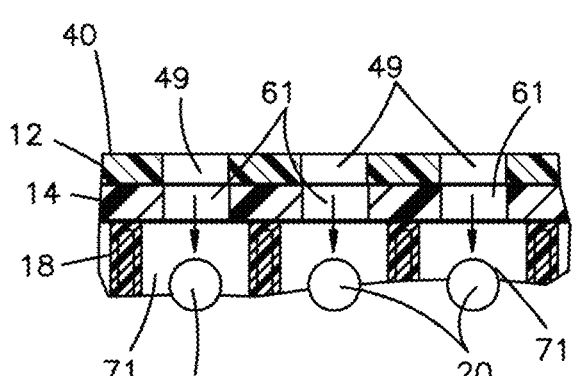

In some aspects, each well of the multi-well plate includes a single bead. In one such aspect, the multi-well plate may be used in conjunction with a bead distribution apparatus, such as bead distribution apparatus 10 shown in FIG. 16. Apparatus 10 can be used in any assay that is performed with beads in a multi-well plate, such as for example, an ELISA or in a PMCA assay such as those described and/or claimed herein. In the illustrated example, the apparatus 10 includes a tray 12, a gate 14, and a receptacle plate 18. The gate 14 is movable relative to the tray 12 and the receptacle plate 18 as indicated in FIG. 17 and FIG. 18. This enables spherical beads 20, e.g., $Si_3N_4$ beads having a mean diameter greater than 2.3 mm, to be loaded into the tray 12 and distributed individually into the receptacle plate 18, as shown in FIGS. 21-23.

The tray 12 in the illustrated example is generally rectangular with opposite sides 30, 32 reaching lengthwise between opposite ends 34, 36. The sides 30, 32 and ends 34, 36 of the tray 12 are defined by corresponding sections of a peripheral wall 40. A panel 42 reaches throughout the length and width of the tray 12 within the surrounding peripheral wall 40. The panel 42 has a horizontal upper surface 46 with an array of bead openings 49. The bead openings 49 reach through the panel 42. In the given example, there are ninety-six bead openings 49 in an eight by twelve array of parallel rows and columns, as viewed in FIGS. 17 and 18. A bead outlet 51 reaches through a corner of the peripheral wall 40. A slot 53 reaches through the first end section 34 of the peripheral wall 40.

The gate 14 is configured as a rectangular card. Slots 61 reach through the gate 14 and are arranged to coincide with the rows of bead openings 49 in the tray 12. Accordingly, the illustrated example has twelve parallel slots 61 reaching across the gate 14. The slots 61 are spaced apart by blocking portions 64 of the gate 14, each of which is located between a pair of adjacent slots 61.

The receptacle plate 18 has an array of wells 71 corresponding to the array of bead openings in the tray 12. In this example, the receptacle plate 18 is a standard ninety-six well ELISA plate with a known configuration in which the wells 71 are arranged in an eight by twelve array.

Figure 19:
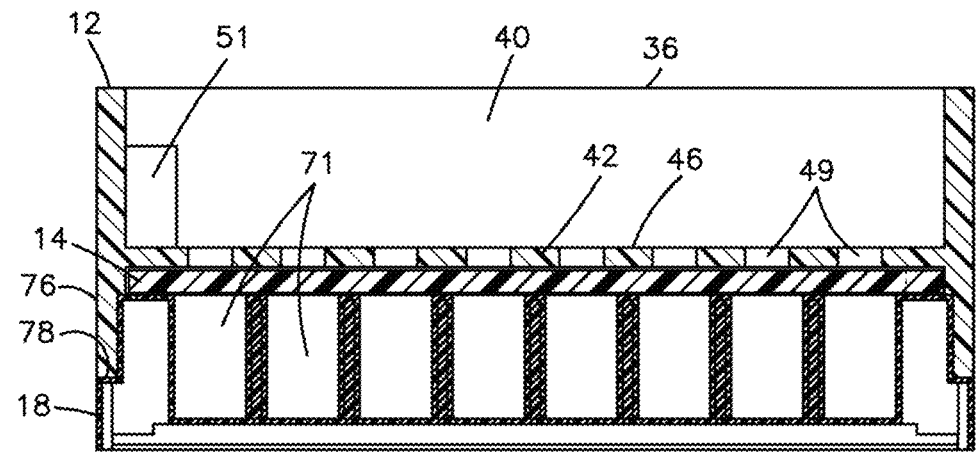
FIG. 19 is a sectional view taken on line 4-4 of FIG. 17.

In use, the tray 12 is placed over the receptacle plate 18 as shown in FIG. 19. The bead openings 49 in the tray 12 are then aligned vertically over the wells 71 in the receptacle plate 18. A lower skirt portion 76 of the peripheral wall 40 rests on a shoulder portion 78 of the receptacle plate 18. The skirt 76 supports the tray 12 in a position in which the panel 42 is spaced upward from the receptacle plate 18. This provides space for the gate 14 to be inserted through the slot 53 in the first end section 34 of the peripheral wall 40. The inserted gate 14 is interposed vertically between the panel 42 and the receptacle plate 18. The user can slide the gate 14 inward and outward of the slot 53 to move the gate 14 back and forth between the positions of FIGS. 17 and 18. The panel 42 may be formed of a transparent material so that the gate 14 can be viewed through the panel 42 as shown in FIGS. 17 and 18.

Figure 20:
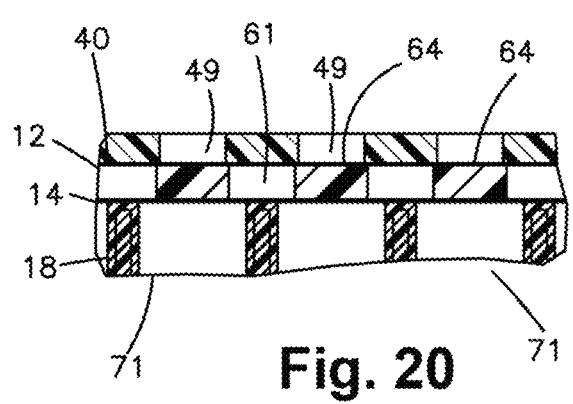
FIG. 20 is a sectional view taken partially on line 5-5 of FIG. 17.

When the gate is in the position of FIG. 17, each blocking portion 64 of the gate 14 is located beneath a corresponding row of bead openings 49 in the tray 12, as shown in FIG. 20. The user can pour an indeterminate number of coated beads 20 onto the tray 12 so that the beads 20 roll freely across the upper surface 46 of the panel 42 between the openings 49, with some of the beads 20 rolling off the upper surface 46 and into the openings 49, as shown in FIG. 21. In the illustrated example, each bead opening 49 is sized to receive only a single bead 20. The user can then lift and tilt the tray 12 to roll the excess beads 20 off the upper surface 46 through the outlet passage 51 in the peripheral wall 40. The tray 12 is thus loaded with beads 20 as shown in FIG. 22. When the user slides the gate 14 inward to the position of FIG. 18, the slots 61 in the gate 14 are moved beneath the openings 49 in the tray 12, as shown in FIG. 23. The beads 20 then drop from the openings 49 through the slots 61 and into the wells 71, with each well 71 receiving only a single bead 20.

Removing excess beads through the outlet opening 51 helps to ensure that only a single bead 20 will be dropped into each well 71 when the gate 14 is moved to the position of FIGS. 18 and 23. A transparent tray panel 42 with a color contrast between the beads 20 and the gate 14 also helps to ensure deposition of only a single bead 20. For example, the apparatus 10 may include a white gate 14 that is visible though a transparent panel 42 to display darkly hued beads 20 more clearly.

Once the beads are in place, the incubation mixture is incubated for a sufficient period of time to form a misfolded α-syn aggregate from the monomeric α-syn protein and the soluble, misfolded α-syn of the biological sample. After incubating the incubation mixture to form a misfolded α-syn aggregate, at least a portion of the incubation mixture is de-aggregated, before the cycle is repeated.

As used herein, aggregates of misfolded α-syn protein refer to non-covalent associations of protein including soluble, misfolded α-syn protein. Aggregates of misfolded α-syn protein may be "de-aggregated," broken up, or disrupted to release smaller fragments or aggregates, e.g., soluble, misfolded α-syn protein and fragmented fibrils. The catalytic activity of a collection of misfolded α-syn protein aggregate seeds may scale, at least in part with the number of seeds in a mixture. Accordingly, disruption of aggregates of misfolded α-syn protein in a mixture to release soluble, misfolded α-syn protein and fragmented fibrils seeds may lead to an increase in catalytic activity for aggregation of monomeric α-syn protein.

In several aspects, de-aggregating the incubation mixture may include one or more types of physical disruption selected from: shaking, sonication, stirring, freezing/thawing, laser irradiation, autoclave incubation, high pressure, homogenization, and the like. Shaking may include cyclic agitation, such as orbital agitation. The cyclic agitation may be conducted between about 50 rotations per minute (RPM) and 10,000 RPM. The cyclic agitation may be conducted between about 200 RPM and about 2000 RPM. The cyclic agitation may be conducted at about 600-800 RPM. De-aggregation of the incubation mixture may be conducted once after each incubation cycle for between about 5 seconds and about 10 minutes, between about 30 sec and about 1 minute, between about 45 sec and about 1 minute, for about 1 minute, and the like.

The steps of incubating and de-aggregating the incubation mixture are repeated a number of times sufficient to amplify the soluble, misfolded α-syn of the sample to provide a detectable amount of misfolded α-syn aggregate. The two steps of incubating the incubation mixture and then de-aggregating the incubation mixture are referred to herein as the incubation cycle. The incubation cycle may be repeated between about 2 times and about 1000 times, between about 5 times and about 500 times, between about 50 times and about 500 times, between about 150 times and about 250 times, and the like. For the final round of the incubation cycle, it may be preferable to skip the de-aggregation step before analyzing the incubation mixture.

The incubation cycle may be carried out for a time between about 1 minute and about 5 hours, between about 10 minutes and about 2 hours, between about 15 minutes and about 1 hour, between about 25 minutes and about 45 minutes, and the like. In some aspects, incubating the incubation mixture and de-aggregating at least a portion of the misfolded α-syn aggregate comprise an incubation cycle lasting from 0.3 to 1 hours. Each incubation cycle may include independently incubating and de-aggregating the incubation mixture for one or more of: incubating between about 1 minute and about 5 hours and de-aggregating between about 5 seconds and about 10 minutes; incubating between about 10 minutes and about 2 hours and de-aggregating between about 30 sec and about 1 minute; incubating between about 15 minutes and about 1 hour and de-aggregating between about 45 seconds and about 1 minute; incubating between about 25 minutes and about 45 minutes and de-aggregating between about 45 seconds and about 1 minute; and incubating about 1 minute and physically disrupting about 1 minute.

Biological Samples

Aspects of the methods described herein may include the step of obtaining a biological sample from the subject. A "biological sample," as used herein, is meant to include any biological sample from a subject that is suitable for analysis for detection of misfolded α-syn protein. Suitable biological samples include but are not limited to bodily fluids such as blood-related samples (e.g., whole blood, serum, plasma, and other blood-derived samples), urine, sputum, saliva, urine, CSF, and the like. Another example of a biological sample is a tissue sample. The α-syn protein can be assessed either quantitatively or qualitatively, and detection can be determined either in vitro or ex vivo.

The methods involve providing or obtaining a biological sample from the subject. In some aspects, the method includes the step of obtaining a biological sample from the subject. A biological sample can be obtained by any known means including needle stick, needle biopsy, swab, and the like. In an example method, the biological sample is a CSF sample, which may be obtained for example by lumbar puncture, in which a needle is inserted into the subarachnoid space and CSF is then extracted.

In some aspects, the methods of the invention are carried out on a biological sample that is provided. A biological sample may be fresh or stored. Biological samples may be or have been stored or banked under suitable tissue storage conditions. The biological sample may be a biological sample expressly obtained for the assays as described herein or a sample obtained for another purpose that can be subsampled for the assays as described herein. Preferably, biological samples are either chilled or frozen shortly after collection if they are being stored to prevent deterioration of the sample. For example, CSF samples can be stored in polypropylene tubes at −80° C. CSF samples may be frozen in liquid nitrogen ("snap-freeze") or by placing the samples in an environment kept at −80° C., such as a coldroom or freezer.

The biological sample may be pretreated as necessary by dilution in an appropriate buffer solution, concentrated if desired, or fractionated by any number of methods including but not limited to ultracentrifugation, fractionation by fast performance liquid chromatography (FPLC) or HPLC, or precipitation of proteins with dextran sulfate or other methods. Any of a number of standard aqueous buffer solutions at physiological pH, such as phosphate, Tris, or the like, can be used.

Subjects

The terms "individual," "subject," and "patient" are used interchangeably herein irrespective of whether the subject has or is currently undergoing any form of treatment. As used herein, the term "subject" generally refers to any vertebrate, including, but not limited to a mammal. Examples of mammals include primates, including simians and humans, equines (e.g., horses), canines (e.g., dogs), felines, various domesticated livestock (e.g., ungulates, such as swine, pigs, goats, sheep, and the like), as well as domesticated pets (e.g., cats, hamsters, mice, and guinea pigs). Analysis of biological samples from human subjects is of particular interest.

In some aspects, the subject may be at risk of developing PD, of having PD, or being under treatment for PD; at risk of having a disease associated with dysregulation, misfolding, aggregation, or disposition of α-syn, such as MSA, LBD, or PAF; having a disease associated with dysregulation, misfolding, aggregation, or disposition of α-syn; under treatment for a disease associated with dysregulation, misfolding, aggregation, or disposition of α-syn; and the like. In another embodiment, the subject may be at risk of developing Alzheimer's Disease, or may be at risk of developing a neurodegenerative disease associated with dysregulation, misfolding, aggregation, or disposition of α-syn as well as aggregates of other misfolded protein species, such as Abeta and tau.

Determining the Presence of Soluble, Misfolded α-Syn Protein

The method may include determining if a detectable amount of misfolded α-syn aggregate is present in the biological sample. Detection of misfolded α-syn aggregate indicates the presence of soluble, misfolded α-syn in the biological sample. The process of detecting the misfolded α-syn aggregate can be conducted during or after each one of the incubation cycles, or it can be carried out upon completion of a predetermined number of incubation cycles.

In some aspects, the method includes the step of contacting the incubation mixture with a protein aggregation indicator to determine if a detectable amount of misfolded α-syn aggregate is present in the incubation mixture. The protein aggregation indicator can be characterized by exhibiting an indicating state in the presence of misfolded α-syn protein aggregate and a non-indicating state in the absence of misfolded α-syn protein aggregate. Determining the presence of the soluble, misfolded α-syn protein in a biological sample may include detecting the indicating state of the indicator of misfolded α-syn protein aggregate. The indicating state of the indicator and the non-indicating state of the indicator may be characterized by a difference in fluorescence, light absorption, or radioactivity depending on the specific indicator. The step of determining the presence of the soluble, misfolded α-syn protein in a biological sample may include detecting the difference in fluorescence, light absorption, or radioactivity depending on the specific indicator being used.

In several aspects, the method may include contacting a molar excess of the protein aggregation indicator to one or both of the incubation mixture or the detection mixture. The molar excess may be greater than a total molar amount of α-syn protein monomer and the soluble, misfolded α-syn protein in the incubation mixture.

In some aspects, the protein aggregation indicator may include one or more of: ThT, Congo Red, m-I-Stilbene, Chrysamine G, PIB, BF-227, X-34, TZDM, FDDNP, MeO—X-04, IMPY, NIAD-4, luminescent conjugated polythiophenes, a fusion with a fluorescent protein such as green fluorescent protein and yellow fluorescent protein, derivatives thereof, and the like. A suitable protein aggregation indicator is ThT.

A variety of different methods can be used to detect the soluble, misfolded α-syn protein. These include the use of a Western Blot assay, an ELISA, a ThT binding assay, a Congo Red binding assay, a sedimentation assay, electron microscopy, atomic force microscopy, surface plasmon resonance, spectroscopy, and the like. The ELISA may include a two-sided sandwich ELISA. The spectroscopy may include one or more of: quasi-light scattering spectroscopy, multi spectral ultraviolet spectroscopy, confocal dual-color fluorescence correlation spectroscopy, Fourier-transform infrared spectroscopy, capillary electrophoresis with spectroscopic detection, electron spin resonance spectroscopy, nuclear magnetic resonance spectroscopy, Fluorescence Resonance Energy Transfer (FRET) spectroscopy, and the like.

In some aspects, detecting the soluble, misfolded α-syn protein includes contacting the detection mixture with a protease, such as, for example, protease K or thermolysin. The soluble, misfolded α-syn protein may be detected using sequence-based or anti-misfolded protein antibodies using either a Western Blot assay or an ELISA.

In some aspects, determining the presence of the soluble, misfolded α-syn protein in the biological sample includes determining the amount of the soluble, misfolded α-syn protein in the biological sample. The amount of the soluble, misfolded α-syn protein in the sample may be determined compared to a control sample. The amount of the soluble, misfolded α-syn protein in the biological sample may be detected with a sensitivity and specificity of at least about one or more of: 80%, 81%, 82%, 83%, 84%, 85%, 86%, 87%, 88%, 89%, 90%, 91%, 92%, 93%, 94%, 95%, 96%, 97%, 98%, 99%, and 100%. The amount of the soluble, misfolded α-syn protein in the sample detected may be less than about one or more of: 100 nmol, 10 nmol, 1 nmol, 100 pmol, 10 pmol, 1 pmol, 100 fmol, 10 fmol, 3 fmol, 1 fmol, 100 attomol, 10 attomol, and 1 attomol. The amount of the soluble, misfolded α-syn protein in the sample may be detected in a molar ratio to monomeric α-syn protein.

The soluble, misfolded α-syn can be detected or measured by an analytic device such as a kit or a conventional laboratory apparatus, which can be either portable or stationary. In some aspects, the levels of soluble, misfolded α-syn may be compared to the level of corresponding internal standards in the sample or samples when carrying out the analysis to quantify the amount of soluble, misfolded α-syn being detected.

Once the presence and/or level of the soluble, misfolded α-syn has been determined, it can be displayed in a variety of ways. For example, the levels can be displayed graphically on a display as numeric values or proportional bars (i.e., a bar graph) or any other display method known to those skilled in the art. The graphic display can provide a visual representation of the amount of the variance in the biological sample being evaluated.

Concentrating the Soluble, Misfolded α-Syn

In several aspects, the method may include selectively concentrating the soluble, misfolded α-syn protein in one or more of the samples, the incubation mixture, and the detection mixture. In some aspects, the method further comprises the step of concentrating the soluble, misfolded α-syn in the sample before incubating the biological sample using antibodies that specifically bind to soluble, misfolded α-syn. Selectively concentrating the soluble, misfolded α-syn protein may include pre-treating the biological sample prior to forming the incubation mixture. The step of selectively concentrating the soluble, misfolded α-syn protein may include pre-treating the incubation mixture prior to incubating the incubation mixture. The step of selectively concentrating the soluble, misfolded α-syn protein may include contacting the incubation mixture with antibodies that specifically bind to soluble, misfolded α-syn to form a captured soluble, misfolded α-syn protein.

Antibodies are designed for specific binding, as a result of the affinity of complementary determining region of the antibody for the epitope of the biological analyte. An antibody "specifically binds" when the antibody preferentially binds a target structure, or subunit thereof, but binds to a substantially lesser degree or does not bind to a biological molecule that is not a target structure. In some aspects, the antibody specifically binds to soluble, misfolded α-syn with a specific affinity of between $10^{-8}$ M and $10^{-11}$ M. In some aspects, an antibody or antibody fragment binds to the soluble, misfolded α-syn with a specific affinity of greater than $10^{-7}$ M, $10^{-8}$ M, $10^{-9}$ M, $10^{-10}$ or $10^{-11}$ M, between $10^{-8}$ M-$10^{-11}$ M, $10^{-9}$-$10^{-10}$ M, and $10^{-19}$ M-$10^{-11}$ M. In one aspect, specific activity is measured using a competitive binding assay as set forth in Ausubel FM, (1994). Current Protocols in Molecular Biology. Chichester: John Wiley and Sons ("Ausubel"), which is incorporated herein by reference.

Antibodies that specifically bind to soluble, misfolded α-syn may include one or more of: α/β-syn N-19; α-syn C-20-R; α-syn 211; α-syn Syn 204; α-syn 2B2D1; α-syn LB 509; α-syn SPM451; α-syn 3G282; α-syn 3H2897; α/β-syn Syn 202; α/β-syn 3B6; α/β/γ-syn FL-140; and the like. The one or more α-syn-specific antibodies may include one or more of: α/β-syn N-19; α-syn C-20-R; α-syn 211; α-syn Syn 204; and the like. Such antibodies may be obtained as follows: α/β-syn N-19 (cat. No. SC-7012, Santa Cruz Biotech, Dallas, Tex.); α-syn C-20-R (SC-7011-R); α-syn 211 (SC-12767); α-syn Syn 204 (SC-32280); α-syn 2B2D1 (SC-53955); α-syn LB 509 (SC-58480); α-syn SPM451 (SC-52979); α-syn 3G282 (SC-69978); α-syn 3H2897 (SC-69977); α/β-syn Syn 202 (SC-32281); α/β-syn 3B6 (SC-69699); and α/β/γ-syn FL-140 (SC-10717). The one or more α-syn specific antibodies may include one or more of: an antibody specific for an amino acid sequence of α-syn and an antibody specific for a conformation of the soluble, misfolded α-syn protein. The one or more α-syn specific antibodies may be coupled to a solid phase.

The solid phase may include one or more of a paramagnetic particle (e.g., iron oxide) and a multi-well plate. For example, ELISA plates may be coated with the antibodies used to capture α-syn from the biological sample. The antibody-coated ELISA plates may be incubated with a biological sample, unbound materials may be washed off, and the PMCA reaction may be performed on the concentrated sample. Antibodies may also be coupled to particles (e.g., Dynabeads). The particles may be incubated with the patient sample and used to separate α-syn-antibody complexes from the remainder of the biological sample.

In several aspects, the method of concentrating soluble, misfolded α-syn in biological samples may include ultracentrifugation. Soluble, misfolded α-syn can be pelleted from biological samples using high-speed centrifugation. The resulting pellet is then re-suspended in a buffer and analyzes using any of the methods described in this application. The centrifugation step may use detergents, such as, for example, sarkosyl, Tween-20, Triton, and the like.

Methods of Diagnosing Disease Associated with α-Syn Aggregation

Another aspect provides a method for diagnosing a disease associated with α-syn aggregation (i.e., a synucleinopathy) in a subject. The method comprises contacting a biological sample with a monomeric α-syn protein and one or more beads having a mean diameter from about 1 mm to about 5 mm, from greater than 2.3 mm to about 5 mm, from greater than 3 mm to about 5 mm, about 2.38 mm, or about 2.45 mm to form an incubation mixture; incubating the incubation mixture to form a misfolded α-syn aggregate from the monomeric α-syn protein and the soluble, misfolded α-syn of the biological sample; de-aggregating at least a portion of the misfolded α-syn aggregate; repeating the steps of incubating and de-aggregating a number of times sufficient to amplify the soluble, misfolded α-syn of the sample to provide a detectable amount of misfolded α-syn aggregate; determining if a detectable amount of misfolded α-syn aggregate is present in the sample; wherein detection of misfolded α-syn aggregate indicates the subject has a disease associated with α-syn aggregation. The method may include determining or diagnosing the presence of a disease associated with α-syn aggregation in the subject by comparing the amount of the soluble, misfolded α-syn protein in the biological sample to a predetermined threshold amount, wherein a level higher than the threshold amount provides a diagnosis of a disease associated with α-syn aggregation in the subject.

For example, one method for diagnosis of PD comprises obtaining a sample from a subject clinically suspected of having PD and subjecting the sample in triplicate to the PMCA assays described herein, along with healthy controls. A positive sample is considered one where ThT fluorescence at about 490 nm after excitation at about 440 nm is over 5,000 relative fluorescence units (RFUs). If zero or only one of the replicates displays ThT fluorescence over 5,000 RFUs, the subject is considered PD negative. If two of the replicates display ThT fluorescence over 5,000 RFUs, the subject is considered PD inconclusive. In the event of an inconclusive result, the sample may be re-tested in triplicate to attempt to obtain a conclusive result. If all three of the replicates display ThT fluorescence over 5,000 RFUs, the subject is considered PD positive. The methods described herein correlate a PD positive test with a clinically suspected PD sample in over 90% of cases. In another example, one or more algorithms may be used to correlate a PD positive test to a clinically suspected PD sample. The algorithms may be found at U.S. Provisional Patent Application No. 63/073,420 and U.S. Provisional Patent Application No. 63/073,424, each of which is incorporated herein by reference in its entirety.

Protein misfolding disorders (PMDs) include Alzheimer's disease (AD), PD, type 2 diabetes, Huntington's disease, amyotrophic lateral sclerosis, systemic amyloidosis, prion diseases, and the like. PMDs also include disease associated with α-syn aggregation. Misfolded aggregates of different proteins may be formed and accumulate. The misfolded aggregates may induce cellular dysfunction and tissue damage, among other effects. In some aspects, the disease associated with α-syn aggregation is PD, while in further aspects the disease associated with α-syn aggregation is LBD, MSA, or PAF.

The method may include diagnosing PD in the subject based on detecting soluble, misfolded α-syn protein in the biological sample. Alpha-syn misfolding and aggregation has been shown to be associated with PD pathogenesis. Sahay et al., Curr Protein Pept Sci., 18(7):656-676 (2017). A diagnosis of PD may also include comparing the amount of soluble, misfolded α-syn protein in the biological sample to a control sample taken from a control subject to determine the level of soluble, misfolded α-syn protein relative to that present in a healthy subject. The method may include determining or diagnosing the presence of a disease associated with α-syn aggregation in the subject according to the presence of the soluble, misfolded α-syn protein in the biological sample. The method may include determining or diagnosing the presence of PD, MSA, LBD, or PAF, in their own right or in the subject according to the presence of the soluble, misfolded α-syn protein in the biological sample.

In some aspects, the sample may be taken from a subject exhibiting no clinical signs of PD. In other aspects, the biological sample may be taken from a subject exhibiting clinical signs of PD. The most recognizable symptom of PD is motor-related dysfunction. However, additional symptoms include autonomic dysfunction, neuropsychiatric problems (mood, cognition, behavior or thought alterations), sensory dysfunction (especially altered sense of smell), and sleep difficulties.

In some aspects, the method includes treating a subject diagnosed as having a disease associated with α-syn aggregation with α-syn modulating therapy. Several novel therapeutics that are targeting α-syn homeostasis through various mechanisms are currently under development. The α-syn modulating therapy may include inhibiting the production of α-syn inhibiting the aggregation of α-syn, e.g., with a suitable inhibitor, active or passive immunotherapy approaches, and the like. Therapeutic approaches targeting α-syn homeostasis may include active immunization, such as PD01A+ or PD03A+, or passive immunization such as PRX002, BIIB054, ATV:aSyn, ABBV-0805 or MEDI1341.

α-Syn modulating therapy may also include methods to stimulate the immune response of a patient to clear α-syn aggregates. The method described herein for detecting the presence of soluble, misfolded α-syn can be employed to determine which patients may be treated with an α-syn modulating therapy. While there is currently no cure for PD, a variety of drugs are useful for treating the motor symptoms of PD, such as levodopa, dopamine agonists, and monoamine oxidase B inhibitors.

In some aspects, the method is used to monitor treatment of a synucleinopathy in a subject. A biological sample may be taken from the subject under α-syn modulating therapy at different times over a period of time. The method may include determining or diagnosing the subject is one of: responsive to the α-syn modulating therapy according to a change in the soluble, misfolded α-syn protein over the period of time, or non-responsive to the α-syn modulating therapy according to homeostasis of the soluble, misfolded α-syn protein over the period of time. The method may include treating the subject determined to be responsive to the α-syn modulating therapy with the α-syn modulating therapy.

Kits

Another aspect provides a kit for determining the presence of soluble, misfolded α-syn in a biological sample. The kit includes a known amount of a monomeric α-syn protein; a known amount of a protein aggregation indicator; a container for incubating an incubation mixture; a buffer composition; one or more beads having a mean diameter from about 1 mm to about 5 mm, from greater than 2.3 mm to about 5 mm, from greater than 3 mm to about 5 mm, about 2.38 mm, or about 2.45 mm; and instructions directing a user to carry out the method of detecting of soluble, misfolded α-syn described herein. The kit should also include a package for holding the components of the kit.

A kit generally includes a package with one or more containers holding the reagents, as one or more separate compositions or, optionally, as an admixture where the compatibility of the reagents will allow. The kits may further include buffers, labeling agents, controls, and any other materials necessary for carrying out the detection of α-syn. Kits can also include a tool for obtaining a sample from a subject, such as a hypodermic needle for conducting a lumbar puncture.

The kit can also include instructions for using the kit to carry out a method of guiding treatment of a synucleinopathy in a subject. In some aspects, the synucleinopathy is PD. Instructions included in kits can be affixed to packaging material or can be included as a package insert. While the instructions are typically written or printed materials they are not limited to such. Any medium capable of storing such instructions and communicating them to an end user is contemplated by this disclosure. Such media include, but are not limited to, electronic storage media (e.g., magnetic discs, tapes, cartridges, chips), optical media (e.g., CD ROM), and the like. As used herein, the term "instructions" can include the address of an internet site that provides the instructions.

The instructions direct the user to contact the biological sample with a known amount of the monomeric α-syn protein and the one or more beads in the container to form an incubation mixture; incubate the incubation mixture to form a misfolded α-syn aggregate from the monomeric α-syn protein and the soluble, misfolded α-syn of the biological sample; de-aggregate at least a portion of the misfolded α-syn aggregate; repeat the steps of incubating and de-aggregating a number of times sufficient to amplify the soluble, misfolded α-syn of the biological sample to provide a detectable amount of misfolded α-syn aggregate; and contact the incubation mixture with a known amount of a protein aggregation indicator to determine if a detectable amount of misfolded α-syn aggregate is present in the biological sample. Detection of misfolded α-syn aggregate indicates the presence of soluble, misfolded α-syn in the biological sample.

In various aspects, the kit may include the known amount of the monomeric, folded α-syn protein and the known amount of the indicator of misfolded α-syn protein. The kit may include one or more of: a bead distribution apparatus; a multi-well plate including a plurality of wells; a microfluidic plate; a shaking apparatus; an incubating apparatus; and a fluorescence measurement apparatus; included either as one or more of the individual plates or apparatuses, or as a combination device. For example, a shaking microplate reader may be used to perform cycles of incubation and shaking and automatically measure the ThT fluorescence emission during the course of an experiment (e.g., FLUOstar OPTIMA, BMG LABTECH Inc., Cary, N.C.).

An example has been included to more clearly describe a particular embodiment of the invention and its associated advantages. However, there are a wide variety of other aspects within the scope of the present invention, which should not be limited to the particular example provided herein.

EXAMPLES

Example 1: Fast α-Syn PMCA (aS-PMCA) for Detection of α-Syn Seeds in CSF of PD Patients Examples were carried out to demonstrate conditions that facilitate rapid detection of α-syn from a sample obtained from a subject, while avoiding or mitigating self-aggregation of the monomeric protein. The results of these examples are shown in FIGS. 2-9.

Unless otherwise noted, the αS-PMCA reaction conditions used to generate the data shown in FIGS. 2-9 comprised 160 µL of a PMCA mix (100 mM PIPES-NaOH pH 6.5 [Sigma, cat #80635-50G], 500 mM NaCl [Lonza, cat #51202], 10 µM ThT [Sigma, cat #T3516-25G], and 0.3 mg/ml (19.6 µM) of SEQ ID NO. 2 (rec-aS), and 40 µL of CSF. $Si_3N_4$ beads were used in the reaction to accelerate the aggregation. The beads had a diameter of 2.38 mm.

The assay was assembled in 96 well ELISA plates [Corning, cat #3916]. One bead was added to each well and the plate was covered with a pierceable optical film [Excel Scientific, cat #XP-100] to avoid cross-contamination while preparing the assay. After all of the PMCA reactions were pipetted into the plate, the pierceable optical film was removed, and a fluorescent-compatible film was used to cover the plate (Applied Biosystems, cat #4311971).

The plate was transferred to a FLUOstar® Omega Microplate Reader [BMG], an instrument that shakes, incubates, and reads fluorescence automatically. The plate was orbitally shaken at 800 rpm for 1 minute, read (440-10 excitation and 490-10 emission), and incubated at 37° C. The plate was shaken for 1 minute every 29 minutes, which constitutes an αS-PMCA cycle of 30 minutes. 200 cycles were performed for the fast assay containing beads (100 h, ~4 days), compared to 600 cycles of the slow assay that does not contain beads (300 h, ~12 days).

The beads used in the experiments were made from pure $Si_3N_4$ material with extreme high density from uniform compaction (3.25 g/cm$^3$). The beads were high precision "Grade 3," meaning that they are pure $Si_3N_4$ ceramic balls that are 3/1,000,000" from exactly round in sphericity.

Abcam synthetic seeds aggregate very quickly in PMCA, and they were used as an αS-aggregate model to evaluate the acceleration of the seeded aggregation in aCSF. See FIGS. 2A-2E. The seeds were added to 40 µL of aCSF to mimic a CSF sample containing endogenous aS seeds (e.g., from human PD-CSF). Given the fast aggregation of the synthetic seeds, a small acceleration in their aggregation indicates a substantial acceleration for human CSF carrying αS-seeds.

Figure 2A:
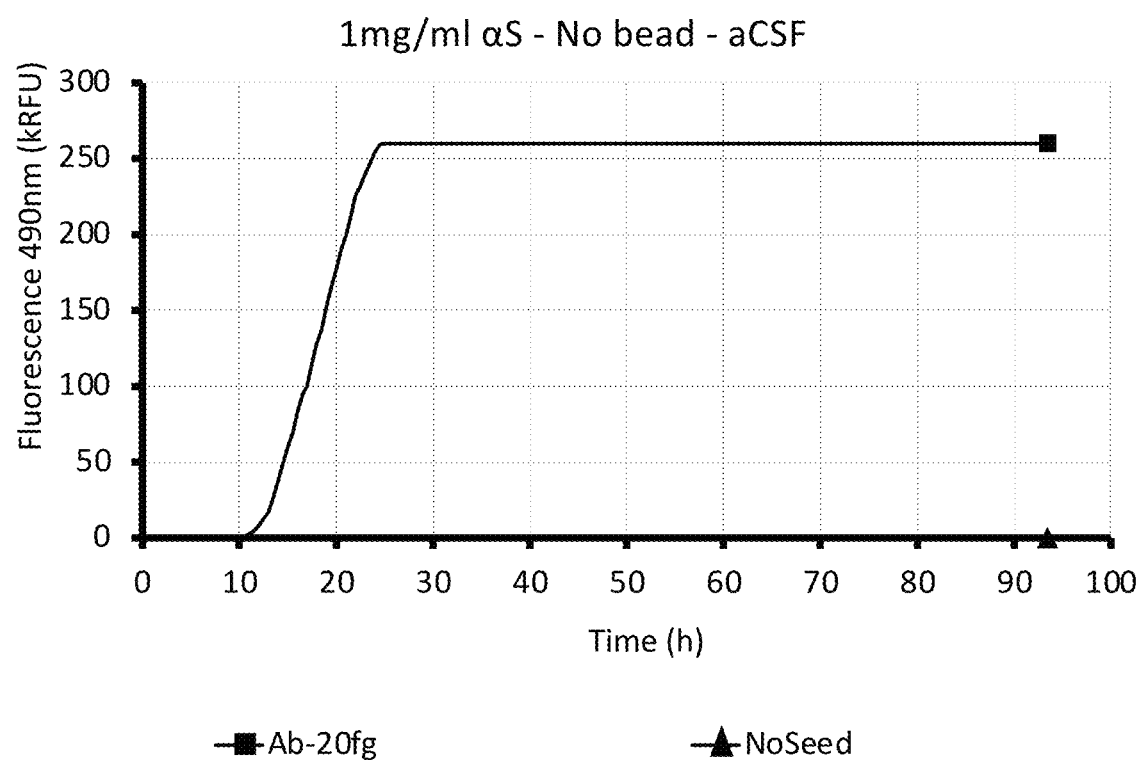
FIGS. 2A-2E demonstrate example effects of various $Si_3N_4$ bead sizes on self-aggregation when carrying out PMCA (37° C., 700 rpm, 1 min on, 29 min off), showing fluorescence when using A) 1 mg/mL α-syn and no bead in artificial CSF (aCSF), B) 1 mg/mL α-S and a 2 mm bead in aCSF, C) 1 mg/mL α-S and a 1.5 mm bead in aCSF, D) 1 mg/mL α-S and a 0.8 mm bead in aCSF, and E) 1 mg/mL α-S and a 0.4 mm bead in aCSF. Recombinant Abcam α-syn seeds were used to mimic α-syn seeds present in PD-CSF to evaluate seed aggregation.
Figure 2B:
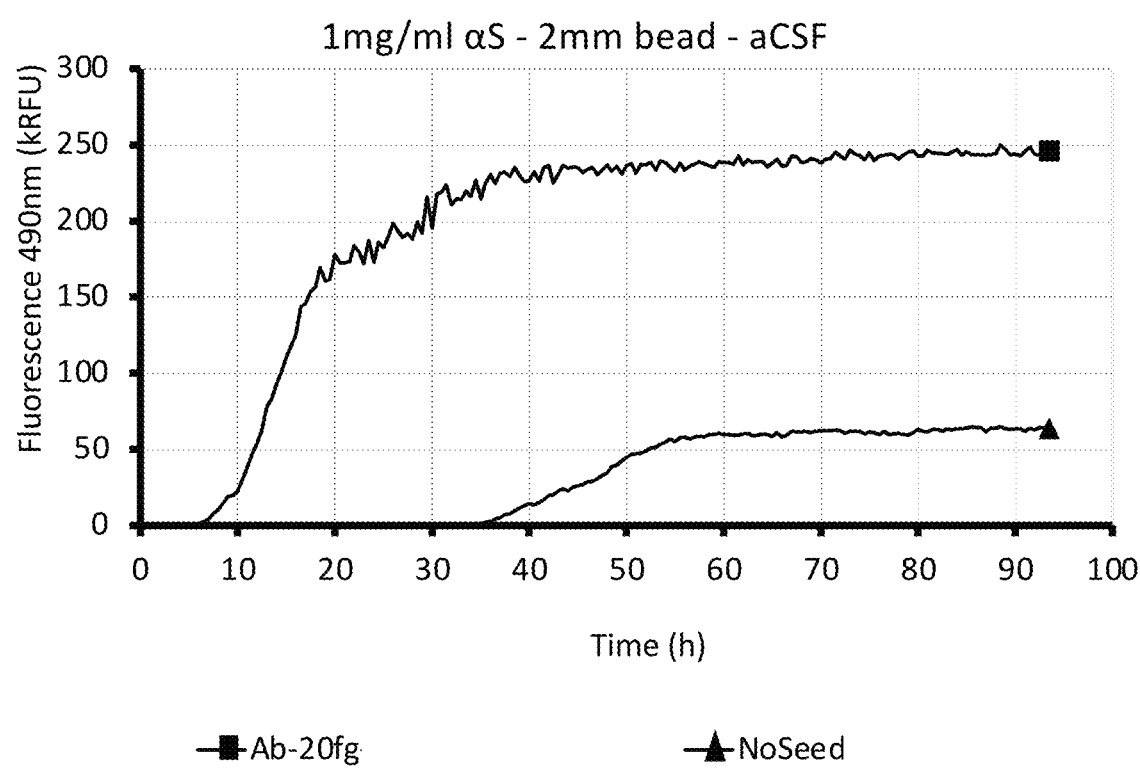
Figure 2C:
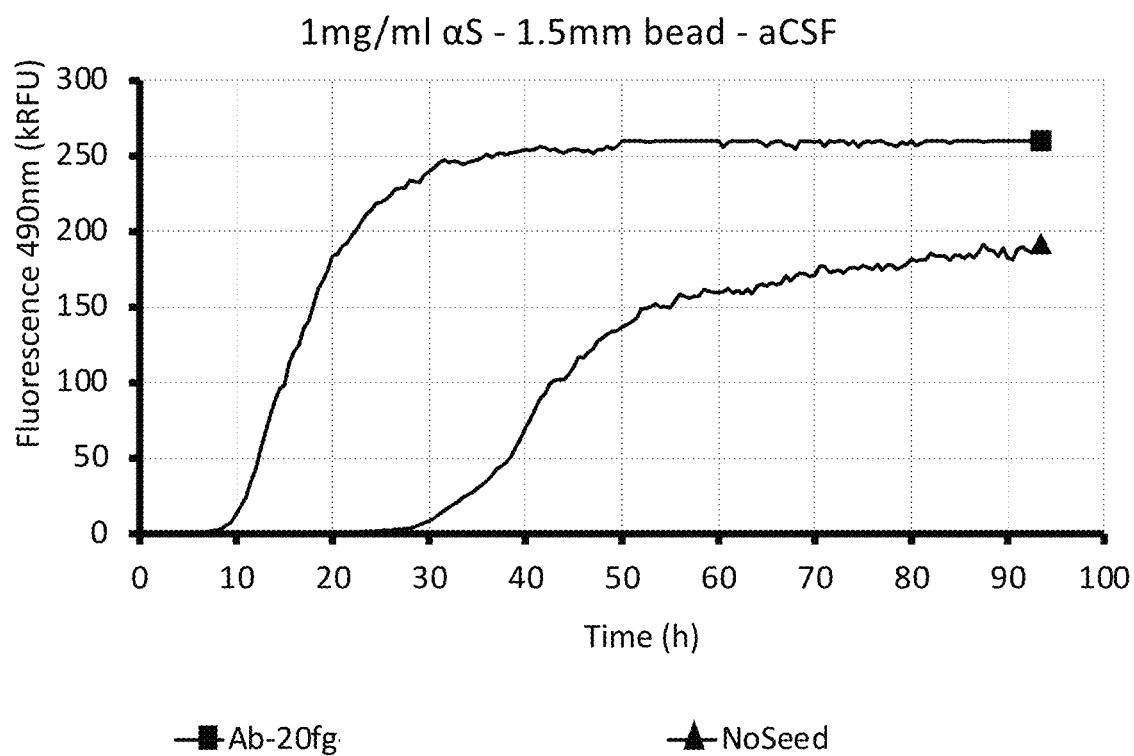
Figure 2D:
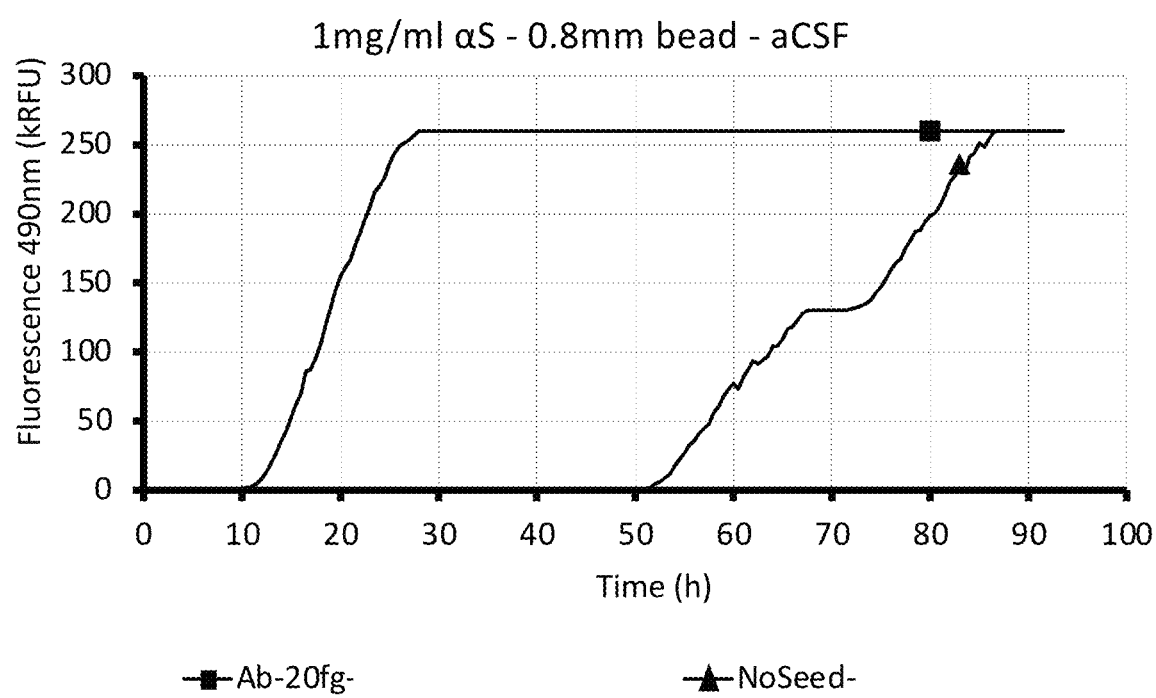
Figure 2E:
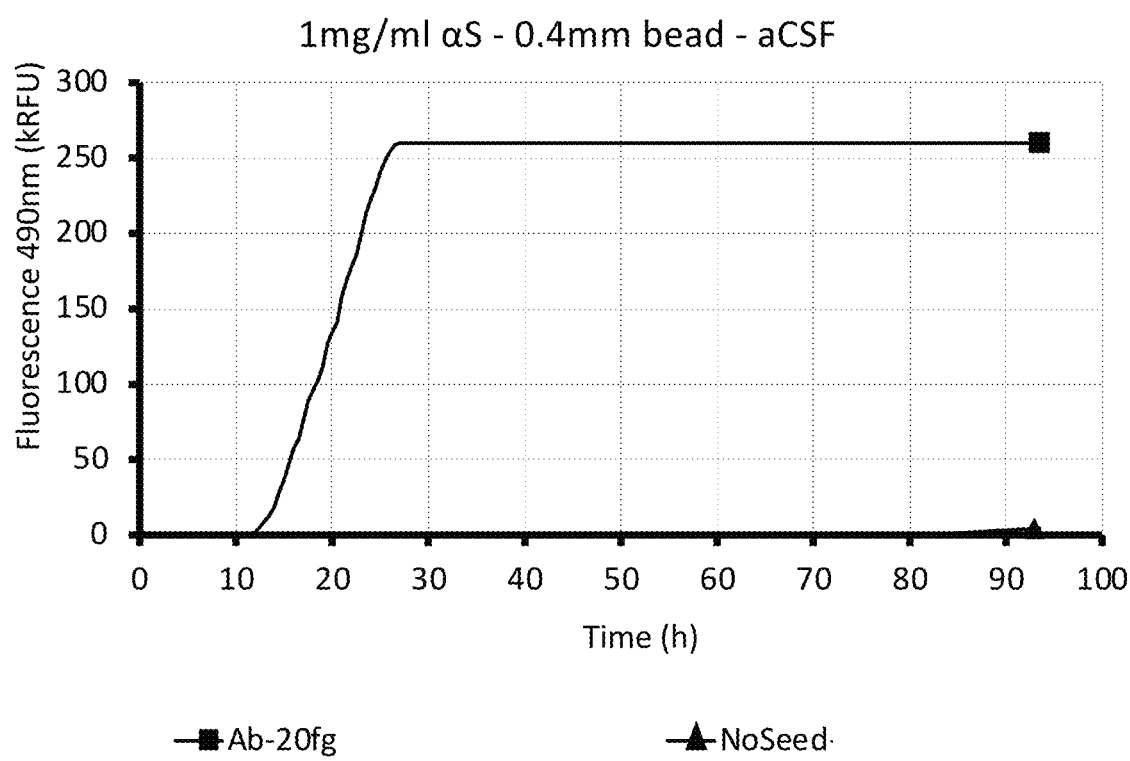

FIG. 2A shows 1 mg/mL of substrate and no beads. The seeded aggregation of 20 fg of Abcam seeds started after 10 h and there was no self-aggregation (the No Seed control displays no aggregation). The inclusion of beads larger than 0.4 mm in the PMCA reaction induced self-aggregation (FIGS. 2B, 2C, and 2D). The bigger the bead, the faster the aggregation of Ab-seeds (20 fg). 0.4 mm beads seemed to have no effect accelerating seeded aggregation (FIG. 2A vs FIG. 2E). The 0.4 mm beads were very difficult to handle and were not further used, but they seemed to have no detrimental effect on the PMCA (i.e., there was no self-aggregation).

Figure 3A:
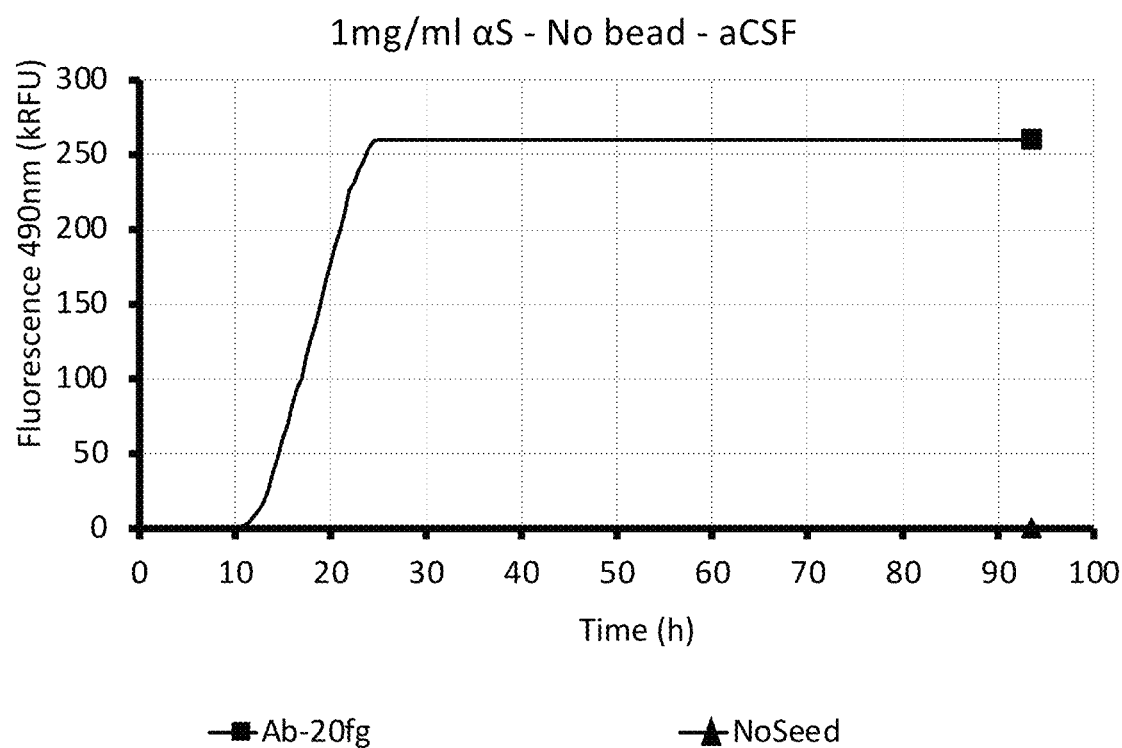
FIGS. 3A-3D demonstrate example effects on self-aggregation by reducing the concentration of substrate when using a 1.5 mm bead in 40 uL of aCSF. PMCA was carried out using $Si_3N_4$ beads, usually with one bead per well, using recombinant Abcam α-syn seeds at 37° C., 700 rpm, for 1 minute on and 29 minutes off, with A) showing the fluorescence when using 1 mg/mL α-S with no bead in 40 uL of aCSF, B) showing the fluorescence when using 1 mg/mL α-S with a 1.5 mm bead in 40 uL of aCSF, C) showing the fluorescence when using 0.5 mg/mL α-S with a 1.5 mm bead in 40 uL of aCSF, and D) showing the fluorescence when using 0.1 mg/mL α-S with a 1.5 mm bead in aCSF.
Figure 3B:
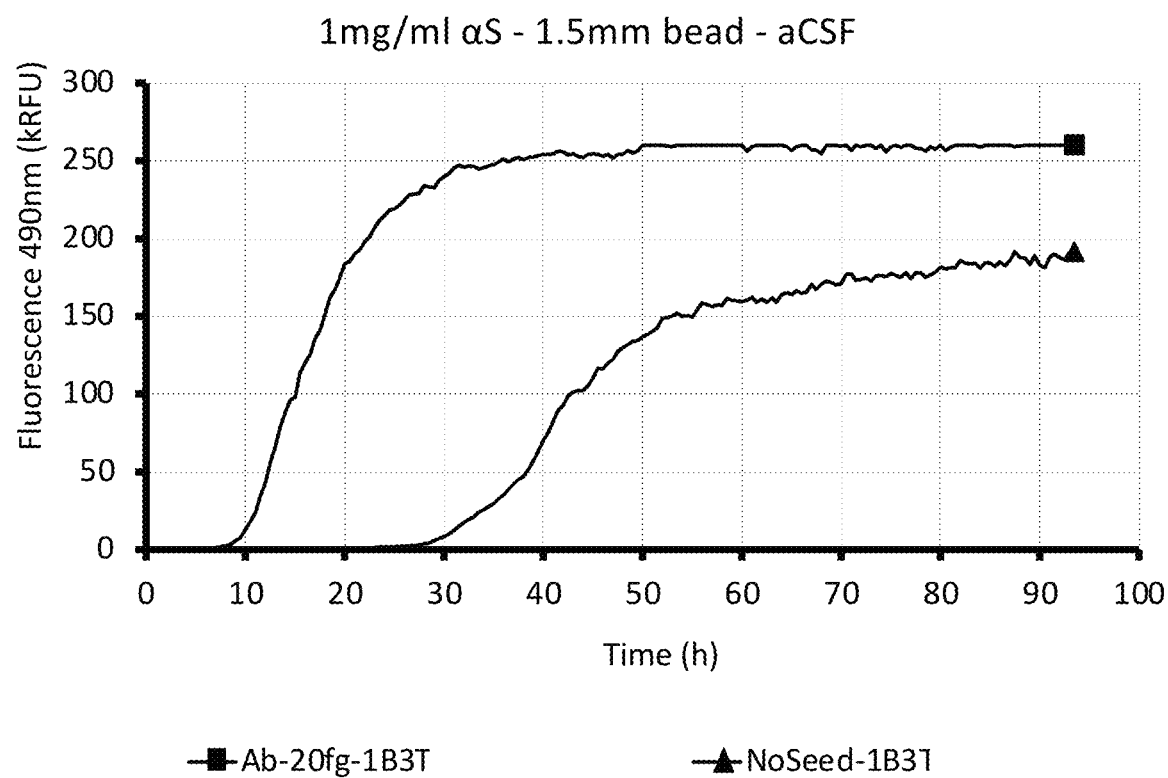
Figure 3C:
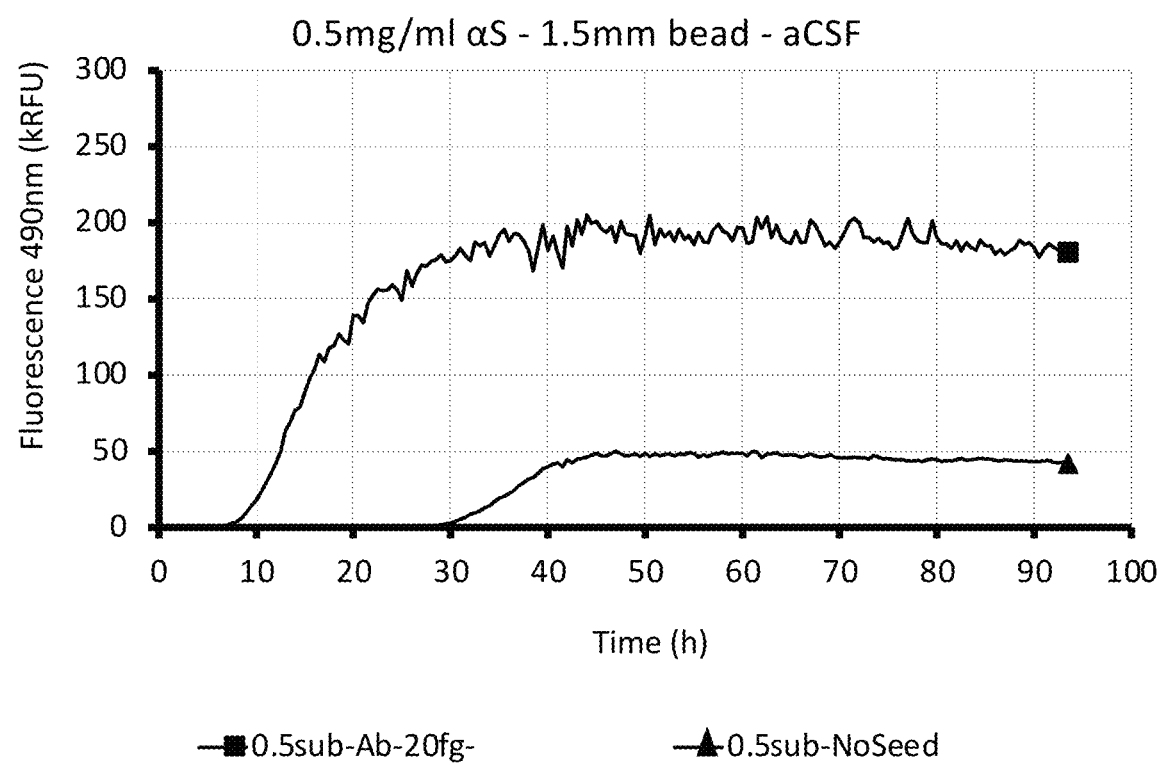
Figure 3D:
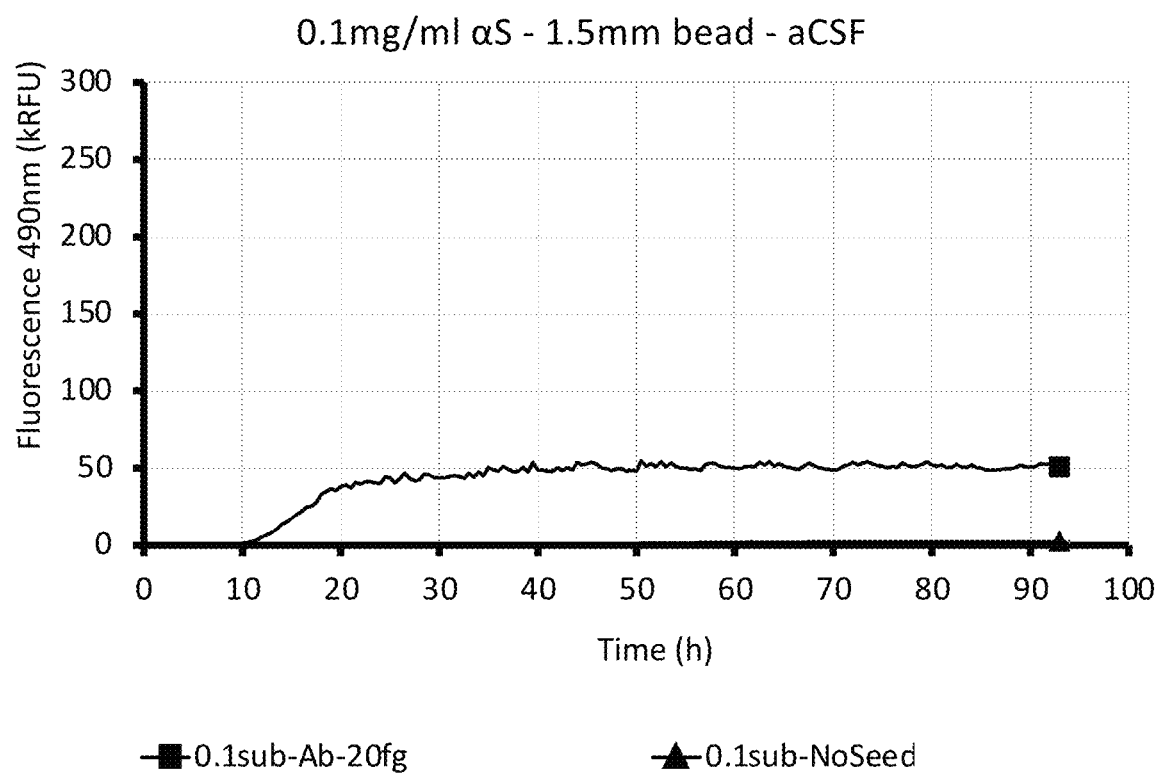

FIG. 3A shows 1 mg/mL of substrate and no beads. The addition of 1.5 mm beads induced self-aggregation of the No Seed control (FIG. 3B). To reduce self-aggregation, the concentration of rec-aS was reduced to 0.5 and 0.1 mg/mL. When using 0.5 mg/ml and 1.5 mm beads (FIG. 3C), there was a reduction in self-aggregation compared to 1 mg/ml, while 20 fg still started aggregating before 10 h. When using 0.1 mg/ml (FIG. 3D), there was no self-aggregation, but there was also no or insufficient acceleration of 20 fg aggregation compared to the no bead circumstance (FIG. 3A). In addition, when using 0.1 mg/ml, the difference in fluorescence between positive and control (50,000 RFU) (FIG. 3D) was smaller than using 0.5 mg/ml (150,000 RFU) (FIG. 3A).

Figure 4A:
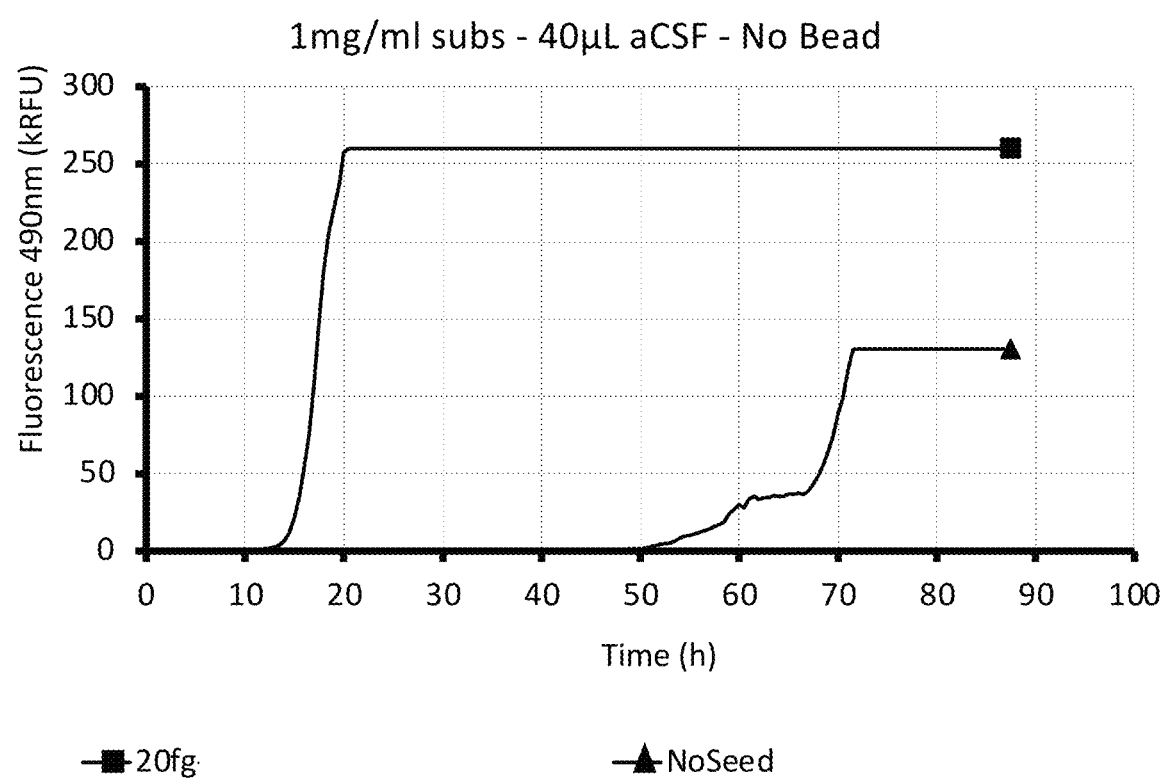
FIGS. 4A-4C demonstrate example effects of increasing the temperature to 42° C. on the PMCA assay. PMCA was carried out using $Si_3N_4$ beads and recombinant Abcam α-syn seeds at 42° C., 700 rpm, for 1 minute on and 29 minutes off, with A) showing the fluorescence when using 1 mg/mL substrate in 40 μL aCSF with no bead, with B) showing the fluorescence when using 1 mg/mL substrate in 40 μL aCSF with a 0.8 mm bead, and C) showing the fluorescence when using using 0.1 mg/mL substrate in 40 μL aCSF with a 1.5 mm bead.
Figure 4B:
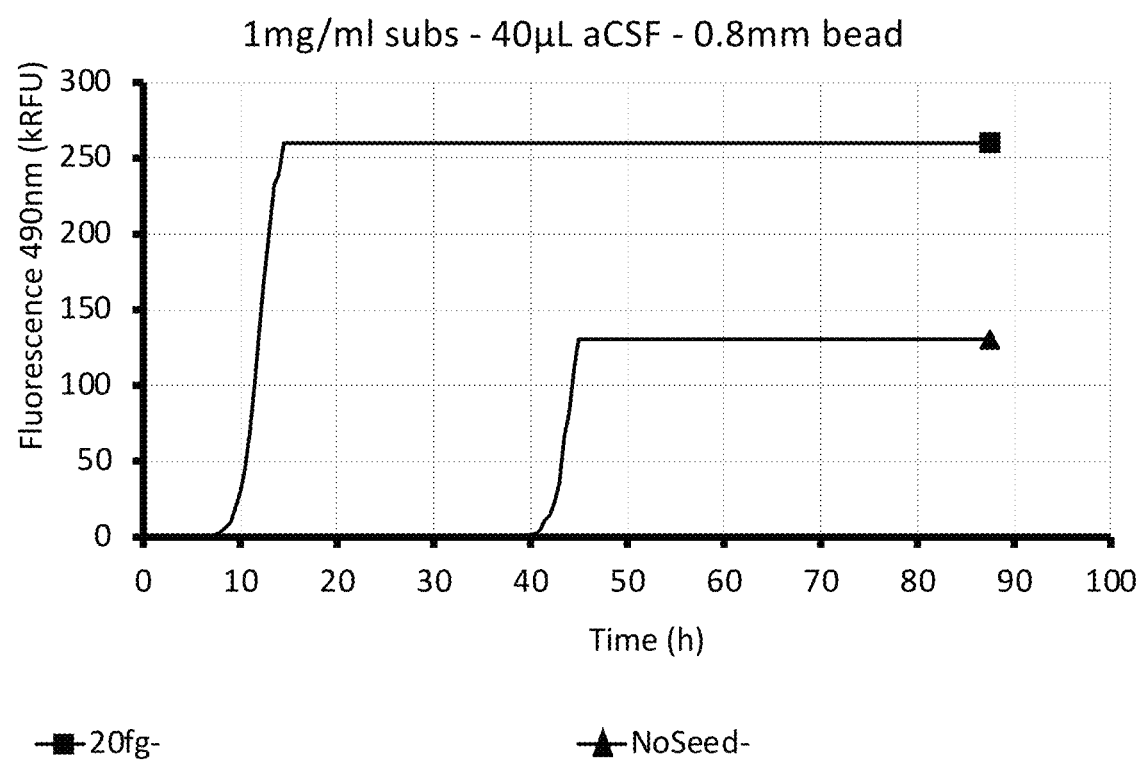
Figure 4C:
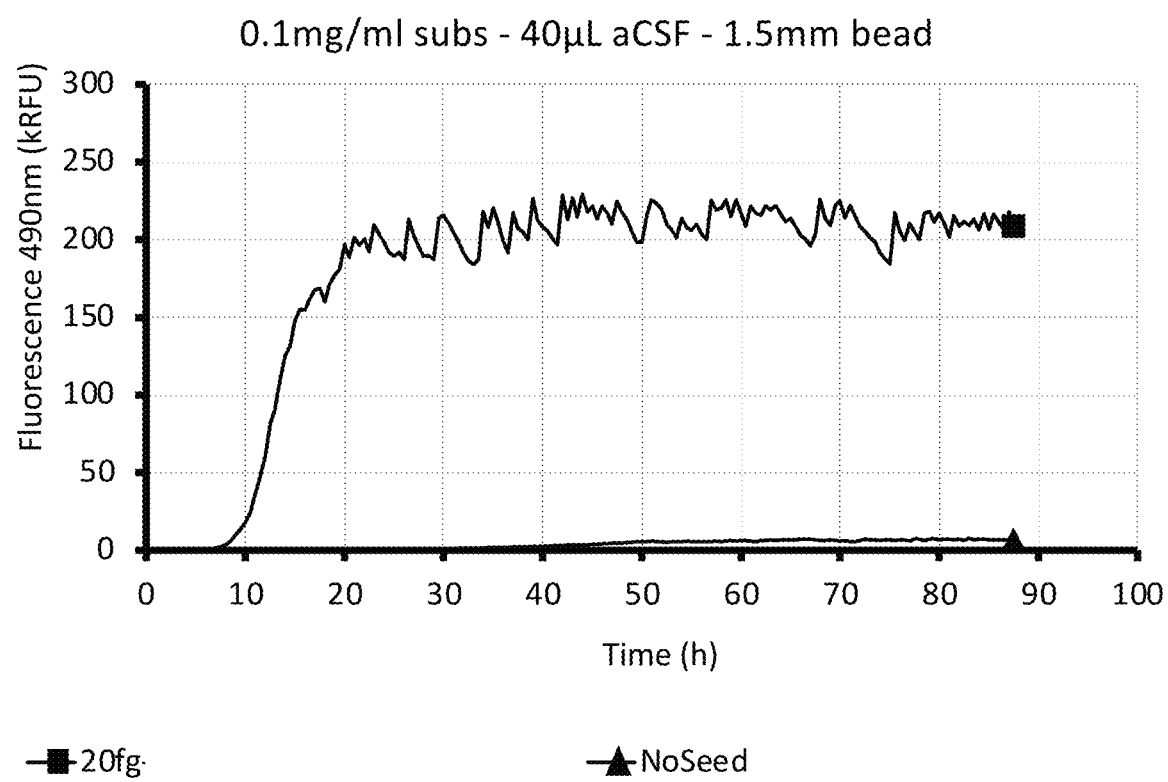

To further accelerate the αS-PMCA assay, the effect of increasing the temperature to 42° C. was evaluated. When omitting beads (FIG. 4A), there was self-aggregation starting at 50 h and seeded aggregation of 20 fg started at ~15 h. After adding one 0.8 mm bead (FIG. 4B), 20 fg aggregated faster, but self-aggregation accelerated to 40 h as well. Self-aggregation was drastically reduced by decreasing the substrate to 0.1 mg/ml and using a larger bead (FIG. 4C).

Figure 5A:
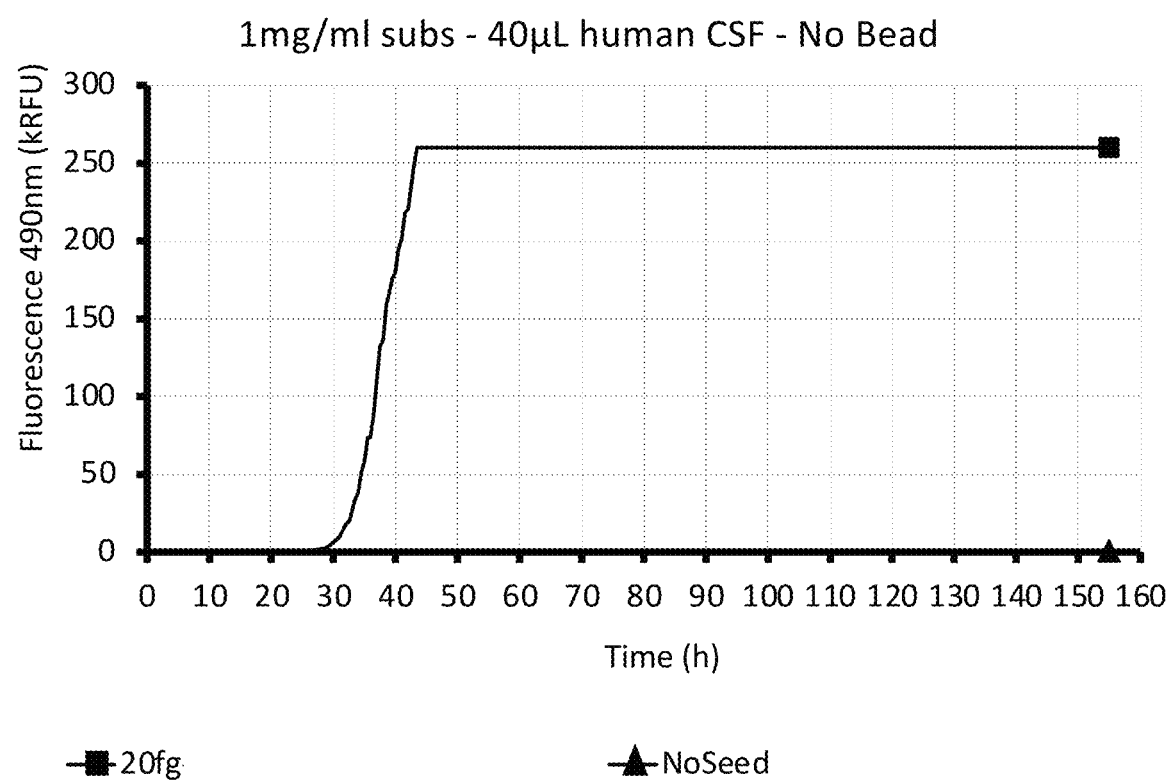
FIGS. 5A-5F demonstrate that beads having a size of 2.38 mm accelerate seeded aggregation and increase the aggregation slope in PMCA. PMCA was carried out using $Si_3N_4$ beads, usually with one bead per well, using recombinant Abcam α-syn seeds at 37° C., 700 rpm, for 1 minute on and 29 minutes off, and using human CSF rather than aCSF, with A) showing the fluorescence when using 1 mg/mL substrate in 40 μL human CSF with no bead, B) showing the fluorescence when using 1 mg/mL substrate in 40 μL human CSF with a 0.8 mm bead, C) showing the fluorescence when using 1 mg/mL substrate in 40 μL human CSF with a 2.38 mm bead, D) showing the fluorescence when using 0.1 mg/mL substrate in 40 μL human CSF with a 0.8 mm bead, E) showing the fluorescence when using 0.1 mg/mL substrate in 40 μL human CSF with a 1.5 mm bead, and F) showing the fluorescence when using 0.1 mg/mL substrate in 40 μL human CSF with a 2.38 mm bead.
Figure 5B:
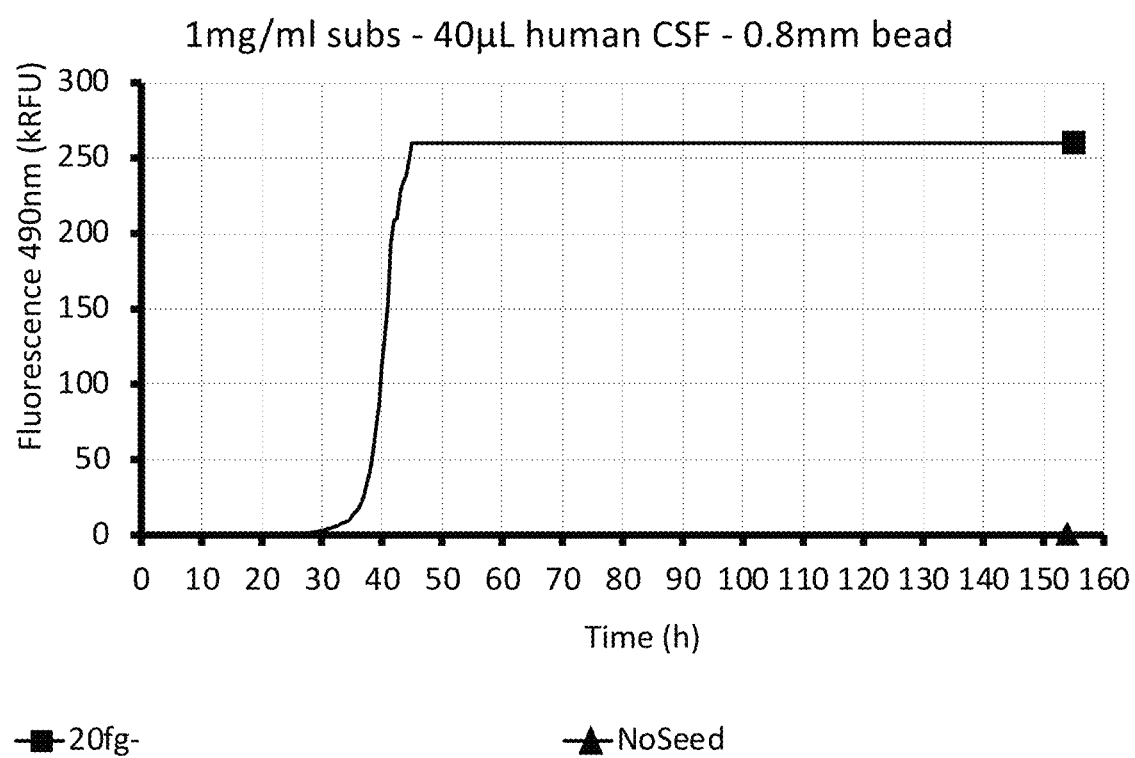
Figure 5C:
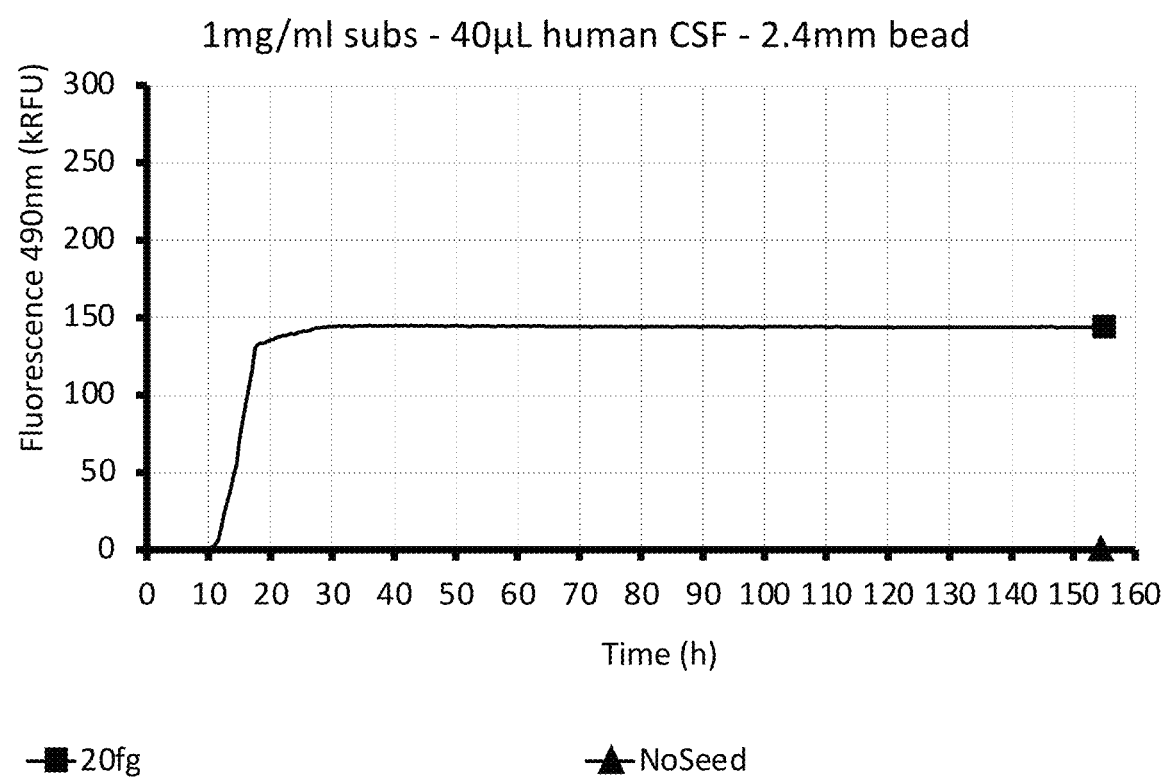
Figure 5D:
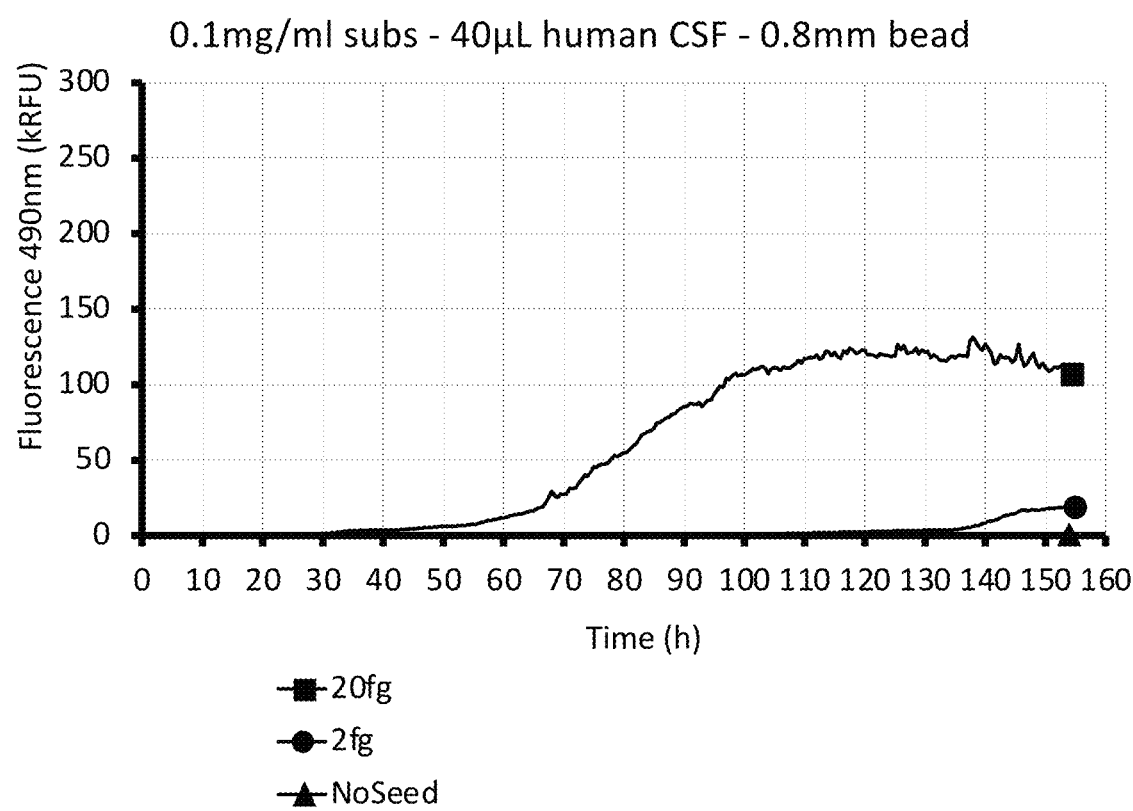
Figure 5E:
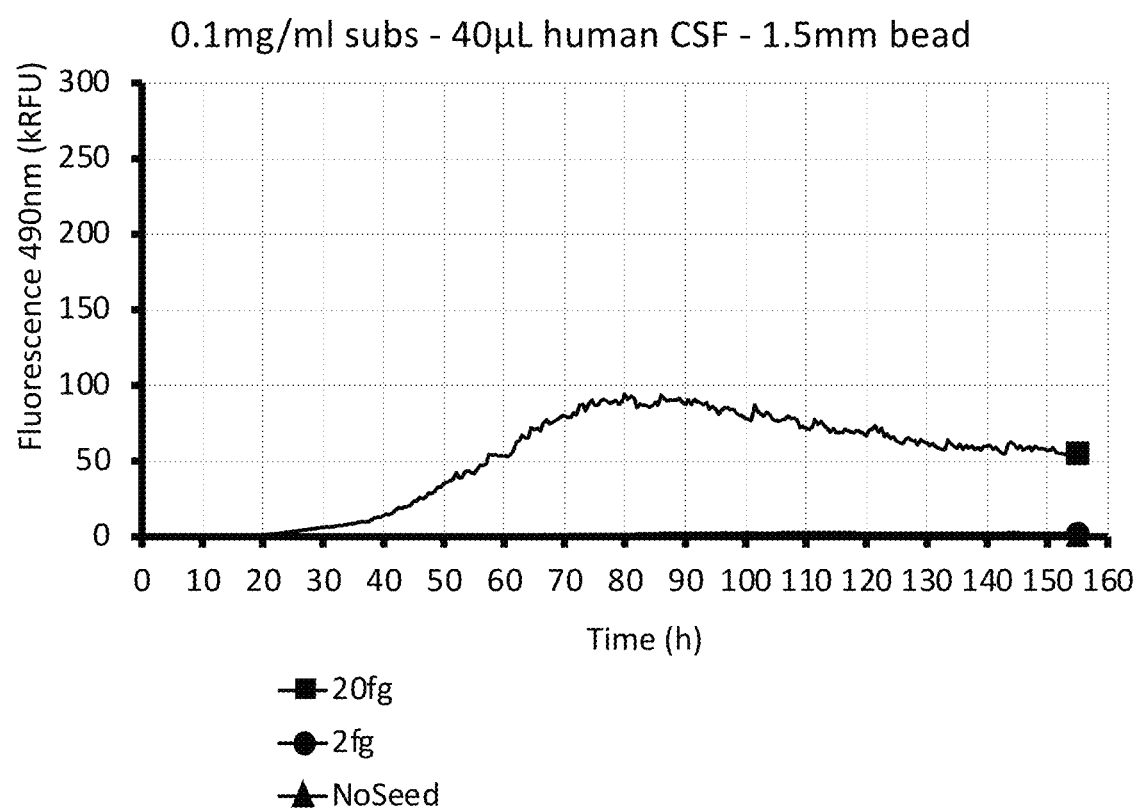
Figure 5F:
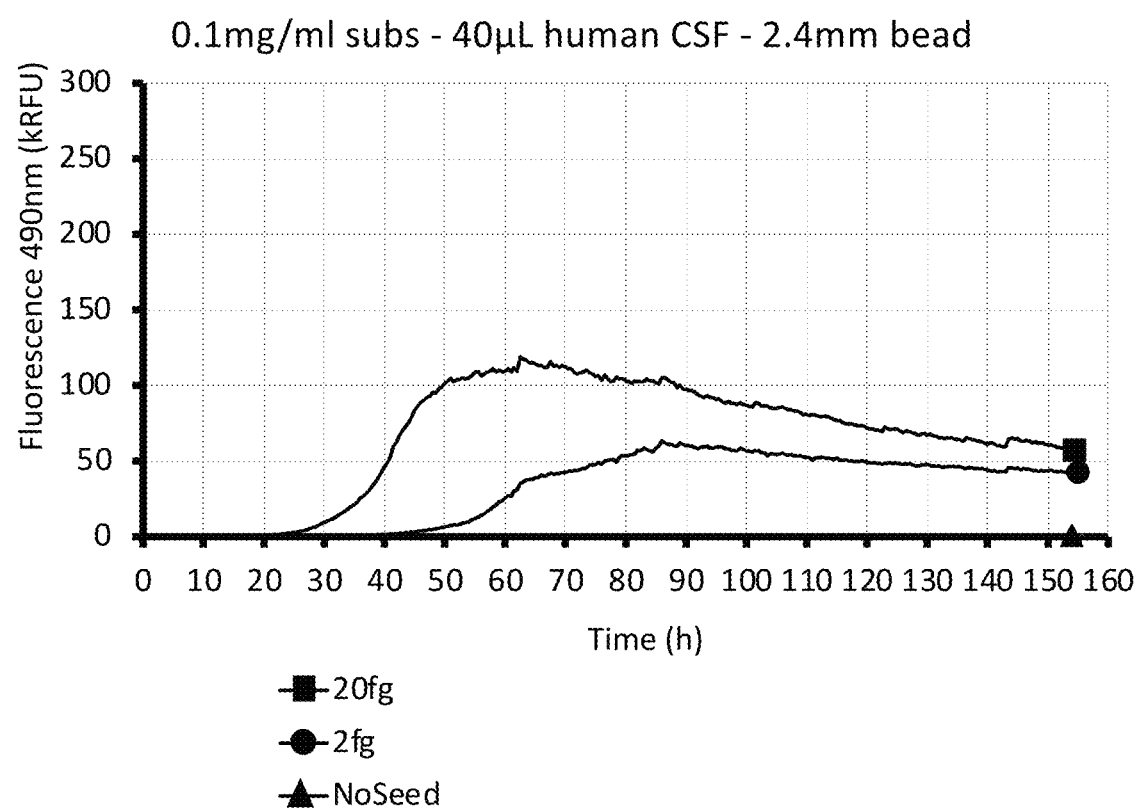

The previous results suggested that bigger beads have a more significant effect on the αS-PMCA. Thus, amplification was evaluated using human control CSF as the matrix. 20 fg of Abcam αS-seeds diluted in water were added to CSF for seeded and No Seed control, respectively (FIG. 5A). In these conditions, beads of different sizes were evaluated at 37° C. With 1 mg/ml of substrate, only 2.38 mm beads (FIG. 5C) showed acceleration of seeded aggregation compared to no bead control (FIG. 5A), while 0.8 mm beads did not show any effect (FIG. 5B). Using human CSF reduced self-aggregation as evidenced by the fact that the No Seed controls were all flat (FIGS. 5A-C). With 0.1 mg/ml, it was confirmed that bigger beads accelerate seeded aggregation and increased the aggregation slope (FIG. 5D-F). However, the signal was low compared to 1 mg/ml.

Figure 6A:
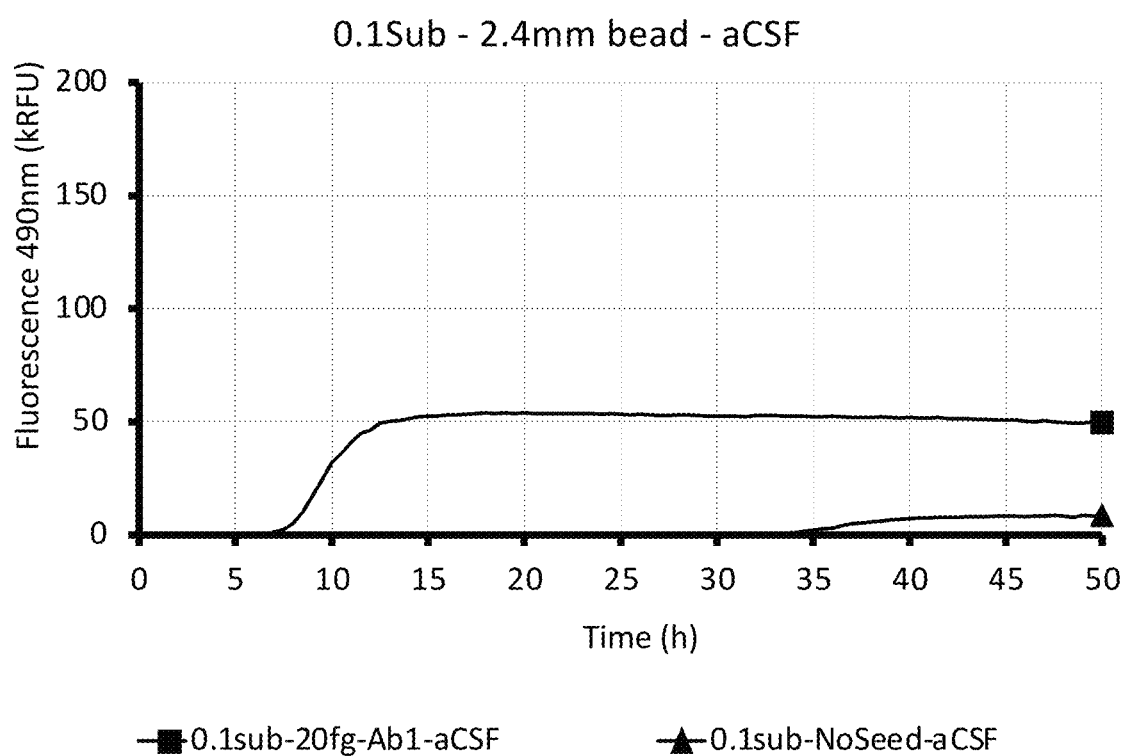
FIGS. 6A-6F demonstrate decreased self-aggregation over time when combining higher temperature, bigger beads, and higher shaking using two different concentrations of substrate (0.1 and 0.3 mg/ml). PMCA was carried out using $Si_3N_4$ beads, with one bead per well, using recombinant Abcam α-syn seeds at 42° C., 800 rpm, for 1 minute on and 29 minutes off, and using aCSF, with A) showing the fluorescence when using 0.1 mg/mL substrate with 2.38 mm beads, B) showing the fluorescence when using 0.1 mg/mL substrate with 2 mm beads, C) showing the fluorescence when using 0.1 mg/mL substrate with 1.5 mm beads, D) showing the fluorescence when using 0.3 mg/mL substrate with 2.38 mm beads, E) showing the fluorescence when using 0.3 mg/mL substrate with 2 mm beads, and F) showing the fluorescence when using 0.3 mg/mL substrate with 1.5 mm beads.
Figure 6B:
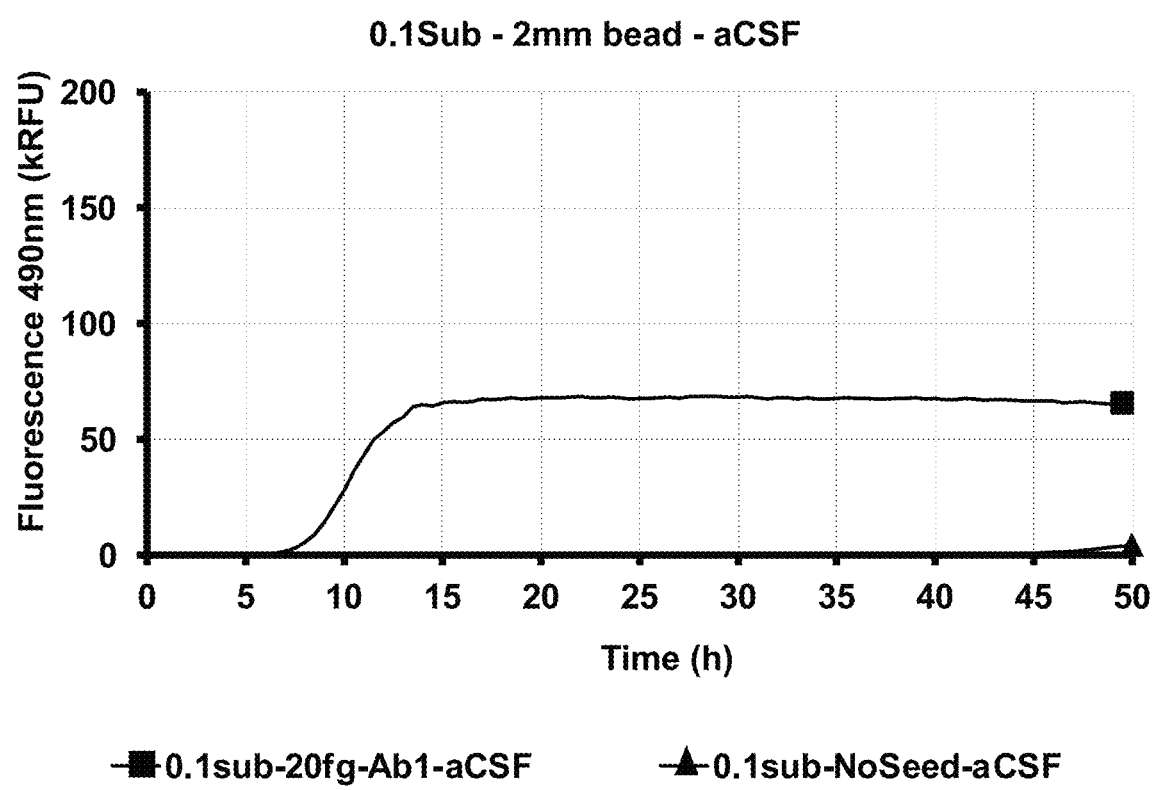
Figure 6C:
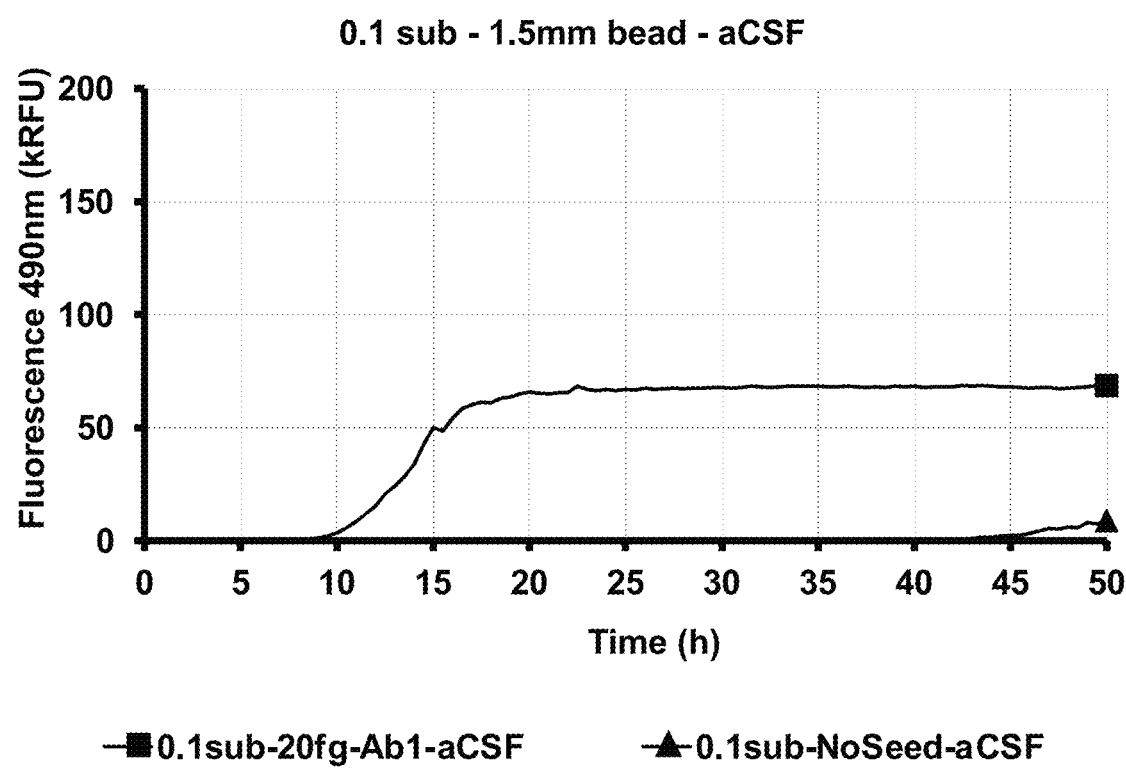
Figure 6D:
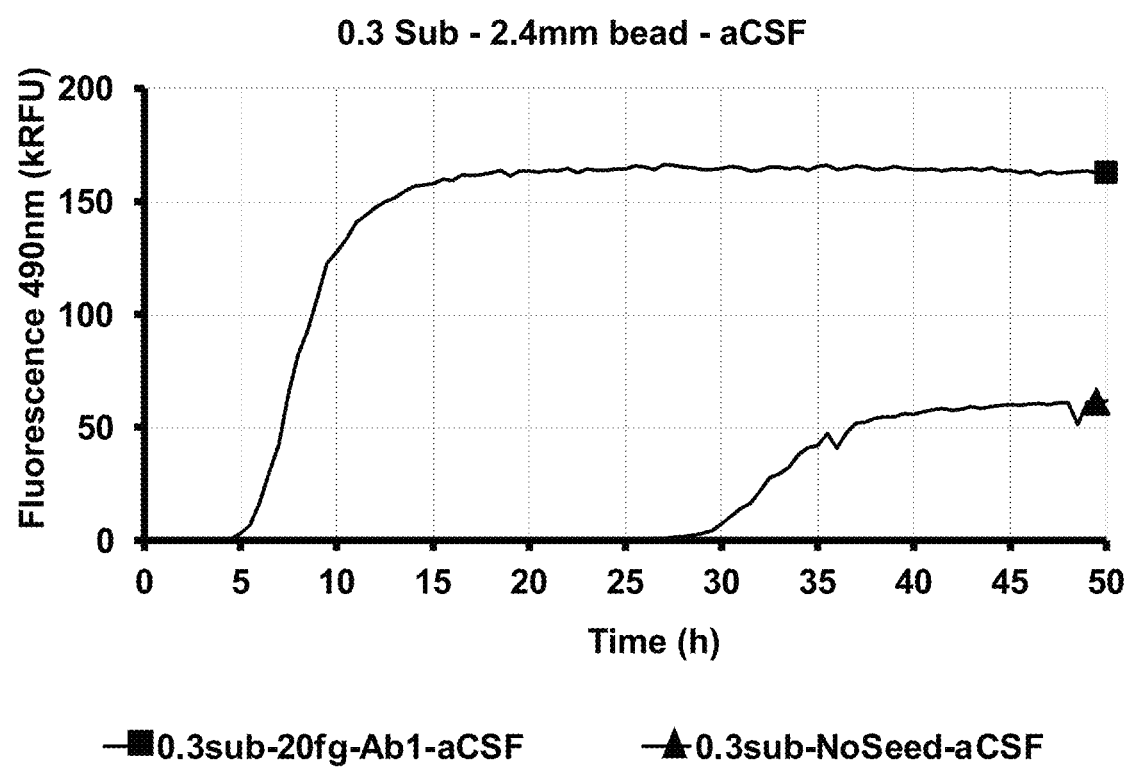
Figure 6E:
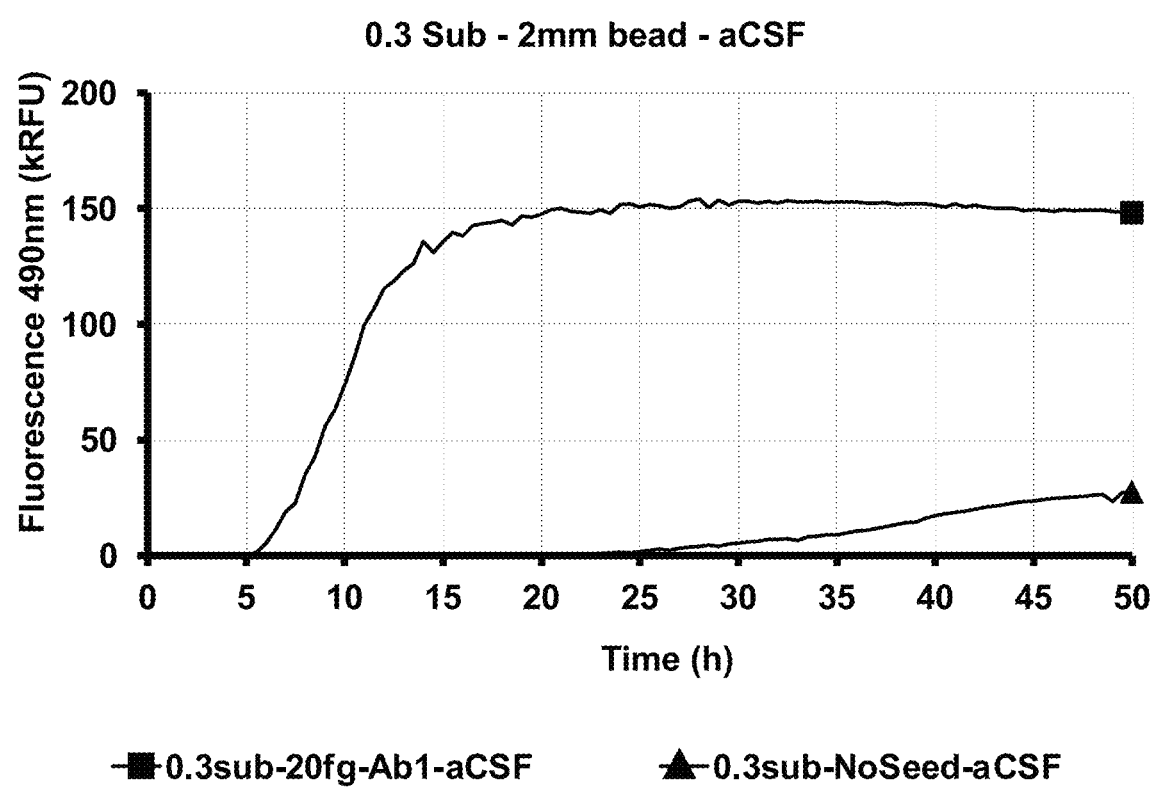
Figure 6F:
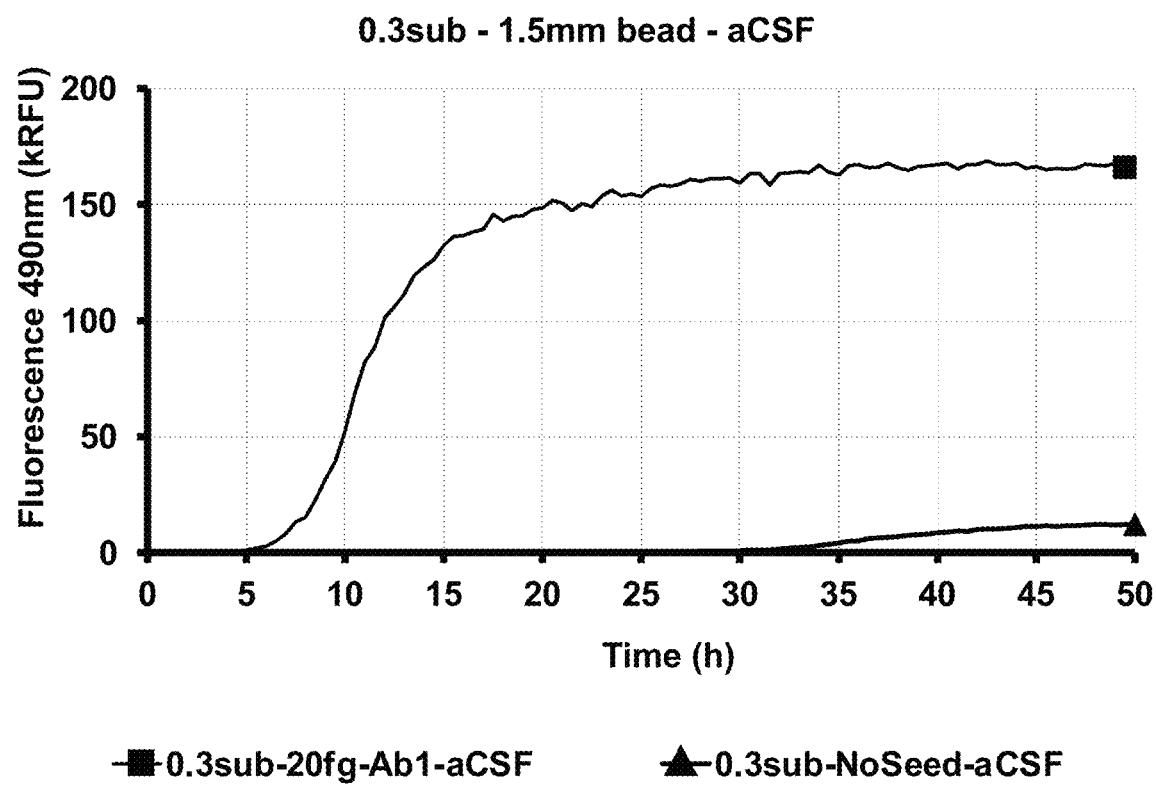

Higher temperature, bigger beads, and higher shaking were combined, using 2 different concentrations of substrate (0.1 and 0.3 mg/ml). PMCA was carried out using $Si_3N_4$ beads, with one bead per well, using recombinant Abcam α-syn seeds at 42° C., 800 rpm, for 1 minute on and 29 minutes off, and using aCSF. Seeded aggregation in aCSF was faster when using 0.3 mg/ml (FIGS. 6D-F) than 0.1 mg/ml (FIGS. 6A-C).

Figure 7A:
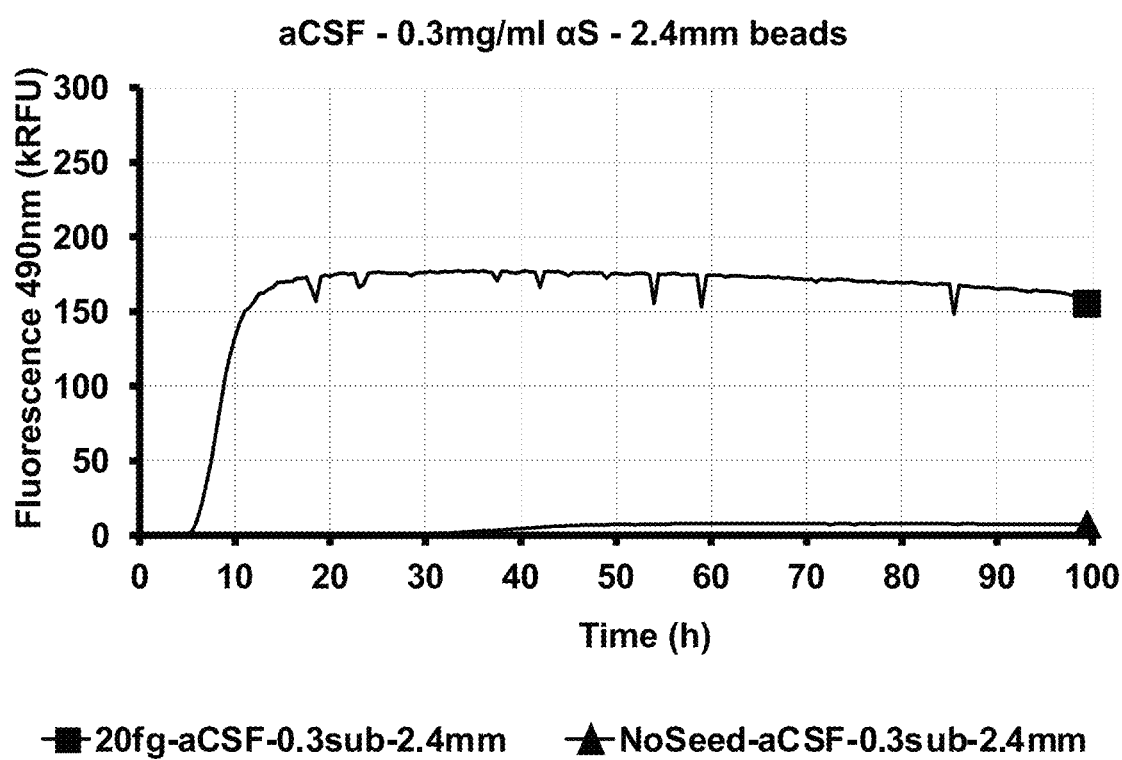
FIGS. 7A-7B demonstrate example comparative results obtained when using aCSF or human CSF. PMCA was carried out using $Si_3N_4$ beads, with one bead per well, using recombinant Abcam α-syn seeds at 42° C., 800 rpm, for 1 minute on and 29 minutes off, with A) showing the fluorescence when using 0.3 mg/mL substrate, 2.38 mm beads, and aCSF, and B) showing the fluorescence when using 0.3 mg/mL substrate, 2.38 mm beads, and human CSF.
Figure 7B:
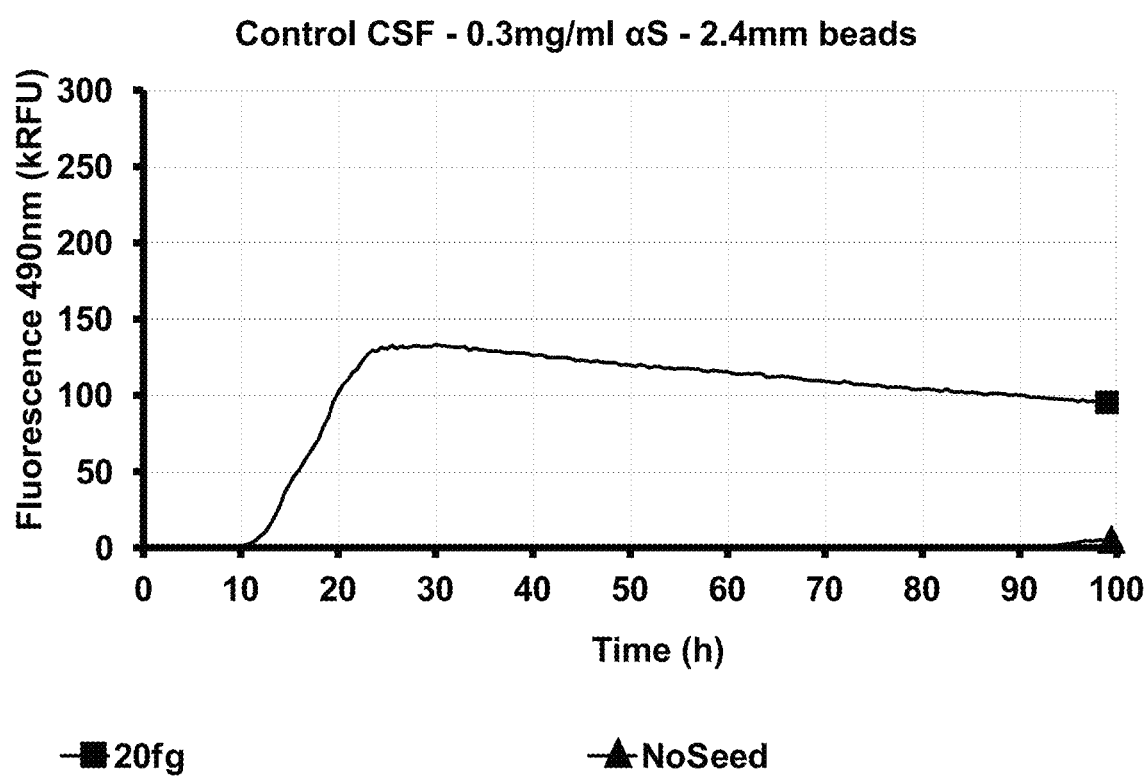

The experiment was repeated using 0.3 mg/ml of substrate, 42° C., 800 rpm, and 2.38 mm beads using aCSF. 20 fg of seeds were positive before 10 h when spiked in aCSF (FIG. 7A), while the No Seed control showed a minor increase in fluorescence after 40 h. Human control CSF was also used to evaluate these αS-PMCA conditions. 20 fg of seeds started aggregating 10$h$, while the control CSF without seeds stayed flat for nearly 100 h (FIG. 7B).

Figure 8A:
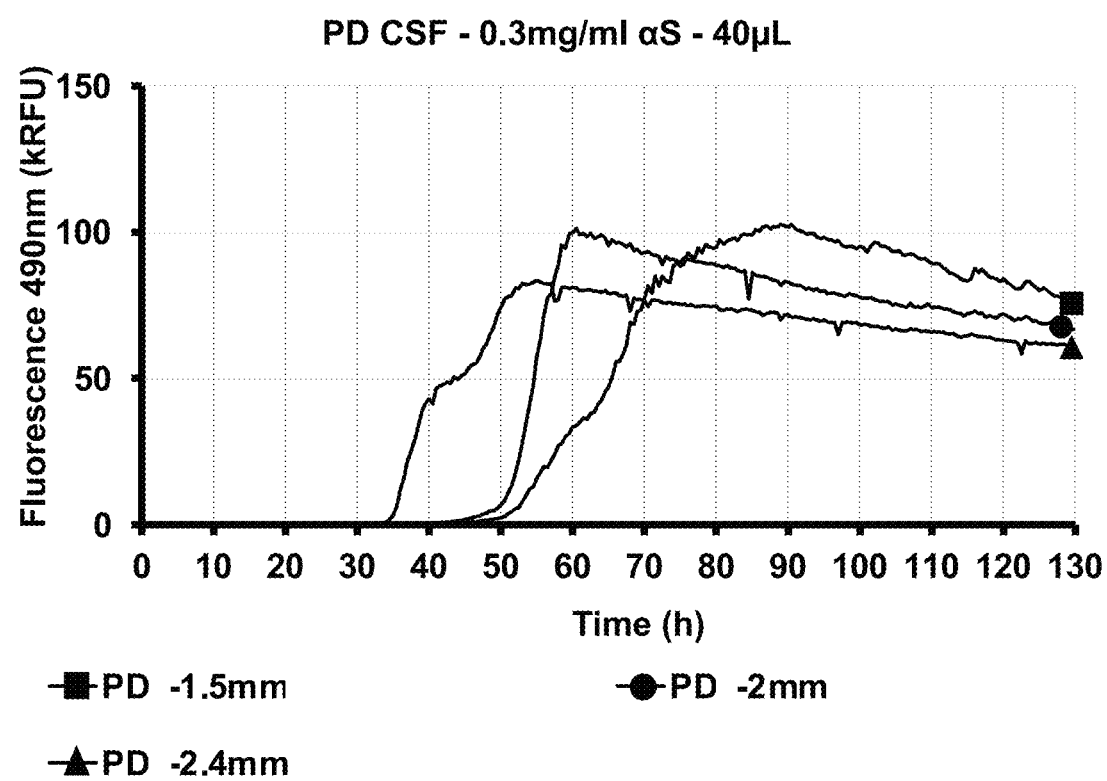
FIGS. 8A-8C demonstrate example effects of using beads to evaluate endogenous α-S seeds in a CSF sample obtained from a subject clinically diagnosed as having PD. For FIGS. 8A-8C, PMCA was carried out using recombinant α-syn seeds at 42° C., 800 rpm, for 1 minute on and 29 minutes off, with A) showing the fluorescence when using $Si_3N_4$ beads, with one bead per well, and using 0.3 mg/mL α-S in a 40 μL CSF sample obtained from a subject having PD, while B) shows the fluorescence when using $Si_3N_4$ beads, with one bead per well, and using 0.3 mg α-S in a 40 μL sample of control CSF. For FIG. 8C, PMCA was carried out without beads, and using 0.3 mg/mL α-S in a 40 μL CSF sample obtained from the subject having PD.

The next step was to evaluate human endogenous αS-seeds in a PD CSF sample, using 1.5, 2, and 2.38 mm $Si_3N_4$ beads (FIG. 8A). The PD sample aggregated before 60 h with all three beads. As a comparison, the PD samples that aggregate faster in the slow assay conditions (as defined below) take 100-150 h, with the average of the PD samples aggregating between 150-250 h (FIG. 8C).

Figure 8B:
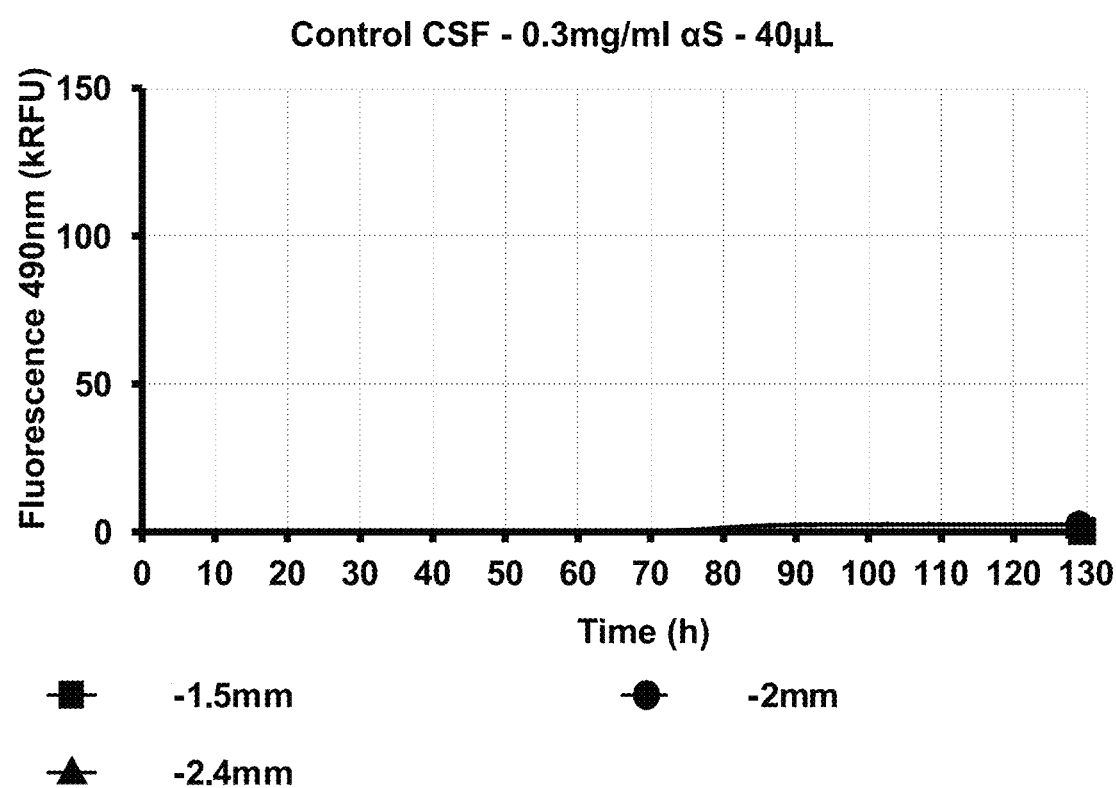
Figure 8C:
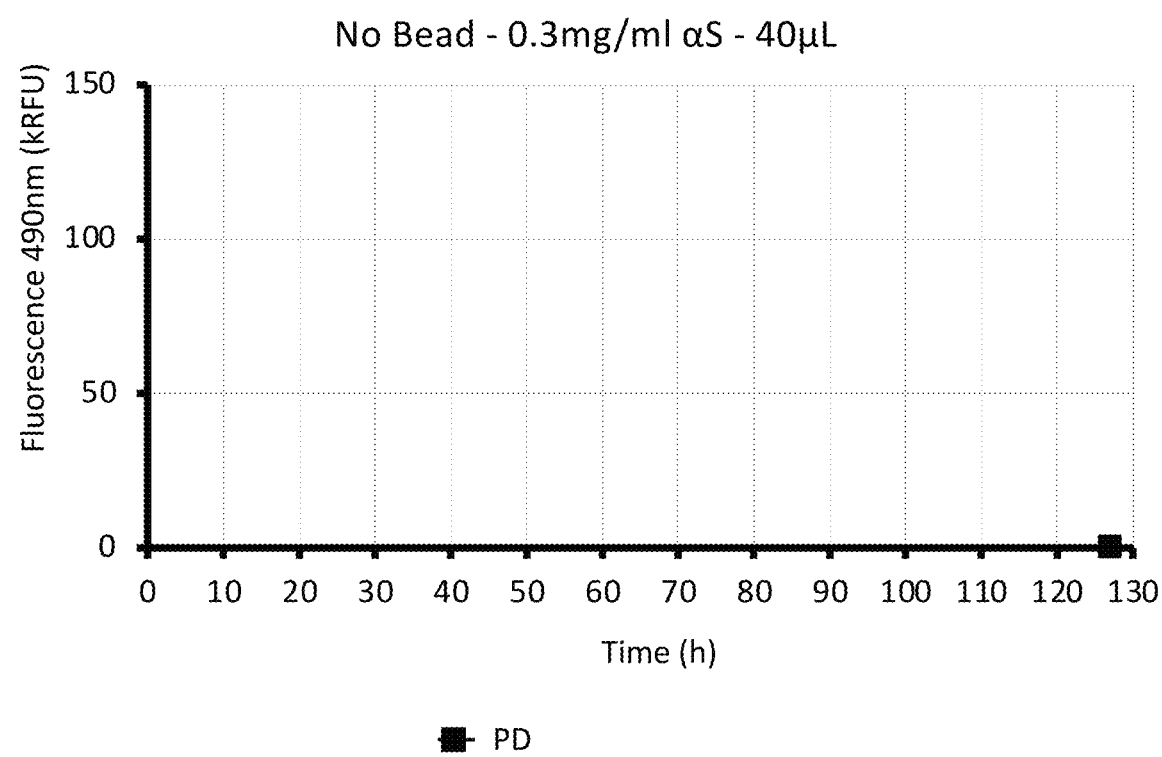

A different control CSF sample was used to evaluate self-aggregation (FIG. 8B). Similar results were obtained as with the previous control CSF (FIG. 7B). 2.38 mm beads showed a very low self-aggregation signal after 80 h.

Figure 9A:
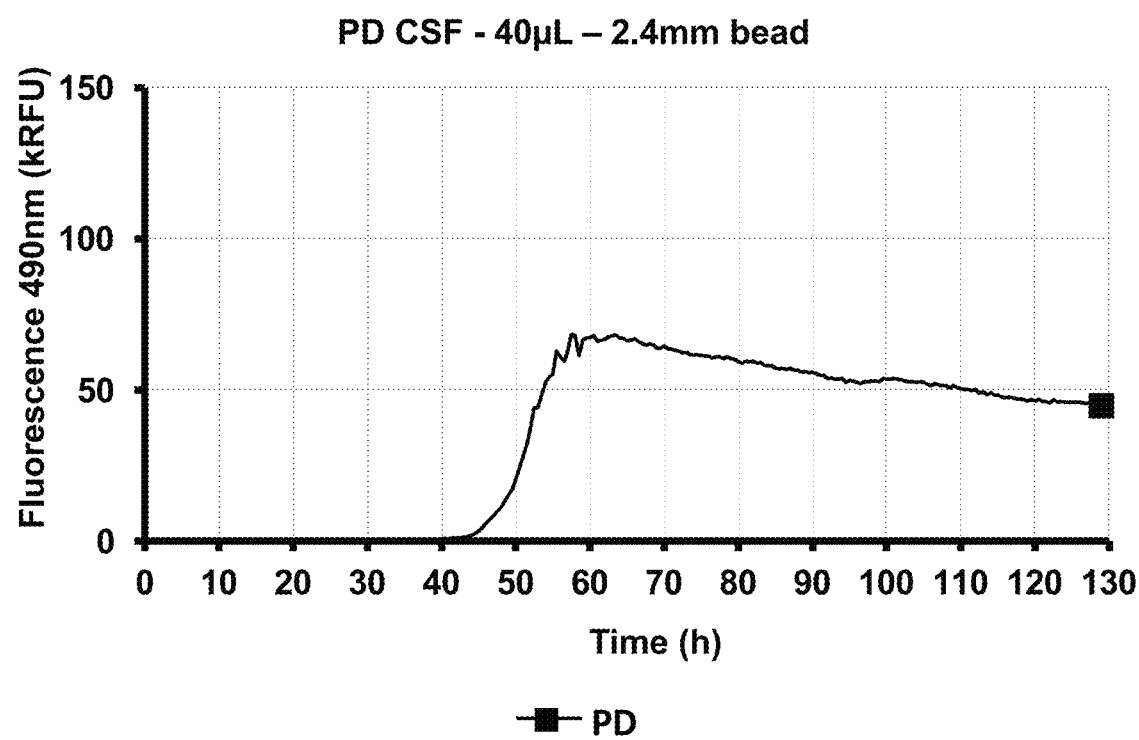
FIGS. 9A-9B demonstrate example results when PMCA was carried out using 2.38 mm $Si_3N_4$ beads, with one bead per well, using recombinant α-syn seeds at 37° C., 800 rpm, for 1 minute on and 29 minutes off, with A) showing the fluorescence representing aggregation for PMCA carried out on a CSF sample obtained from a subject having PD, with B) showing the result obtained using a control CSF sample.
Figure 9B:
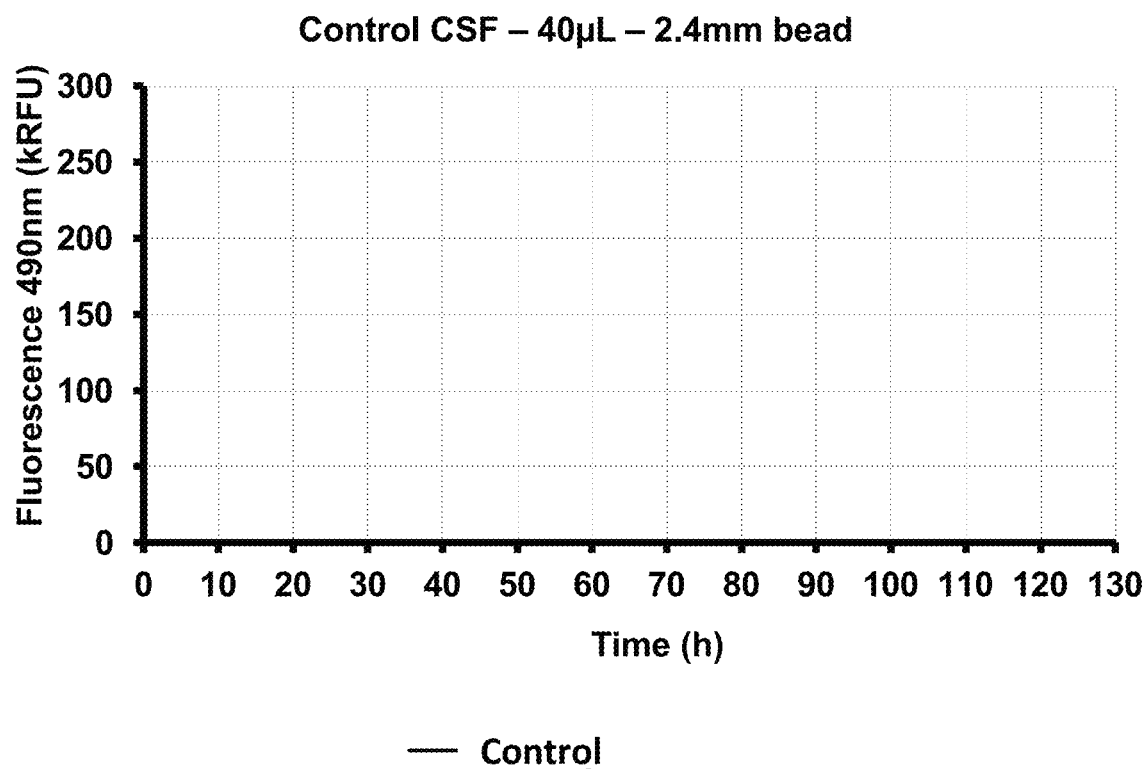

By reducing the temperature back to 37° C., the control samples remained flat while the PD sample is positive before 50 h (FIGS. 9A and 9B). When running the assay at 42° C., the time to reach 50% of the maximum aggregation (T50) for the PD CSF sample was 35 h, while the T50 at 37° C. was 41 h. Therefore, the elimination of self-aggregation by reducing the temperature resulted in only a 6 h delay in the aggregation of the PD-CSF sample.

Example 2: Comparison of the Results Obtained Using "Slow" and "Fast" PMCA

Experiments were carried out to compare the results obtained using the slow (SA) and fast (FA) PMCA assays. To be clear, the SA and FA are defined below:

| Parameter | Slow Assay (SA) | Fast Assay (FA) |
|---|---|---|
| Buffer ([ ] (mM) and pH) | 100 mM PIPES pH 6.50 | 100 mM PIPES pH 6.50 |
| [NaCl] (mM) | 500 | 500 |
| ThT (μM) | 5 | 10 |
| Detergent (%) | — | — |
| Additional reagents | — | — |
| Substrate | Recombinant C-terminal histag αSyn (MW = 15,283 mg/mmol) | Recombinant C-terminal histag αSyn (MW = 15,283 mg/mmol) |
| [substrate] (μM) | 65.4 μM | 19.6 μM |
| [substrate] (mg/mL) | 1 | 0.3 |
| CSF sample (μL) | 40 | 40 |
| Shaking type | Orbital | Orbital |
| Shaking speed (rpm) | 500 | 800 |
| Shaking time (min) | 1 | 1 |
| Incubation time (min) | 29 | 29 |
| Beads material | — | $Si_3N_4$ |
| Beads size (mm) | — | 2.38 |
| Amount of beads | — | 1 (ea) |
| Temperature (° C.) | 37 | 37 |
| Reaction volume (μL) | 200 | 200 |
| CSF replicates (ea) | 3 | 3 |
| Positive criteria | 3 positive replicates | 3 positive replicates |

139 de-identified CSF samples, 6 healthy control pooled CSF samples, and 6 PD pooled CSF samples were analyzed in parallel using the SA and FA αS-PMCA assays. The same substrate, same consumable lots, and same reagents were used for this direct comparison. PMCA was performed in triplicate in both cases. There were 59 PD samples and the FA detected 51 as positive, while the SA detected 36. Of the 60 control samples, the SA identified 56 negatives while the FA identified 52 as negative (57 using the algorithm described in U.S. Provisional Patent Application No. 63/073,424).

Figure 10A:
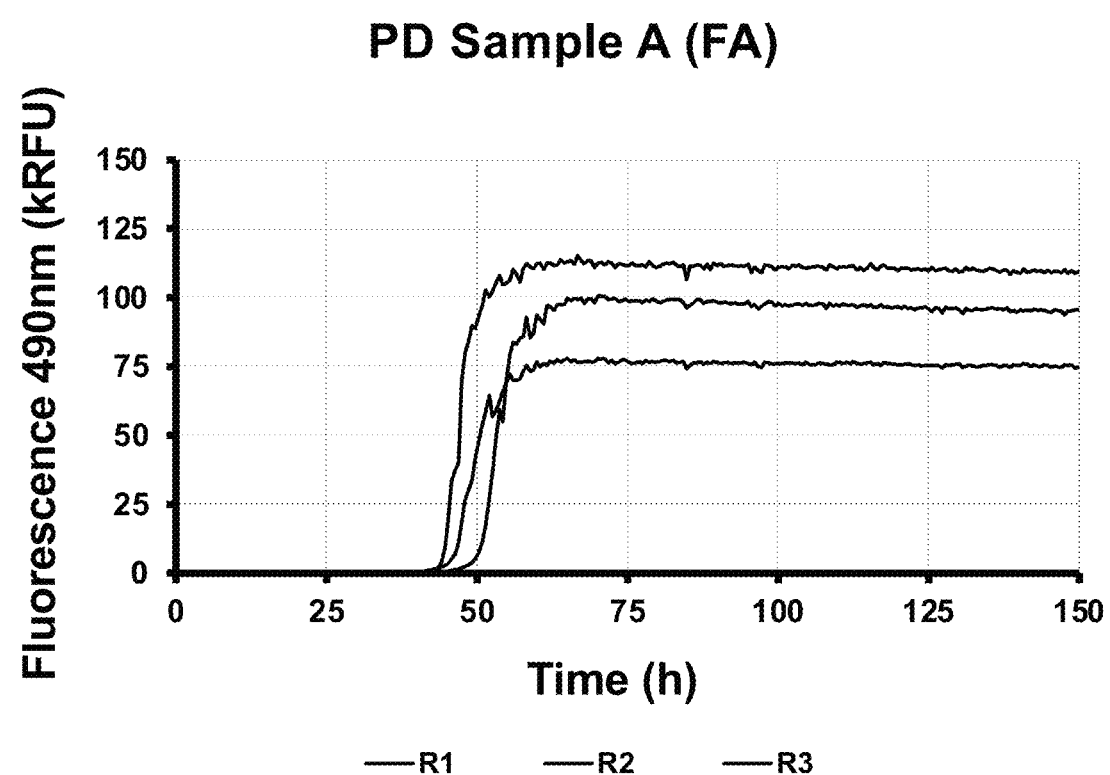
FIGS. 10A-10B demonstrate that an example fast assay (2.38 mm $Si_3N_4$ beads blocked with bovine serum albumin (BSA), with one bead per well, using recombinant α-syn seeds at 37° C., 800 rpm, for 1 minute on and 29 minutes off) (FIG. 10A) is more consistent and over 2× faster than a beadless assay (FIG. 10B) when analyzing a PD sample. The three traces represent the same sample tested in triplicate.
Figure 10B:
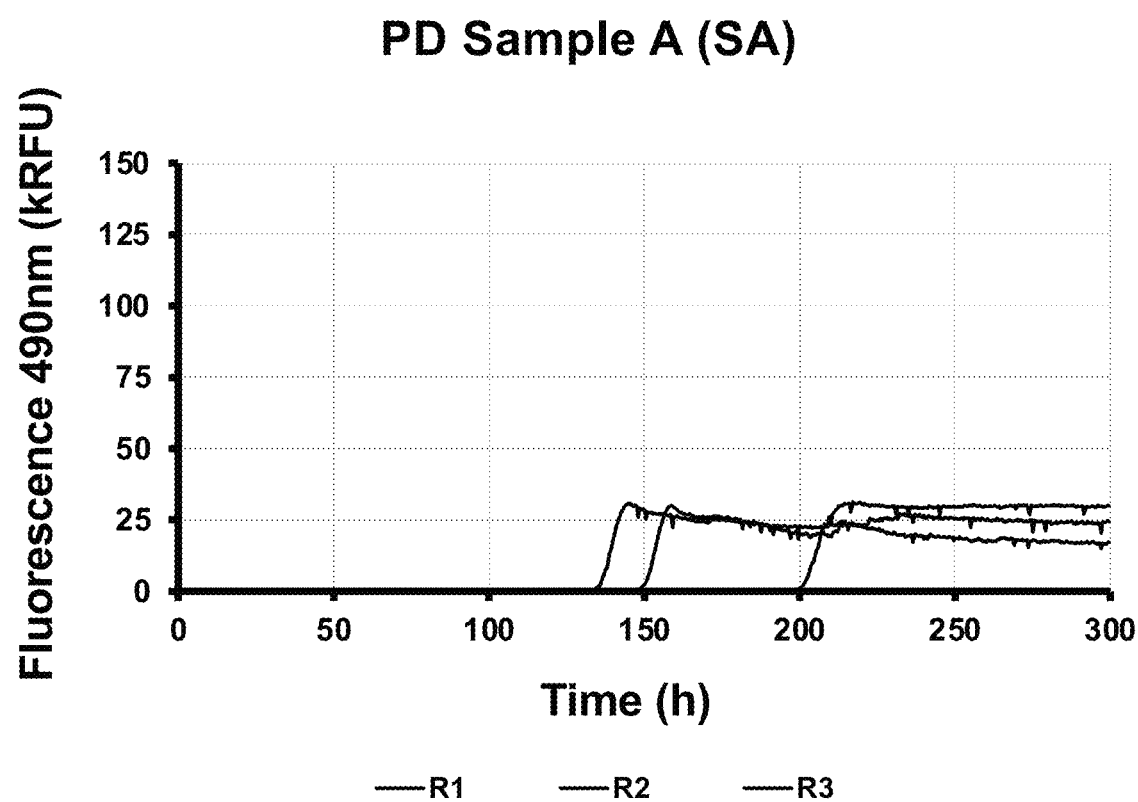
Figure 11A:
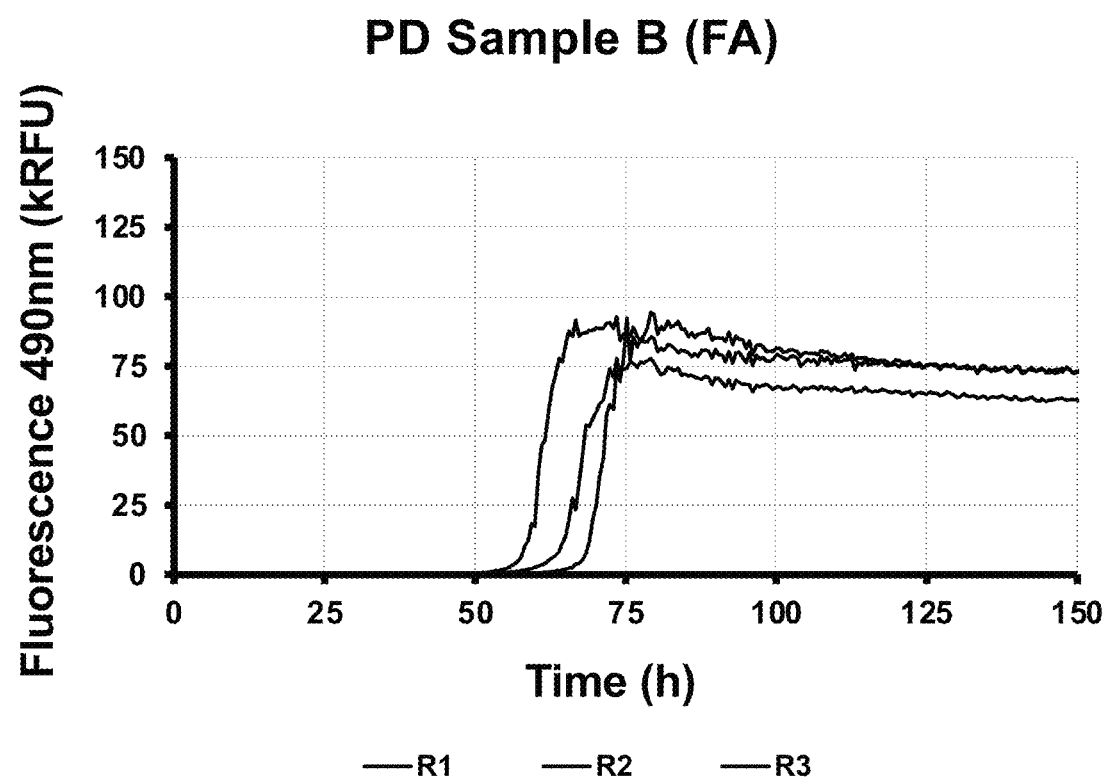
FIGS. 11A-11B demonstrate that an example fast assay (2.38 mm $Si_3N_4$ beads blocked with BSA, with one bead per well, using recombinant α-syn seeds at 37° C., 800 rpm, for 1 minute on and 29 minutes off) (FIG. 11A) is much faster than a beadless assay (FIG. 11B) when analyzing a PD sample. The three traces represent the same sample tested in triplicate.
Figure 11B:
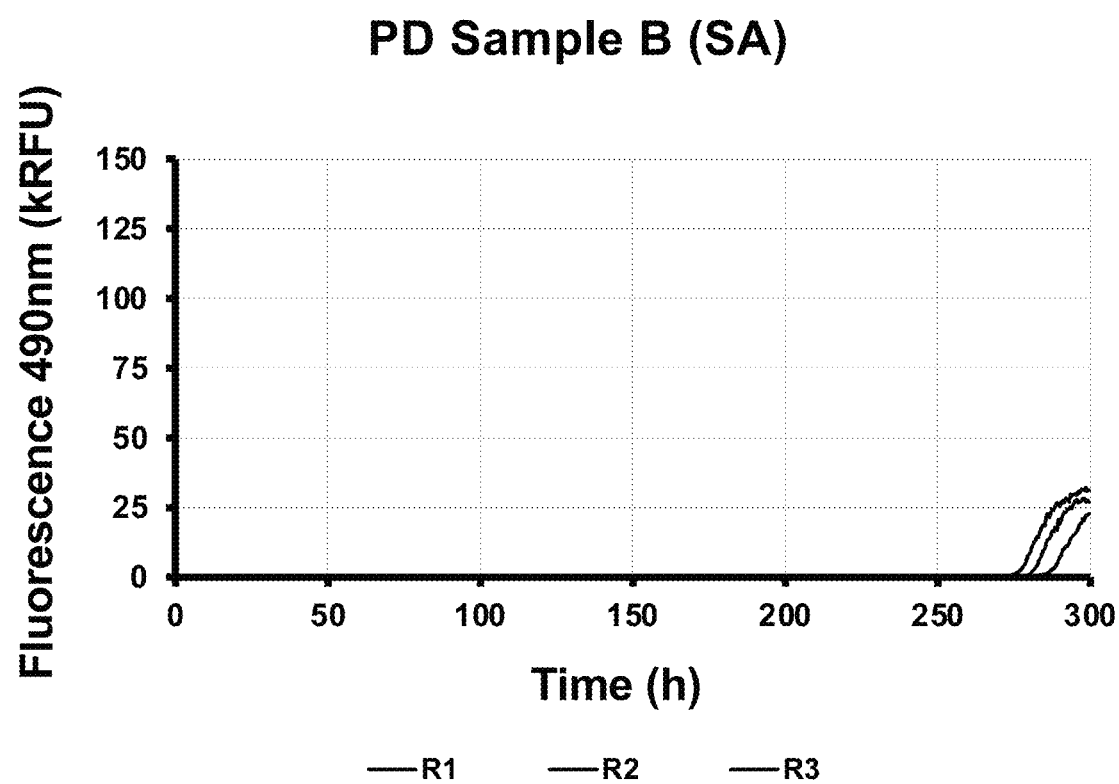
Figure 12A:
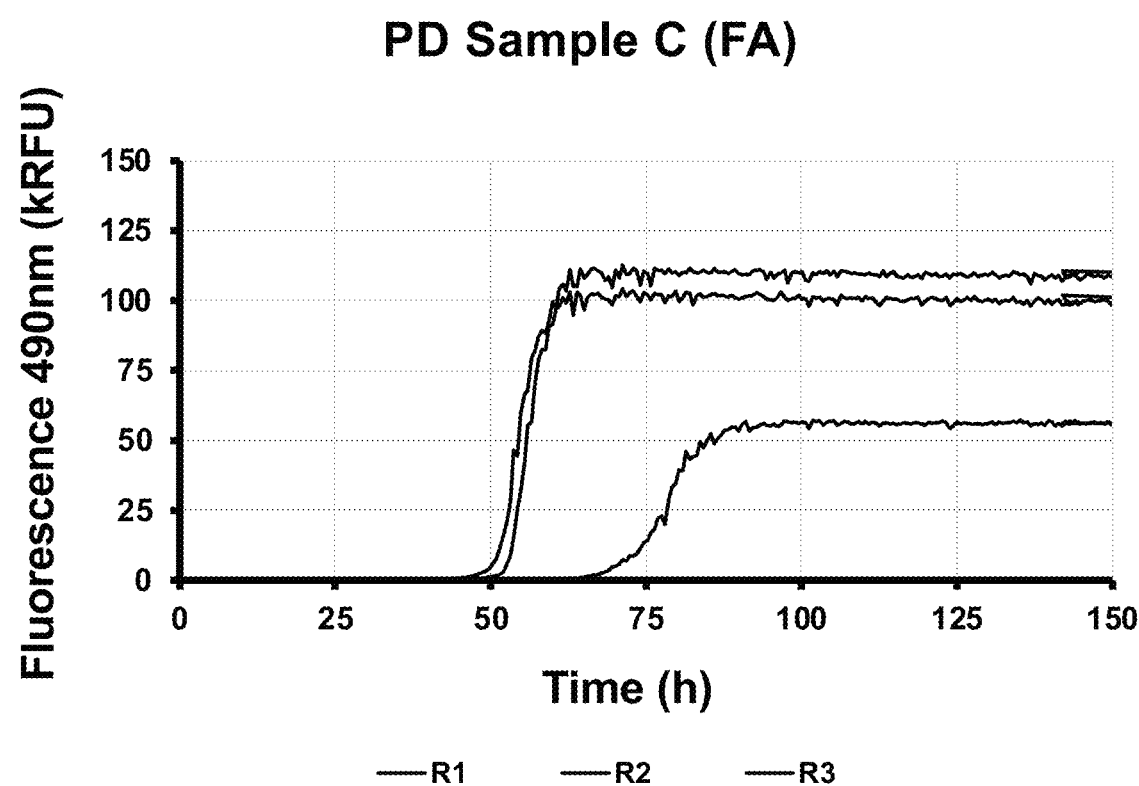
FIGS. 12A-12B demonstrate the superior sensitivity in an example fast assay (2.38 mm $Si_3N_4$ beads blocked with BSA, with one bead per well, using recombinant α-syn seeds at 37° C., 800 rpm, for 1 minute on and 29 minutes off) (FIG. 12A) compared to a beadless assay (FIG. 12B) when analyzing a PD sample. The three traces represent the same sample tested in triplicate.
Figure 12B:
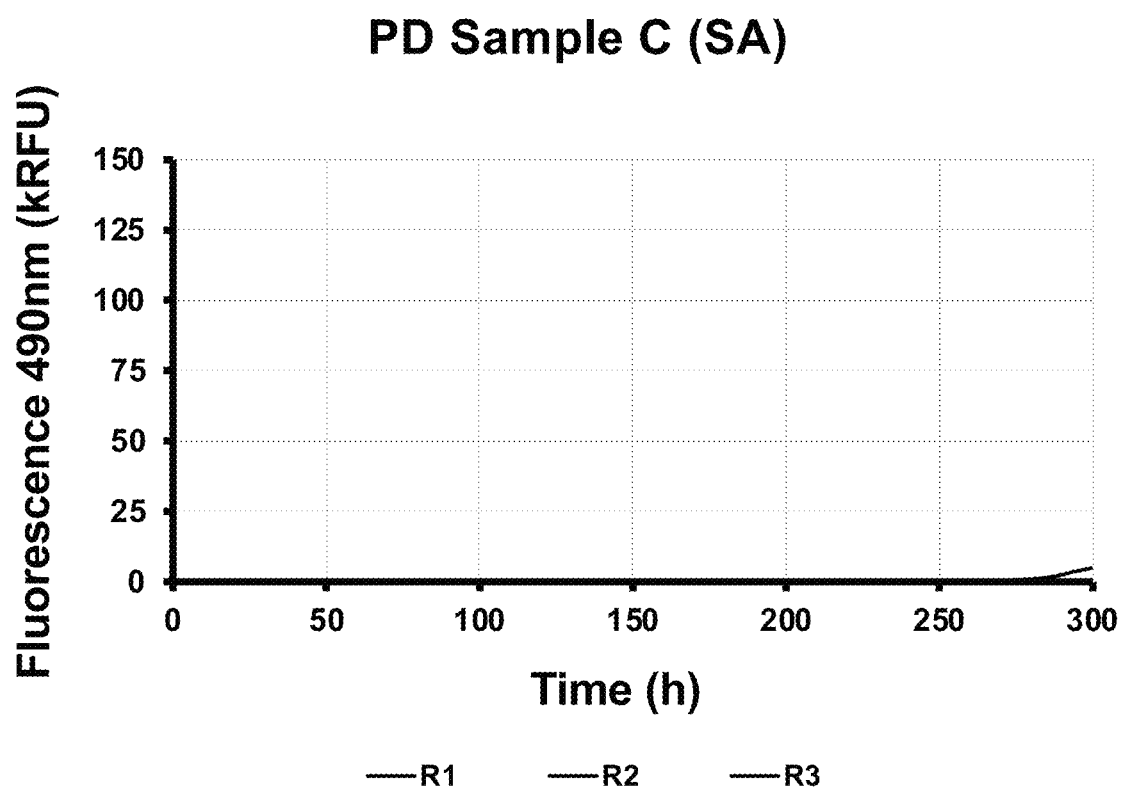
Figure 13A:
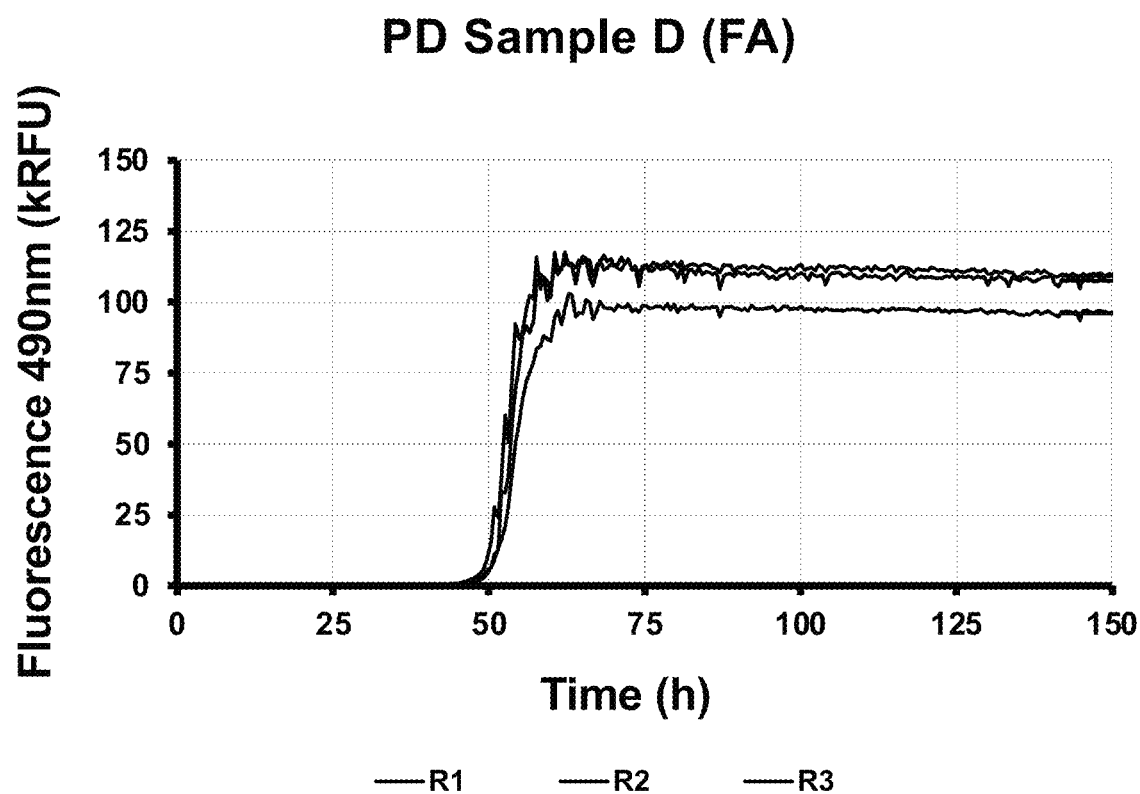
FIGS. 13A-13B demonstrate decreased variability and higher sensitivity of an example fast assay (2.38 mm $Si_3N_4$ beads blocked with BSA, with one bead per well, using recombinant α-syn seeds at 37° C., 800 rpm, for 1 minute on and 29 minutes off) (FIG. 13A) compared to a beadless assay (FIG. 13B) when analyzing a PD sample. The three traces represent the same sample tested in triplicate.
Figure 13B:
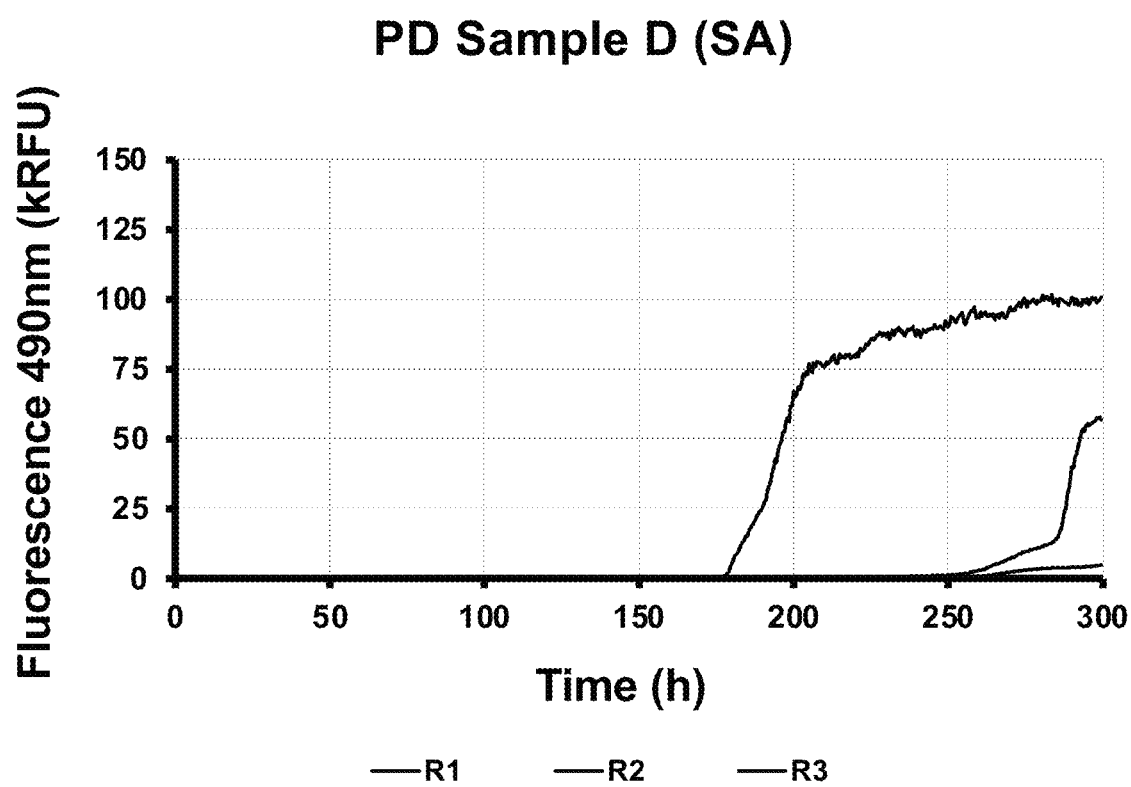

Some of the samples showed variability in terms of T50 when using the SA (FIG. 10B), but the three replicates look very consistent in the FA (FIG. 10A). One sample that was barely positive in the SA (FIG. 11B) was quickly detected as positive in the FA (FIG. 11A). Moreover, the signal and complete curve allow the identification of this sample as PD much more reliably in the FA than the SA. One PD sample that was counted as negative in the SA (FIG. 12B) was, in fact, correctly identified as strongly positive in the FA (FIG. 12A). Samples like this strongly suggest that the FA has a lower detection limit or an overall higher sensitivity compared to the SA. FIG. 13B demonstrates variability in the SA, displaying curves that do not reach plateau or that draw a non-classical aggregation curve. The FA (FIG. 13A), on the other hand, shows reproducible, complete, and classic aggregation curves in all three replicates of the PD CSF analyzed.

Data analysis of the project described in FIGS. 9-13 (139 samples) resulted as shown in Table I. The FA algorithm is described in U.S. Provisional Patent Application No. 63/073,424.

TABLE I

PMCA results of PD and Ctrl samples analyzed with the SA and FA

| | Slow assay | Fast assay | Fast assay - Algorithm |
|---|---|---|---|
| Positive PD | 36 | 51 | 51 |
| Negative PD | 12 | 6 | 6 |
| Inconclusive PD | 11 | 2 | 2 |
| Total PD | 59 | 59* | 59* |
| Negative Ctrl | 56 | 52 | 57 |
| Positive Ctrl | 1 | 3 | 3 |
| Inconclusive Ctrl | 3 | 5 | 0 |
| Total Ctrl | 60 | 60 | 60 |
| Conclusive PMCA results | 105 | 112 | 117 |
| Right call (positive PD + negative Ctrl) | 92 | 103 | 108 |
| Agreement conclusive call with clinical diagnosis | 88% | 92% | 92% |
| Sensitivity (excluding inconclusives) | 75% | 89.5% | 89.5% |
| Specificity (excluding inconclusives) | 98.2% | 94.5% | 95% |
| Total inconclusive samples (re-test recommended) | 14 | 7 | 2 |

*1 additional PD sample was analyzed in the FA assay only; it was positive.

Example 3: Fast α-Syn PMCA (aS-PMCA) for Detection of α-Syn Seeds Using Blocked Beads An assay has now been developed that uses a reasonable concentration of substrate, generates complete aggregation curves to extract kinetic parameters, is faster than the slower PMCA assay, and that can be scaled up in terms of instrumentation and workflow. The method uses 0.3 mg/ml (19.6 μM) of recombinant α-S, runs for 150 h, the entirety of the aggregation curve is recorded (complete slope and plateau), and shakes for 1 min every 30 min, which means one instrument can run 8-9 plates at a time. A significant feature is the inclusion of blocked 2.38 mm $Si_3N_4$ beads.

Beads were initially obtained from the bead distributer BC Precision. Beads of several sizes were compared, and it was found that 2.38 mm beads produced the fastest aggregation, as described in Example 1. Specifically, the beads were Grade 5, ³⁄₃₂" inch/2.38125 mm $Si_3N_4$ ceramic balls weighing 0.00081863 oz/0.0232 g. 45 CSF samples were evaluated using these 2.38 m $Si_3N_4$ beads from BC Precision (BC beads), and it was found that some runs showed the expected results, but some others did not (Table 1B, col 1). Beads from lot #B21 were used for most of the experiments, and it was found that nearly 50% of the control samples showed self-aggregation, and 16.7% of the samples were inconclusive. Another lot #, B37, was used to evaluate a few samples and confirm the inadequacy of these beads. Of the three samples analyzed, two were positive and one was inconclusive (Table 1B, col 2). While not intending to be bound by theory, is believed that that PD samples aggregate faster because the beads increase the shaking efficiency, accelerating the growth of the α-S aggregates present in PD-CSF. In the case of control donors, there are no α-S aggregates in the CSF, which means that the beads accelerate the nucleation of de novo seeds. Since shaking accelerates the fragmentation of already formed seeds, the explanation for de novo formation of seeds may be the surface interaction of the bead and the components of the reaction. To solve the self-aggregation problem, the surface of the beads was blocked using a solution of BSA in water, as described in Example 4.

TABLE 1A

αS-PMCA

|  | SA | FA |  |
|---|---|---|---|
|  | No beads | No beads | BC beads no blocking |
| bead lot# |  |  | All combined (B21, B37) |
| #samples | 173 (76 PD, 97 Ctr) | 184 (105 PD, 79 Ctrl) | 45 (23 PD, 22 Ctrl) |
| Sensitivity | 88.5% | 95% | 100.0% |
| Specificity | 96.9% | 90% | 42.9% |
| Inconclusives | N/A | N/A | 17.8% |
| column # | 1 | 2 | 3 |

TABLE 1B

αS-PMCA
FA

|  | BC beads no blocking | BC beads no blocking | BC beads water blocking | BC beads water blocking |
|---|---|---|---|---|
| bead lot# | B21 | B37 | All combined (B21, B33, B36, B37) | B21 |
| #samples | 42 (23 PD, 19 Ctrl) | 3 Ctrl | 211 (22 PD, 189 Ctrl) | 133 (20 PD, 113 Ctrl) |
| Sensitivity | 100.0% | — | 90.5% | 89.5% |
| Specificity | 50.0% | 0.0% | 82.3% | 94.3% |
| Inconclusives | 16.7% | 33.3% | 10.0% | 6.0% |
| column # | 4 | 5 | 6 | 7 |

Example 4: BC Beads Blocked with BSA in Water

BC beads blocked with BSA in water were used to analyze 133 samples, reaching 89.5% sensitivity and 94.3 specificity (Table 1B, col 7). This is a substantial improvement compared to the unblocked B21 beads (Table 1B, col 4), with an improvement in specificity of 44.3%. The reproducibility was evaluated by using other lots of the same beads (B33, B36, and B37) with the same assay conditions. Since the main problem was self-aggregation, only control samples were analyzed. Blocked B37 (Table 1C, col 10) showed a substantial improvement compared to the unblocked B37 beads (Table 1B, col 5). Blocked B36 BC beads showed very similar results (Table 1C, col 9). However, lot B33 performed quite poorly (Table 1C, col 8), since 66% of the control samples showed self-aggregation and therefore, were catalogued either positive (false positive) or inconclusive.

TABLE 1C

αS-PMCA
FA

|  | BC beads water blocking | BC beads water blocking | BC beads water blocking | BC beads optimized blocking |
|---|---|---|---|---|
| bead lot# | B33 | B36 | B37 | All combined (B33, B37) |
| #samples | 45 (2 PD, 43 Ctrl) | 15 Ctrl | 18 Ctrl | 25 (1 PD, 24 Ctrl) |
| Sensitivity | 100.0% | — | — | 100.0% |
| Specificity | 50.0% | 92.3% | 100.0% | 61.1% |
| Inconclusives | 15.6% | 13.3% | 11.1% | 24.0% |
| column # | 8 | 9 | 10 | 11 |

The beads were blocked with a solution of BSA in PIPES (1% BSA in 100 mM PIPES pH 6.50) (Table 1C; Table 1D). This new blocking procedure greatly reduced self-aggregation when using B37 beads (Table 1D, col. 13). These B37 beads already worked to an acceptable level blocking with BSA in water (Table 1C, col. 10), but when blocked with BSA in PIPES, the number of inconclusive samples decreased from 11.1% to 0%. B33 beads did not work even when blocked with BSA in PIPES, which indicates that there is some distinctive feature in B33 that could not be fixed by blocking.

A bead manufacturer, Tsubaki-Nakashima (TN), produces high quality $Si_3N_4$ beads, with sufficient quality documentation and stringent specs. Grade 3 beads, which are rounder and smoother than the grade 5 beads from BC precision, were used. TN also specifies the quality of the $Si_3N_4$ raw material to be according to the ASTM. Since BSA-PIPES blocking was effective reducing self-aggregation of B37 (compared to no blocking or blocking in water), it was used to block TN beads for the αS-PMCA assay (Table 1D, col 14, Table 1E cols 15-17). B41, B46, and B47 are different purchases of the same production lot. 610 samples were analyzed and great sensitivity and specificity were achieved, with only 8% inconclusive results. 2 additional production lots B44 and B45-B48-B49 (these three are three purchases of the same production lot) were evaluated. When using control samples only for evaluation, these two additional production lots did not show self-aggregation, in agreement with B41-B46-B47.

TABLE 1D

| | αS-PMCA FA | | |
|---|---|---|---|
| | BC beads optimized blocking | BC beads optimized blocking | TN beads optimized blocking |
| bead lot# | B33 | B37 | All combined (B41, B44, B45, B46, B47) |
| #samples | 16 Ctrl | 9 (1 PD, 8 Ctrl) | 619 (173 PD, 449 Ctrl) |
| Sensitivity | — | 100.0% | 96.30% |
| Specificity | 30.0% | 100.0% | 97.10% |
| Inconclusives | 37.5% | 0.0% | 8.20% |
| column # | 12 | 13 | 14 |

TABLE 1E

| | αS-PMCA FA | | |
|---|---|---|---|
| | TN beads optimized blocking | TN beads optimized blocking | TN beads optimized blocking |
| bead lot# | B41, B46, B47 | B44 | B45, B48, B49 |
| #samples | 610 (173 PD, 437 Ctrl) | 4 Ctrl | 5 Ctrl |
| Sensitivity | 96.3% | — | — |
| Specificity | 97.0% | 100.0% | 100.0% |
| Inconclusives | 8.4% | 0.0% | 0.0% |
| column # | 15 | 16 | 17 |

Example 5: Comparison Using Blocked $Si_3N_4$ Beads Vs. Unblocked Borosilicate Glass Beads The αS-PMCA reaction conditions used to generate the data shown in FIGS. 14A, 14B, 15A, and 15B comprised 160 μL of a PMCA mix (100 mM PIPES-NaOH pH 6.5 [Sigma, cat #80635-50G], 500 mM NaCl [Lonza, cat #51202], 10 μM ThT [Sigma, cat #T3516-25G], and 0.3 mg/ml (19.6 μM) of SEQ ID NO. 2 (rec-aS), and 40 μL of CSF.

Where $Si_3N_4$ beads were used, the beads were blocked with 1% BSA in 100 mM PIPES buffer having a pH of 6.5 prior to contacting the beads with the incubation mixture. Blocked beads were washed twice with 100 mM PIPES having a pH of 6.5. The beads had a diameter of 2.38 mm.

Where borosilicate glass beads were used, the beads were unblocked. The beads had a diameter of 2.45 mm.

Figure 14A:
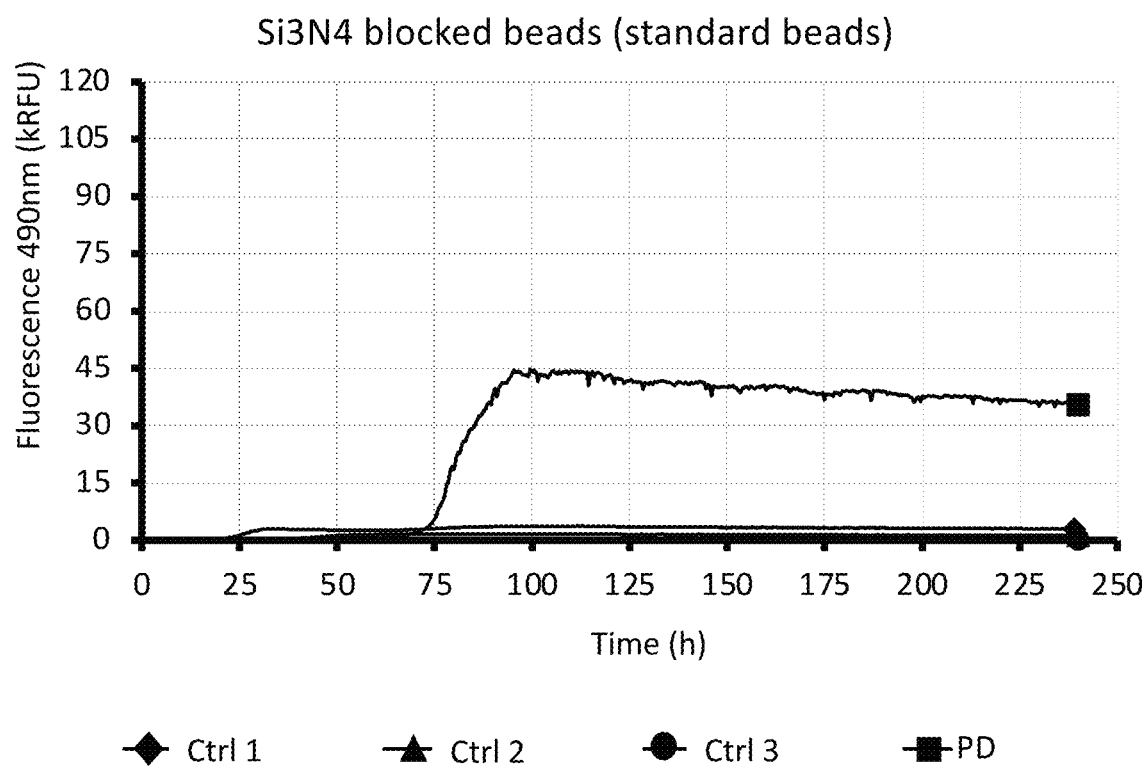
FIGS. 14A-14B show example results of running the fast assay conditions using different types of beads on one PD CSF sample (PD) and three controls. Thus.
Figure 14B:
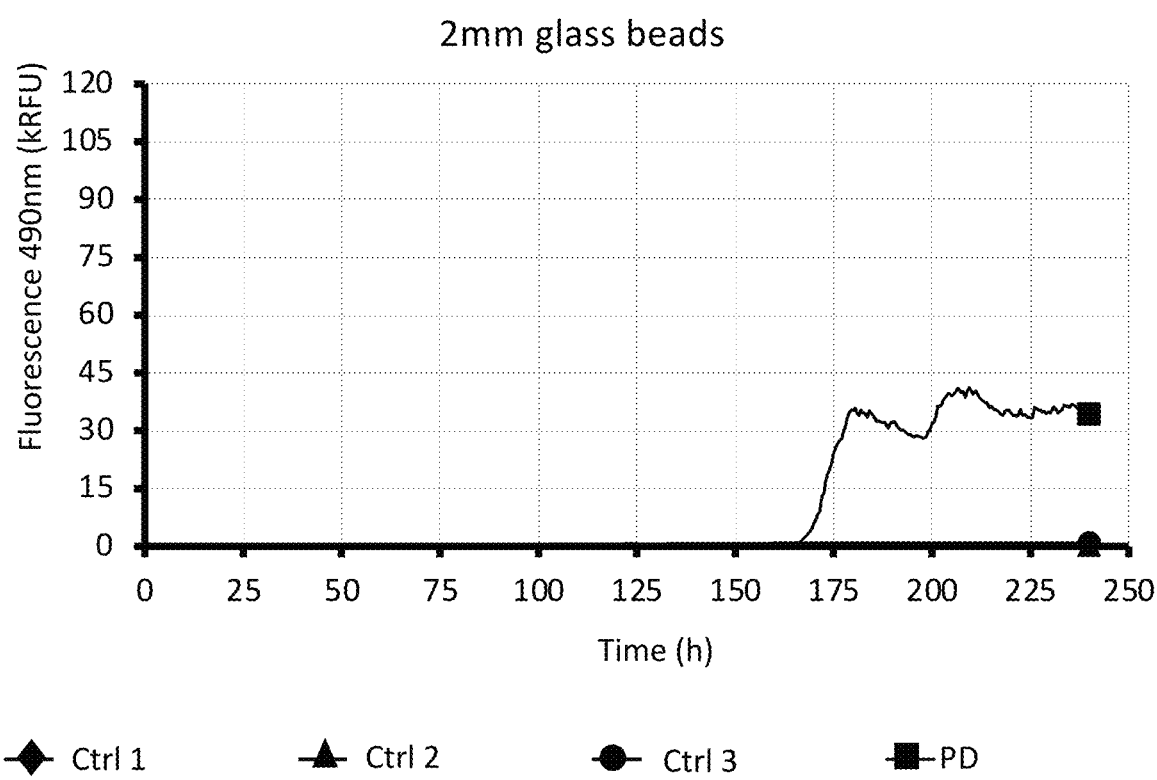

FIGS. 14A-14B show example results of using the two different bead types on a PD CSF sample (PD) and three controls. Thus, FIG. 14A shows example results of using 2.38 mm $Si_3N_4$ beads blocked with BSA; the PD sample was positive around 75 h, while all three controls were negative. FIG. 14B shows example results of using unblocked 2.45 mm borosilicate glass beads; the PD sample was positive around 170 h, while all three controls were negative.

Figure 15A:
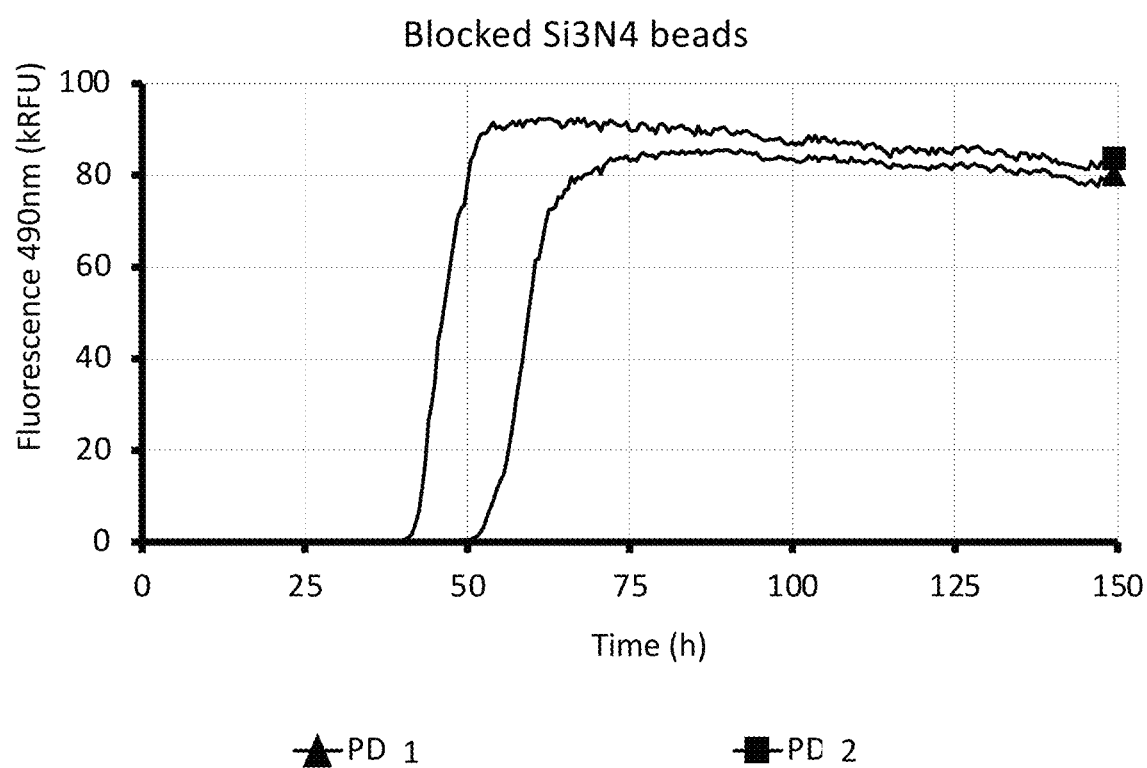
FIGS. 15A-15B show example results of running the fast assay conditions using different types of beads on two PD CSF samples from different donors (PD1 and PD2). The graphs show the average of the three replicates per patient. When using either the blocked 2.38 mm $Si_3N_4$ beads (FIG. 15A) or the unblocked 2.45 mm borosilicate glass beads (FIG. 15B), both PD samples were positive. PD2 started aggregating around 40 h and PD1 around 50 h with the $Si_3N_4$ beads. The aggregation curves are very reproducible, and the plateau shows very consistent fluorescence values. When using 2.45 mm borosilicate glass beads, there was a delay in aggregation of 10*h* and 25*h* for PD2 and PD1, respectively.
Figure 15B:
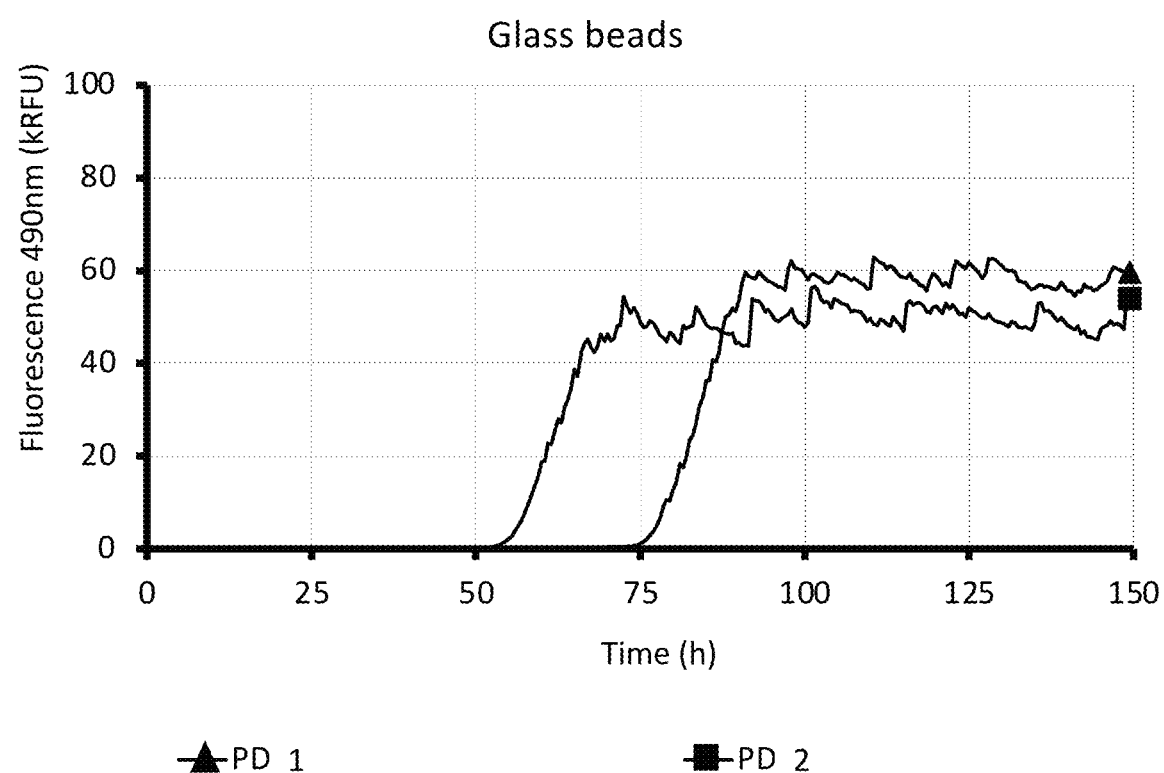

FIGS. 15A-15B show example results of using the two different bead types on two PD CSF samples from different donors (PD1 and PD2). The graphs show the average of the three replicates per patient. When using either the blocked 2.38 mm $Si_3N_4$ beads (FIG. 15A) or the unblocked 2.45 mm borosilicate glass beads (FIG. 15B), both PD samples were positive. PD2 started aggregating around 40 h and PD1 around 50 h with the $Si_3N_4$ beads. The aggregation curves are very reproducible, and the plateau shows very consistent fluorescence values. When using 2.45 mm borosilicate glass beads, there was a delay in aggregation of 10$h$ and 25$h$ for PD2 and PD1, respectively.

Example 6: Addition of Sarkosyl to FA Conditions

Figure 24A:
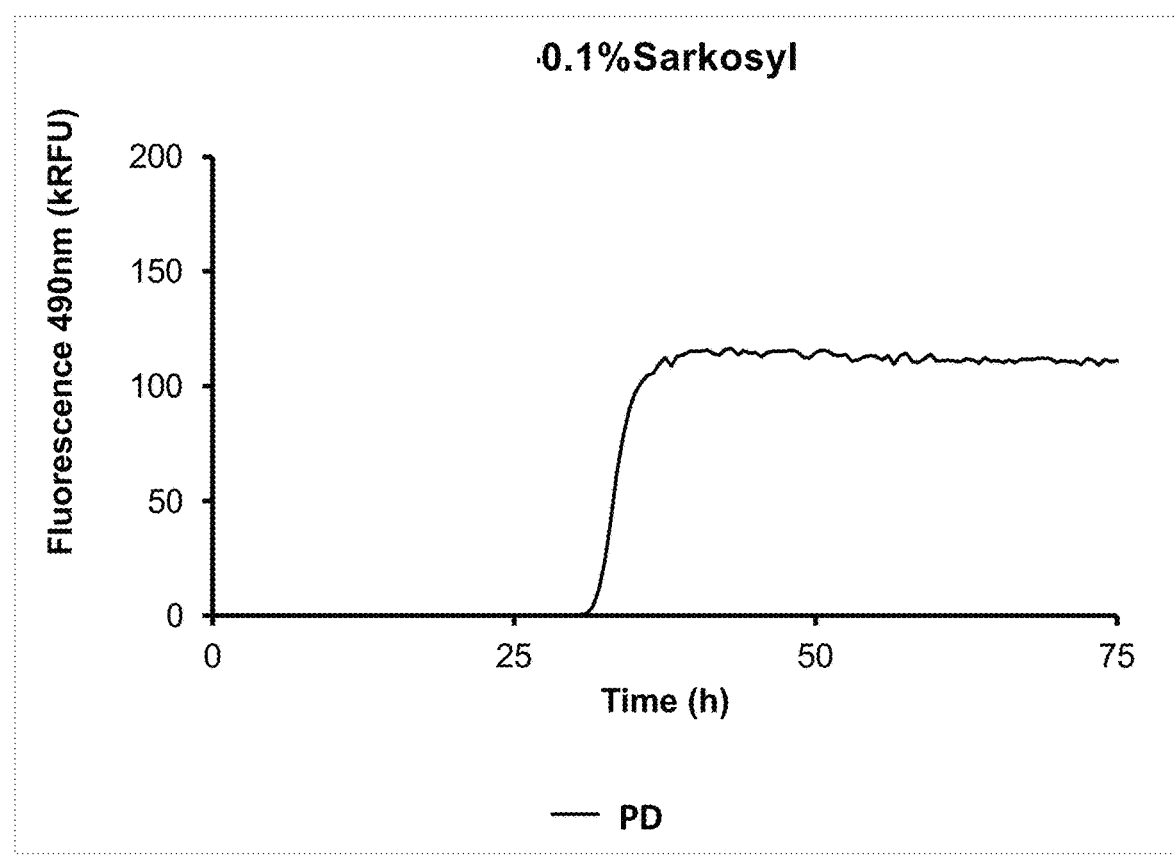
FIGS. 24A-24B show example results of including 0.1% w/v sarkosyl concentration in 1×PBS in an example fast assay (2.38 mm $Si_3N_4$ beads blocked with BSA, with one bead per well, using recombinant α-syn seeds at 37° C., 800 rpm, for 1 minute on and 29 minutes off), with A) showing the fluorescence representing aggregation for PMCA carried out on a CSF sample obtained from a subject having PD, with B) showing the result obtained using a control CSF sample.
Figure 24B:
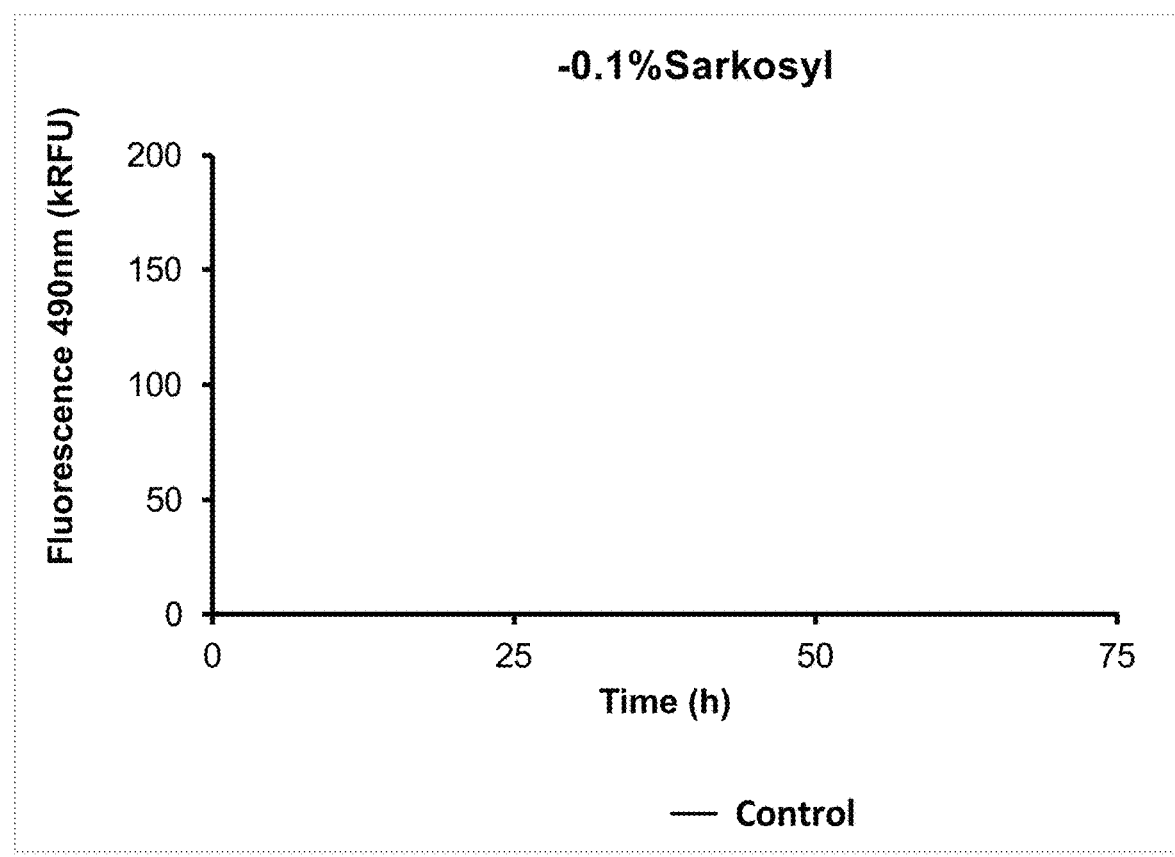

The αS-PMCA reaction conditions used to generate the data shown in FIGS. 24A and 24B comprised 160 μL of a PMCA mix (100 mM PIPES-NaOH pH 6.5 [Sigma, cat #80635-50G], 500 mM NaCl [Lonza, cat #51202], 10 μM ThT [Sigma, cat #T3516-25G], and 0.3 mg/ml (19.6 μM) of SEQ ID NO. 2 (rec-aS), and 40 μL of CSF, along with 0.1% w/v sarkosyl concentration in 1×PBS.

FIG. 24A shows example results of including 0.1% w/v sarkosyl concentration in 1×PBS in an example fast assay (2.38 mm $Si_3N_4$ beads blocked with BSA, with one bead per well, using recombinant α-syn seeds at 37° C., 800 rpm, for 1 minute on and 29 minutes off), with A) showing the fluorescence representing aggregation for PMCA carried out on a CSF sample obtained from a subject having PD, with B) showing the result obtained using a control CSF sample. FIG. 24A showed a positive result within one day, a significant acceleration.

The complete disclosure of all patents, patent applications, and publications, and electronically available material cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. A method for detecting the presence of α-synuclein (α-syn) aggregate in a biological sample, the method comprising:
   (A) providing a biological sample;
   (B) providing a pre-incubation mixture, the pre-incubation mixture comprising:
      (1) a monomeric α-syn protein;
      (2) a buffer composition;
      (3) a salt;
      (4) a fluorescent protein aggregation indicator; and
      (5) a $Si_3N_4$ bead comprising a coating of bovine serum albumin;
   (C) combining the biological sample and the pre-incubation mixture to form an incubation mixture;
   (D) incubating the incubation mixture with intermittent agitation cycles to form an incubated mixture;
   (E) illuminating the incubated mixture with a wavelength of light that excites the fluorescent protein aggregation indicator; and
   (F) determining a level of fluorescence during incubation, wherein an increase in the level of fluorescence during incubation indicates the presence of α-syn aggregate in the biological sample.

2. The method of claim 1, wherein the $Si_3N_4$ bead has a diameter of from about 1 mm to about 5 mm.

3. The method of claim 1, wherein the $Si_3N_4$ bead has a diameter of greater than 2.3 mm.

4. The method of claim 1, wherein the biological sample comprises human cerebrospinal fluid (CSF).

5. The method of claim 1, wherein the monomeric α-syn protein is present in a concentration of from about 5 μM to about 30 μM.

6. The method of claim 1, wherein the monomeric α-syn protein comprises SEQ ID NO. 2.

7. The method of claim 6, wherein the monomeric α-syn protein is present in a concentration of about 19.6 μM.

8. The method of claim 1, wherein the buffer composition has a pH of between about 6.2 to about 6.5.

9. The method of claim 1, wherein the buffer composition comprises piperazine-N,N'-bis(2-ethanesulfonic acid) (PIPES).

10. The method of claim 1, wherein the salt comprises NaCl.

11. The method of claim 1, wherein the salt comprises NaCl in a concentration between about 500 mM to about 700 mM.

12. The method of claim 1, wherein the fluorescent protein aggregation indicator comprises thioflavin T (ThT).

13. The method of claim 1, wherein the intermittent agitation cycles comprise shaking.

14. The method of claim 1, wherein the pre-incubation mixture further comprises sarkosyl.

15. A method for detecting the presence of α-synuclein (α-syn) aggregate in human cerebrospinal fluid (CSF), the method comprising:
   (A) providing human CSF;
   (B) providing a pre-incubation mixture, the pre-incubation mixture comprising:
      (1) a monomeric α-syn protein in a concentration of from about 10 μM to about 30 μM;
      (2) a buffer composition having a pH between about 6.2 to about 6.5;
      (3) NaCl in a concentration between about 500 mM to about 700 mM;
      (4) thioflavin T (ThT); and
      (5) a $Si_3N_4$ bead comprising a coating of bovine serum albumin (BSA) and having a diameter greater than 2.3 mm;
   (C) combining the human CSF and the pre-incubation mixture to form an incubation mixture;
   (D) incubating the incubation mixture with intermittent agitation cycles to form an incubated mixture;
   (E) illuminating the incubated mixture with a wavelength of light that excites the ThT; and (F) determining a level of ThT fluorescence during incubation,
wherein an increase in the level of ThT fluorescence during incubation indicates the presence of α-syn aggregate in the human CSF.

16. The method of claim 15, wherein the monomeric α-syn protein comprises SEQ ID NO. 2.

17. The method of claim 16, wherein the monomeric α-syn protein is present in a concentration of about 19.6 μM.

18. A method for detecting the presence of α-synuclein (α-syn) aggregate in a biological sample, the method comprising:
(A) providing a biological sample;
(B) providing a pre-incubation mixture, the pre-incubation mixture comprising:
  (1) a monomeric α-syn protein comprising SEQ ID NO. 2;
  (2) a buffer composition;
  (3) a salt; and
  (4) a fluorescent protein aggregation indicator; and
  (5) a borosilicate glass bead having a diameter greater than 2.3 mm;
(C) combining the biological sample and the pre-incubation mixture to form an incubation mixture;
(D) incubating the incubation mixture with intermittent agitation cycles to form an incubated mixture;
(E) illuminating the incubated mixture with a wavelength of light that excites the protein aggregation indicator; and
(F) determining a level of fluorescence during incubation,
wherein an increase in the level of fluorescence during incubation indicates the presence of α-syn aggregate in the biological sample.

19. The method of claim 18, wherein the biological sample is human cerebrospinal fluid (CSF).

20. The method of claim 18, wherein:
(i) the monomeric α-syn protein is present in a concentration of from about 5 μM to about 30 μM;
(ii) the buffer composition comprises piperazine-N,N'-bis(2-ethanesulfonic acid) (PIPES) and has a pH of from about 6.2 to about 6.5;
(iii) the salt comprises NaCl in a concentration of from about 500 mM to about 700 mM;
(iv) the borosilicate glass bead has a diameter of 2.45 mm; and
(v) the fluorescent protein aggregation indicator comprises thioflavin T (ThT) in a concentration of from about 5 μM to about 10 μM.

* * * * *